US006416740B1

(12) United States Patent
Unger

(10) Patent No.: US 6,416,740 B1
(45) Date of Patent: Jul. 9, 2002

(54) ACOUSTICALLY ACTIVE DRUG DELIVERY SYSTEMS

(75) Inventor: Evan C. Unger, Tucson, AZ (US)

(73) Assignee: Bristol-Myers Squibb Medical Imaging, Inc., Princeton, NJ (US)

( * ) Notice: Subject to any disclaimer, the term of this patent is extended or adjusted under 35 U.S.C. 154(b) by 0 days.

(21) Appl. No.: 09/075,343

(22) Filed: May 11, 1998

Related U.S. Application Data

(60) Provisional application No. 60/046,379, filed on May 13, 1997.

(51) Int. Cl.[7] .............................. A61B 8/00; A61K 9/127
(52) U.S. Cl. ...................... 424/9.52; 424/9.5; 424/9.51; 424/450; 424/9.52
(58) Field of Search ................................ 424/9.52, 9.5, 424/9.51, 450

(56) References Cited

U.S. PATENT DOCUMENTS

| | | | |
|---|---|---|---|
| 3,015,128 A | 1/1962 | Sommerville et al. ......... 18/2.6 |
| 3,291,843 A | 12/1966 | Fritz et al. .................... 260/614 |
| 3,293,114 A | 12/1966 | Kenaga et al. ............... 162/168 |
| 3,401,475 A | 9/1968 | Morehouse et al. ........... 40/306 |
| 3,479,811 A | 11/1969 | Walters ......................... 57/153 |
| 3,488,714 A | 1/1970 | Walters et al. ............... 161/161 |
| 3,532,500 A | 10/1970 | Priest et al. ..................... 96/91 |
| 3,557,294 A | 1/1971 | Dear et al. ................... 424/342 |
| 3,594,326 A | 7/1971 | Himmel et al. .............. 252/316 |
| 3,615,972 A | 10/1971 | Morehouse et al. .......... 156/79 |
| 3,650,831 A | 3/1972 | Jungermann et al. ......... 134/27 |
| 3,732,172 A | 5/1973 | Herbig et al. ................ 252/316 |
| 3,873,564 A | 3/1975 | Schneider et al. ........ 270/309.6 |
| 3,945,956 A | 3/1976 | Garner ..................... 270/2.5 B |
| 3,968,203 A | 7/1976 | Spitzer et al. ................. 424/47 |
| 4,027,007 A | 5/1977 | Messina ........................ 424/46 |
| 4,089,801 A | 5/1978 | Schneider ................... 252/316 |
| 4,108,806 A | 8/1978 | Cohrs et al. ................... 521/54 |
| 4,138,383 A | 2/1979 | Rembaum et al. ..... 270/29.7 H |
| 4,162,282 A | 7/1979 | Fulwyler et al. ................ 274/9 |
| 4,179,546 A | 12/1979 | Garner et al. .................. 521/56 |
| 4,192,859 A | 3/1980 | Mackaness et al. ............. 424/5 |
| 4,224,179 A | 9/1980 | Schneider ................... 252/316 |
| 4,229,360 A | 10/1980 | Schneider et al. .......... 270/403 |
| 4,265,251 A | 5/1981 | Ticklner ..................... 128/660 |
| 4,276,885 A | 7/1981 | Tickner et al. .............. 128/660 |
| 4,310,505 A | 1/1982 | Baldeschwieler et al. ...... 424/1 |
| 4,310,506 A | 1/1982 | Baldeschwieler et al. ...... 424/1 |

(List continued on next page.)

FOREIGN PATENT DOCUMENTS

| | | |
|---|---|---|
| AU | 641363 | 3/1990 |
| AU | B-30351/89 | 3/1993 |
| DE | 25 21 003 | 8/1976 |

(List continued on next page.)

OTHER PUBLICATIONS

Remington: The science and Practice of Pharamcy, 1996, 19th ed. pp 1112–1113.*

(List continued on next page.)

*Primary Examiner*—Diana Dudash
*Assistant Examiner*—Shahnam Sharareh
(74) *Attorney, Agent, or Firm*—Woodcock Washburn LLP

(57) ABSTRACT

The present invention is directed to targeted therapeutic delivery systems comprising a gas or gaseous precursor filled microsphere wherein said gas or gaseous precursor filled microsphere comprises an oil, a surfactant, and a therapeutic compound. Methods of preparing the targeted therapeutic delivery systems are also embodied by the present invention which comprise processing a solution comprising an oil and a surfactant in the presence of a gaseous precursor, at a temperature below the gel to liquid crystalline phase transition temperature of the surfactant to form gas or gaseous precursor filled microsphere, and adding to said microspheres a therapeutic compound resulting in a targeted therapeutic delivery system, wherein said processing is selected from the group consisting of controlled agitation, controlled drying, and a combination thereof.

15 Claims, 9 Drawing Sheets

U.S. PATENT DOCUMENTS

| | | | |
|---|---|---|---|
| 4,315,514 A | 2/1982 | Drewes et al. | 128/653 |
| 4,331,654 A | 5/1982 | Morris | 424/38 |
| 4,342,826 A | 8/1982 | Cole | 435/7 |
| 4,344,929 A | 8/1982 | Bonsen et al. | 424/15 |
| 4,420,442 A | 12/1983 | Sands | 274/13 |
| 4,421,562 A | 12/1983 | Sands et al. | 106/75 |
| 4,426,330 A | 1/1984 | Sears | 270/403 |
| 4,427,649 A | 1/1984 | Dingle et al. | 424/38 |
| 4,428,924 A | 1/1984 | Millington | 424/4 |
| 4,442,843 A | 4/1984 | Rasor et al. | 128/660 |
| 4,466,442 A | 8/1984 | Hilmann et al. | 128/653 |
| 4,485,193 A | 11/1984 | Rubens et al. | 521/58 |
| 4,530,360 A | 7/1985 | Duarte | 128/419 F |
| 4,533,254 A | 8/1985 | Cook et al. | 366/176 |
| 4,534,899 A | 8/1985 | Sears | 270/403 |
| 4,540,629 A | 9/1985 | Sands et al. | 428/402 |
| 4,544,545 A | 10/1985 | Ryan et al. | 424/1.1 |
| 4,549,892 A | 10/1985 | Baker et al. | 65/21.4 |
| 4,569,836 A | 2/1986 | Gordon | 424/1.1 |
| 4,572,203 A | 2/1986 | Feinstein | 128/661 |
| 4,586,512 A | 5/1986 | Do-huu et al. | 128/660 |
| 4,603,044 A | 7/1986 | Geho et al. | 424/9 |
| 4,615,879 A | 10/1986 | Runge et al. | 424/9 |
| 4,620,546 A | 11/1986 | Aida et al. | 128/660 |
| 4,646,756 A | 3/1987 | Watmough et al. | 128/804 |
| 4,657,756 A | 4/1987 | Rasor et al. | 424/9 |
| 4,658,828 A | 4/1987 | Dory | 128/660 |
| 4,663,161 A | 5/1987 | Mannino et al. | 424/89 |
| 4,675,310 A | 6/1987 | Chapman et al. | 514/6 |
| 4,681,119 A | 7/1987 | Rasor et al. | 128/660 |
| 4,684,479 A | 8/1987 | D'Arrigo | 252/307 |
| 4,689,986 A | 9/1987 | Carson et al. | 73/19 |
| 4,693,999 A | 9/1987 | Axelsson et al. | 514/174 |
| 4,718,433 A | 1/1988 | Feinstein | 128/660 |
| 4,728,575 A | 3/1988 | Gamble et al. | 428/402.2 |
| 4,728,578 A | 3/1988 | Higgins et al. | 428/462 |
| 4,731,239 A | 3/1988 | Gordon | 424/9 |
| 4,737,323 A | 4/1988 | Martin et al. | 274/4.3 |
| 4,774,958 A | 10/1988 | Feinstein | 128/660.01 |
| 4,775,522 A | 10/1988 | Clark, Jr. | 424/9 |
| 4,776,991 A | 10/1988 | Farmer et al. | 274/4.3 |
| 4,781,871 A | 11/1988 | West, III et al. | 274/4.3 |
| 4,789,501 A | 12/1988 | Day et al. | 252/645 |
| 4,790,891 A | 12/1988 | Halliday et al. | 149/2 |
| 4,822,534 A | 4/1989 | Lencki et al. | 274/4.3 |
| 4,830,858 A | 5/1989 | Payne et al. | 424/450 |
| 4,834,964 A | 5/1989 | Rosen | 424/9 |
| 4,844,882 A | 7/1989 | Widder et al. | 424/9 |
| 4,863,717 A | 9/1989 | Keana | 424/9 |
| 4,865,836 A | 9/1989 | Long, Jr. | 424/5 |
| 4,877,561 A | 10/1989 | Iga et al. | 274/4.3 |
| 4,893,624 A | 1/1990 | Lele | 128/399 |
| 4,895,719 A | 1/1990 | Radhakrishnan | 424/45 |
| 4,898,734 A * | 2/1990 | Mathlowitz et al. | 424/426 |
| 4,918,065 A | 4/1990 | Stindl et al. | 514/179 |
| 4,919,895 A | 4/1990 | Heldebrant et al. | 422/129 |
| 4,921,706 A | 5/1990 | Roberts et al. | 424/450 |
| 4,927,623 A | 5/1990 | Long, Jr. | 424/5 |
| 4,933,121 A | 6/1990 | Law et al. | 264/4.3 |
| 4,938,947 A | 7/1990 | Nicolau et al. | 424/1.1 |
| 4,957,656 A | 9/1990 | Cerny et al. | 252/311 |
| 4,972,002 A | 11/1990 | Volkert | 521/120 |
| 4,981,692 A | 1/1991 | Popescu et al. | 424/422 |
| 4,984,573 A | 1/1991 | Leunbach | 128/653 |
| 4,985,550 A | 1/1991 | Charpiot et al. | 536/18.4 |
| 4,987,154 A | 1/1991 | Long, Jr. | 514/772 |
| 4,993,415 A | 2/1991 | Long | 128/653 A |
| 4,996,041 A | 2/1991 | Arai et al. | 424/9 |
| 5,000,960 A | 3/1991 | Wallach | 424/450 |
| 5,004,611 A | 4/1991 | Leigh | 424/450 |
| 5,008,050 A | 4/1991 | Cullis et al. | 274/4.3 |
| 5,008,109 A | 4/1991 | Tin | 424/422 |
| 5,013,556 A | 5/1991 | Woodle et al. | 424/450 |
| 5,019,370 A | 5/1991 | Jay et al. | 424/4 |
| 5,045,304 A | 9/1991 | Schneider et al. | 424/9 |
| 5,049,388 A | 9/1991 | Knight et al. | 424/450 |
| 4,229,360 C1 | 11/1991 | Schneider et al. | 270/403 |
| 5,078,994 A | 1/1992 | Nair et al. | 424/501 |
| 5,088,499 A | 2/1992 | Unger | 128/662.2 |
| 5,107,842 A | 4/1992 | Levene et al. | 128/662.02 |
| 5,114,703 A | 5/1992 | Wolf et al. | 424/5 |
| 5,123,414 A | 6/1992 | Unger | 128/654 |
| 5,135,000 A | 8/1992 | Akselrod et al. | 128/662.05 |
| 5,137,928 A | 8/1992 | Erbel et al. | 521/56 |
| 5,141,738 A | 8/1992 | Rasor et al. | 424/2 |
| 5,147,631 A | 9/1992 | Glajch et al. | 424/518 |
| 5,149,319 A | 9/1992 | Unger | 604/22 |
| 5,149,543 A | 9/1992 | Cohen et al. | 424/499 |
| 5,171,755 A | 12/1992 | D'Arrigo | 252/307 |
| 5,186,922 A | 2/1993 | Shell et al. | 128/654 |
| 5,190,766 A | 3/1993 | Ishiara | 424/489 |
| 5,190,982 A | 3/1993 | Erbel et al. | 521/56 |
| 5,192,549 A | 3/1993 | Barenolz et al. | 424/450 |
| 5,194,266 A | 3/1993 | Abra et al. | 424/450 |
| 5,195,520 A | 3/1993 | Schlief et al. | 128/660.02 |
| 5,196,183 A | 3/1993 | Yudelson et al. | 424/9 |
| 5,196,348 A | 3/1993 | Schweighardt et al. | 436/173 |
| 5,198,225 A | 3/1993 | Meybeck et al. | 424/450 |
| 5,205,287 A | 4/1993 | Erbel et al. | 128/632 |
| 5,205,290 A | 4/1993 | Unger | 128/653.4 |
| 5,209,720 A | 5/1993 | Unger | 604/22 |
| 5,213,804 A | 5/1993 | Martin et al. | 424/450 |
| 5,215,680 A | 6/1993 | D'Arrigo | 252/307 |
| 5,219,401 A * | 6/1993 | Cathignol et al. | 128/660.03 |
| 5,219,538 A | 6/1993 | Henderson eta al. | 428/402.2 |
| 5,228,446 A | 7/1993 | Unger et al. | 128/662.02 |
| 5,230,882 A | 7/1993 | Unger | 424/9 |
| 5,234,680 A | 8/1993 | Rogers, Jr. et al. | 424/9 |
| 5,247,935 A | 9/1993 | Cline et al. | 128/653.2 |
| 5,271,928 A | 12/1993 | Schneider et al. | 424/9 |
| 5,281,408 A | 1/1994 | Unger | 424/4 |
| 5,305,757 A | 4/1994 | Unger et al. | 367/7 |
| 5,310,540 A | 5/1994 | Giddey et al. | 424/9 |
| 5,312,617 A | 5/1994 | Unger et al. | 424/9 |
| 5,315,997 A | 5/1994 | Widder et al. | 128/653.3 |
| 5,315,998 A | 5/1994 | Tachibana et al. | 128/660.01 |
| 5,316,771 A | 5/1994 | Barenholz et al. | 424/450 |
| 5,334,381 A | 8/1994 | Unger | 424/9 |
| 5,339,814 A | 8/1994 | Lasker | 128/653.4 |
| 5,344,930 A | 9/1994 | Riess et al. | 544/84 |
| 5,350,571 A | 9/1994 | Kaufman et al. | 424/9 |
| 5,352,435 A | 10/1994 | Unger | 424/9 |
| 5,354,549 A | 10/1994 | Klaveness et al. | 424/3 |
| 5,358,702 A | 10/1994 | Unger | 424/9 |
| 5,362,477 A | 11/1994 | Moore et al. | 424/9 |
| 5,362,478 A | 11/1994 | Desai et al. | 424/9 |
| 5,380,519 A | 1/1995 | Schneider et al. | 424/9 |
| 5,393,524 A | 2/1995 | Quay | 424/9 |
| 5,409,688 A | 4/1995 | Quay | 424/9 |
| 5,410,516 A | 4/1995 | Uhlendorf et al. | 367/7 |
| 5,413,774 A | 5/1995 | Schneider et al. | 424/9.51 |
| 5,422,120 A * | 6/1995 | Kim | 424/450 |
| 5,425,366 A | 6/1995 | Reinhardt et al. | 128/662.02 |
| 5,433,204 A | 7/1995 | Olson | 128/661.08 |
| 5,445,813 A | 8/1995 | Schneider et al. | 424/9.51 |
| 5,456,900 A | 10/1995 | Unger | 424/9.4 |
| 5,460,800 A | 10/1995 | Walters | 429/9.6 |
| 5,469,854 A | 11/1995 | Unger et al. | 128/662.02 |
| 5,470,582 A | 11/1995 | Supersaxo et al. | 424/489 |
| 5,485,839 A | 1/1996 | Aida et al. | 128/653.1 |
| 5,487,390 A | 1/1996 | Cohen et al. | 128/662.02 |

| | | | |
|---|---|---|---|
| 5,496,535 A | 3/1996 | Kirkland .................... 424/9.37 |
| 5,498,421 A | 3/1996 | Grinstaff et al. ............ 424/450 |
| 5,501,863 A | 3/1996 | Rössling et al. ............ 424/489 |
| 5,502,094 A | 3/1996 | Moore et al. ................ 524/145 |
| 5,505,932 A | 4/1996 | Grinstoff et al. ............. 424/9.3 |
| 5,508,021 A | 4/1996 | Grinstaff et al. .......... 424/9.322 |
| 5,512,268 A | 4/1996 | Grinstaff et al. ............ 424/322 |
| 5,527,521 A | 6/1996 | Unger ........................ 424/93 |
| 5,529,766 A | 6/1996 | Klaveness et al. ......... 424/9.52 |
| 5,531,980 A | 7/1996 | Schneider et al. ......... 424/9.52 |
| 5,536,489 A | 7/1996 | Lohrmann et al. ......... 424/9.52 |
| 5,536,490 A | 7/1996 | Klaveness et al. ......... 424/9.52 |
| 5,540,909 A | 7/1996 | Schutt ....................... 424/9.52 |
| 5,542,935 A | 8/1996 | Unger et al. ................ 604/190 |
| 5,545,396 A | 8/1996 | Albert ........................ 424/93 |
| 5,547,656 A | 8/1996 | Unger ........................ 424/93 |
| 5,552,133 A | 9/1996 | Lambert et al. ........... 424/9.52 |
| 5,552,155 A | 9/1996 | Bailey et al. ............... 424/450 |
| 5,556,372 A | 9/1996 | Talish et al. .................. 601/2 |
| 5,556,610 A | 9/1996 | Yan et al. .................. 424/9.52 |
| 5,558,092 A | 9/1996 | Unger et al. ........... 128/660.03 |
| 5,558,094 A | 9/1996 | Quay .................... 128/662.02 |
| 5,558,853 A | 9/1996 | Quay ......................... 424/9.5 |
| 5,558,854 A | 9/1996 | Quay ........................ 424/9.52 |
| 5,558,855 A | 9/1996 | Quay ......................... 424/9.5 |
| 5,558,856 A | 9/1996 | Klaveness et al. ......... 424/9.37 |
| 5,560,364 A | 10/1996 | Porter .................... 128/662.02 |
| 5,562,608 A | 10/1996 | Sekins et al. ................. 604/20 |
| 5,562,893 A | 10/1996 | Lohrmann ................ 424/9.52 |
| 5,565,215 A | 10/1996 | Gref et al. .................. 424/501 |
| 5,567,413 A | 10/1996 | Klaveness et al. ......... 424/9.51 |
| 5,567,414 A | 10/1996 | Schneider et al. ......... 424/9.52 |
| 5,567,415 A | 10/1996 | Porter ....................... 424/9.52 |
| 5,567,765 A | 10/1996 | Moore et al. ................ 524/801 |
| 5,569,448 A | 10/1996 | Wong et al. ................ 424/9.45 |
| 5,569,449 A | 10/1996 | Klaveness et al. ......... 424/9.51 |
| 5,571,797 A | 11/1996 | Ohno et al. .................... 514/44 |
| 5,573,751 A | 11/1996 | Quay ........................ 424/9.52 |
| 5,573,781 A | 11/1996 | Unger et al. ................ 424/450 |
| 5,578,292 A | 11/1996 | Schneider et al. ......... 424/9.51 |
| 5,580,575 A * | 12/1996 | Unger et al. ................ 424/450 |
| 5,585,112 A | 12/1996 | Unger et al. ................ 424/450 |
| 5,593,680 A | 1/1997 | Bara et al. ................... 424/401 |
| 5,595,723 A | 1/1997 | Quay ........................ 424/89.5 |
| 5,605,673 A | 2/1997 | Schutt et al. ............... 424/9.51 |
| 5,606,973 A | 3/1997 | Lambert ................ 128/662.02 |
| 5,612,057 A | 3/1997 | Lanza et al. ................ 424/450 |
| 5,612,318 A | 3/1997 | Weichselbaum et al. ...... 514/44 |
| 5,614,169 A | 3/1997 | Klaveness et al. ......... 424/9.52 |
| 5,620,689 A | 4/1997 | Allen et al. ................ 424/178.1 |
| 5,626,833 A | 5/1997 | Schutt et al. ............... 424/9.52 |
| 5,633,226 A | 5/1997 | Owen et al. .................... 514/2 |
| 5,639,443 A | 6/1997 | Schutt et al. ............... 424/9.52 |
| 5,639,473 A | 6/1997 | Grinstaff et al. ............ 424/450 |
| 5,643,553 A | 7/1997 | Schneider et al. ......... 424/9.52 |
| 5,648,095 A | 7/1997 | Illum et al. ................. 424/489 |
| 5,648,098 A | 7/1997 | Porter ........................ 424/490 |
| 5,672,585 A | 9/1997 | Pierschbacher et al. ........ 514/11 |
| 5,676,928 A | 10/1997 | Klaveness et al. ......... 424/9.32 |
| 5,679,377 A * | 10/1997 | Bernstein et al. ............ 424/491 |
| 5,679,459 A | 10/1997 | Riess et al. ............... 428/402.2 |
| 5,686,060 A | 11/1997 | Schneider et al. ......... 424/9.52 |
| 5,686,102 A | 11/1997 | Gross et al. ................ 424/9.52 |
| 5,695,460 A | 12/1997 | Siegel et al. .................. 604/21 |
| 5,701,899 A | 12/1997 | Porter .................... 428/662.02 |
| 5,705,187 A * | 1/1998 | Unger ........................ 424/450 |
| 5,707,352 A | 1/1998 | Sekins et al. ................. 604/56 |
| 5,707,606 A | 1/1998 | Quay ........................ 424/9.52 |
| 5,707,607 A | 1/1998 | Quay ........................ 424/9.52 |
| 5,711,933 A | 1/1998 | Bichon et al. .............. 424/9.52 |
| 5,716,597 A | 2/1998 | Lohrmann et al. ........... 424/9.5 |
| 5,732,707 A | 3/1998 | Widder et al. .......... 128/661.08 |
| 5,733,526 A * | 3/1998 | Trevino ...................... 424/9.52 |
| 5,733,527 A | 3/1998 | Schutt ....................... 424/9.52 |
| 5,733,572 A * | 3/1998 | Unger et al. ................. 424/450 |
| 5,736,121 A | 4/1998 | Unger ......................... 424/9.4 |
| 5,740,807 A | 4/1998 | Porter .................... 128/662.02 |
| 5,770,222 A | 6/1998 | Unger et al. ................. 424/450 |
| 5,773,024 A | 6/1998 | Unger et al. ................. 424/9.4 |
| 5,804,162 A | 9/1998 | Kabalnov et al. .......... 424/9.51 |
| 5,830,430 A | 11/1998 | Unger et al. ................ 424/1.21 |
| 5,840,023 A | 11/1998 | Oraevsky et al. ............ 600/407 |
| 5,846,517 A | 12/1998 | Unger ........................ 424/9.52 |
| 5,849,727 A | 12/1998 | Porter et al. ................. 514/156 |
| 5,855,865 A | 1/1999 | Lambert et al. ............ 424/9.52 |
| 5,858,399 A | 1/1999 | Lanza et al. ................. 424/450 |
| 5,874,062 A | 2/1999 | Unger ......................... 424/9.4 |
| 5,897,851 A | 4/1999 | Quay et al. ................. 424/9.52 |
| 5,976,501 A | 11/1999 | Jablonski .................... 424/9.52 |
| 5,989,520 A * | 11/1999 | Lanza et al. ............... 424/9.32 |
| 5,997,898 A | 12/1999 | Unger ........................ 424/450 |
| 6,056,938 A | 5/2000 | Unger et al. ................ 424/1.21 |

FOREIGN PATENT DOCUMENTS

| | | |
|---|---|---|
| EP | 0 052 575 | 5/1982 |
| EP | 0 107 559 | 5/1984 |
| EP | 0 077 752 B1 | 3/1986 |
| EP | 0 243 947 | 4/1987 |
| EP | 0 224 934 A2 | 6/1987 |
| EP | 0 231 091 | 8/1987 |
| EP | 0 272 091 | 6/1988 |
| EP | 0 320 433 A2 | 12/1988 |
| EP | 0 324 938 | 7/1989 |
| EP | 0 338 971 | 10/1989 |
| EP | 357163 A1 | 3/1990 |
| EP | 0 359 246 A2 | 3/1990 |
| EP | 0 361 894 | 4/1990 |
| EP | 0 216 730 | 1/1991 |
| EP | 0 467 031 A2 | 5/1991 |
| EP | 0 357 164 B1 | 10/1991 |
| EP | 0 458 745 A1 | 11/1991 |
| EP | 0 314 764 B1 | 9/1992 |
| EP | 0 554 213 A1 | 8/1993 |
| EP | 0 586 875 | 3/1994 |
| EP | 0 614 656 A1 | 9/1994 |
| EP | 0 633 030 A1 | 1/1995 |
| EP | 0 727 225 A2 | 8/1996 |
| EP | 0 901 793 A1 | 3/1999 |
| FR | 2 700 952 | 6/1994 |
| GB | 1044680 | 10/1966 |
| GB | 2193095 A | 2/1988 |
| JP | 62 286534 | 12/1987 |
| JP | SHO 63-60943 | 3/1988 |
| WO | WO 90/04384 | 5/1960 |
| WO | WO 80/02365 | 11/1980 |
| WO | WO 82/01642 | 5/1982 |
| WO | WO 85/01161 | 3/1985 |
| WO | WO 85/02772 | 7/1985 |
| WO | WO 86/00238 | 1/1986 |
| WO | WO 86/01103 | 2/1986 |
| WO | WO 89/05040 | 6/1989 |
| WO | WO 90/01952 | 3/1990 |
| WO | WO 90/04943 | 5/1990 |
| WO | WO 91/00086 | 1/1991 |
| WO | WO 91/03267 | 3/1991 |
| WO | WO 91/096269 | 7/1991 |
| WO | 441468 A2 | 8/1991 |
| WO | WO 91/12823 | 9/1991 |
| WO | WO 91/15244 | 10/1991 |
| WO | WO 92/05806 | 4/1992 |
| WO | WO 92/10166 | 6/1992 |
| WO | WO 92/15284 | 9/1992 |

| | | |
|---|---|---|
| WO | WO 92/17212 | 10/1992 |
| WO | WO 92/17213 | 10/1992 |
| WO | WO 92/17436 | 10/1992 |
| WO | WO 92/17514 | 10/1992 |
| WO | WO 92/21382 | 10/1992 |
| WO | WO 92/22247 | 12/1992 |
| WO | WO 92/22249 | 12/1992 |
| WO | WO 92/22298 | 12/1992 |
| WO | WO 93/00933 | 1/1993 |
| WO | WO 93/05819 | 1/1993 |
| WO | WO 93/06869 | 4/1993 |
| WO | WO 93/13809 | 7/1993 |
| WO | WO 93/17718 | 9/1993 |
| WO | WO 93/20802 | 10/1993 |
| WO | WO 94/00110 | 1/1994 |
| WO | WO 94/06477 | 3/1994 |
| WO | WO 94/07539 | 4/1994 |
| WO | WO 94/09829 | 5/1994 |
| WO | WO 84/02909 | 8/1994 |
| WO | WO 94/16739 | 8/1994 |
| WO | WO 94/21301 | 9/1994 |
| WO | WO 94/21302 | 9/1994 |
| WO | WO 94/28780 | 12/1994 |
| WO | WO 94/28873 | 12/1994 |
| WO | WO 95/03835 | 2/1995 |
| WO | WO 95/06518 | 3/1995 |
| WO | WO 95/07072 | 3/1995 |
| WO | WO 95/23615 | 9/1995 |
| WO | WO 95/24184 | 9/1995 |
| WO | WO 95/26376 | 10/1995 |
| WO | WO 95/32005 | 11/1995 |
| WO | WO 96/04018 | 2/1996 |
| WO | WO 96/09793 | 4/1996 |
| WO | WO 96/32116 | 8/1996 |
| WO | WO 96/25918 | 10/1996 |
| WO | WO 96/36286 | 11/1996 |
| WO | WO 96/40281 | 12/1996 |
| WO | WO 96/40285 | 12/1996 |
| WO | WO 99/13919 | 3/1999 |
| WO | WO 99/39738 | 8/1999 |
| WO | WO 01/15742 | 3/2001 |

OTHER PUBLICATIONS

Adzamli, K. et al., "Preliminary Evaluation of a Polyethyleneglycol–Stabilized Manganese–Substituted Hydroxylapatite as an intravascular Contrast Agent for MR Angiography", *JMRI*, 1997, 7(1), 204–207.

Bloemberger, N., "Proton Relaxation Times in Paramagnetic Solutions", *J. Chem. Phys.*, 1957, 27(2), 572–573 and 595–596.

Broadhead et al., "The Effect of Process and Formulation Variables on the Properties of Spray–dried β–Galactosidase", *J.Pharm. Pharmocol.*, 1994, 46, 458–467.

Canfield et al., "Incorporation of β–Carotene into Mixed Micelles", *Methods in Enzymology*, 1990, 189, 418–422.

Dyatkin, B.L. et al., "The Perfluoro–t–butyl Anion in the Synthesis of Organofluorine Compounds", *Russian Chem. Rev.*, 1976, 45(7), 607–614 (translated from *Uspekhi khimii*, 1976, 45, 1205).

Elgorab et al., "Solubilization of β–Carotene and Retinol into Aqueous Solutions of Mixed Micelles", *Biochem. Biophys. Acta.*, 1973, 306, 58–66.

Faul et al., "Synthesis of LY333531, an isozyme selective inhibitor of protein kinase C–β", *Abstrs. of papers of the American Chem. Soc.*, Part 2, 1997, *213th ACS National Meeting*, 567.

Fendler et al., *Catalysis in Micellar and Macromolecular Systems*, 1975, Academic Press, New York.

Harmia et al., "Optimization of pilocarpine loading onto nanoparticles by sorption procedures", *Int. J. Pharm.*, 1986, 33, 45–54.

Kaiser et al., "Color Test for Detection of Free Terminal Amino Groups in the Solid–Phase Synthesis of Peptides", *Anal. Biochem.*, 1970, 34, 595–598.

Kawabata, K. et al., "Effect of second–harmonic superimposition on efficient induction of sonochemical effect", *Ultrasonics Sonochemistry*, 1966, 3, 1–5.

Luo, P. et al., "Preparing hydroxyapatite powders with controlled morphology", *Biomaterials*, 1996, 17(20), 1959–1964.

March, J., Advanced Organic Chemistry, 4th ed., John Wiley & Sons, Inc., New York, N.Y., 1992, 417–418.

Matheson Gas Data Book, 1966, Matheson Company, Inc.

Rich et al., "Preparation of a New o–Nitrobenzyl Resin for Solid–Phase Synthesis of tert–Butyloxycarbonyl–Protected Peptide Acids", *J. Am. Chem. Soc.*, 1975, 97(6), 1575–1579.

Shinoda, K., et al., "The Formation of Micelles", *Colloidal Surfactant*, Academic Press, New York, 1963, Chapter 1, 1–96.

Solomon, I., "Relaxation Processes in a System of Two Spins", *Phys. Rev.*, 1955, 99(2), 559–565.

Sutherland et al., "Color Doppler Myocardial Imaging: A New Technique for the Assessment of Myocardial Function", *J. Am. Soc of Echocardiogr*, 1994, 7(5), 441–458.

Olah, G.A. et al., (Eds.), "Nucleophilic Perfluoroalkylation of Organic Compounds Using Perfluoroalkyltrialkylsilanes", *Synthetic Fluorine Chemistry*, John Wiley & Sons, Inc., New York, 1992, 227–245.

Synthesis of Fluoroorganic Compounds, Springer–Verlag, New York, 1985.

Ulendorf, "Physics of Ultrasound Contrast Imaging: Scattering in the Linear Range", *IEEE Transactions on Ultrasonics, Ferroelectrics, and Frequency Control*, 1994, 41(1), 70–79.

Ziefman, Y.V. et al., "The Chemistry of Perfluoroisobutene", *Russion Chem Rev.*, 1984, 53(3), 256–273 (translated from *Uspekhi khimii*, 1984, 53, 431–461).

Hynynen et al., "The Usefulness of a Contrast Agent and Gradient Recalled Acquisition in a Steady–State Imaging Sequence for Magnetic Resonance Imaging–Guided Noninvasive Ultrasound Surgery", *Investigative Radiology*, 1994, 29(10), 897–903.

Porter, T. R., et al., "Thrombolytic Enhancement with Perfluorocarbon–exposed Sonicated Dextrose Albumin Microbubbles", *American Heart Journal*, Nov. 1996, vol. 132, No. 5, pp. 964–968.

Lindner et al., "Myocardial Perfusion Characteristics and Hemodynamic Profile of MRX–115, a Venous Echocardiographic Contrast Agent, During Acute Myocardial Infarction", *J. Am. Soc. Echocardiography*, 1998, 11(1), 36–46.

Regen et al., "Polymerized Phosphatidylcholine Vesicles, Synthesis and Characterization", *J. Am. Chem. Soc.*, 1982, 104(3), 191–195.

Wei et al., "Quantification of Myocardial Blood Flow with Ultrasound–Induced Destruction of Microbubbles Administered as a Constant Venous Infusion", *Circulation*, 1998, 97, 473–483.

Lejbkowicz et al., "The response of normal and malignant cells to ultrasound in vitro", Database *BIOSIS*, No. 1993:95122245 (abstract only).

Jackson et al., "Effect of ultrasound therapy on the repair of Achilles tendon injuries in rats", *Med. Sci. Sports Exercise*, 1991, 23(2), 171–176.

Maxwell, "Therapeutic Ultrasound: Its Effects on the Cellular and Molecular Mechanisms of Inflammation and Repair", *Physiotherapy*, 1992, 78(6), 421–426.

Tuncay et al., "Expression of Genes Associated with Tissue Remodeling Upon Ultrasound Perturbation in the Gingival Fibroblast", *J. Dental Res.*, 1996, 75, 143, (abstract only).

Wang et al., "Low Intensity Ultrasound Treatment Increases Strength in a Rat Femoral Fracture Model", *J. Orthopaedic Res.*, 1994, 12(1), 40–47.

Yang et al., "Exposure to Low–Intensity Ultrasound Increases Aggrecan Gene Expression in a Rat Femur Facture Model", *J. Orthopaedic Res.*, 1996, 14(5), 802–809.

Young et al., "Effect of therapeutic ultrasound on the healing of full–thickness excised skin lesions", *Ultrasonics*, 1990, 28(3), 175–180.

Young et al., "The Effect of Therapeutic Ultrasound on Angiogenesis", *Ultrasound Med. Biol.*, 1990, 16(3), 261–269.

Chortkoff et al., "Pharmacokinetics Do Not Explain the Absence of an Anesthetic Effect of Perfluoropropane or Perfluoropentane." *Anesth. Analg.*, 79, pp. 234–237, 1994.

Ding et al., "Scavenging effect of EDTA–fluorocarbon microspheres on 210 lead," *Chung Kuo Yao Li Hsueh Pao*, 1989 Sep.; 10(5):473–5 (Abstract only).

Hautanen, et al., "Effects of Modifications of the RGD Sequence and Its Context on Recognition by the Fibronectin Receptor*", *The Journal of Biological Chemistry*, vol. 264, No. 3, pp. 1437–1442, Jan. 25, 1999.

P.N.T. Wells, "Pulse–Echo Methods", *Biomedical Ultrasonics*, Academic Press, pp. 209–220 (1977).

Ring et al., "Humanalbuminunverträglichkeit: Klinische und immunologische untersuchungen," *Clinical Weekly*, 52, pp. 595–598 (1974) (English abstract).

Sharma et al., "Emulsification Methods For Perfluorochemicals." *Drug Development And Industrial Pharmacy*, 14 (15–17), pp. 2371–2376 (1988).

Takeuchi et al., "Enhanced Visualization of Intravascular Thrombus with the Use of a Thrombus Targeting Ultrasound Contrast Agent (MRX408): Evidence From in Vivo Experimental Echocardiographic Studies", *The Journal of the American College of Cardiology*, vol. 31, No. 2, Suppl. A, p. 57A, Abstract XP–000952675, Feb. 1998 and *47th Annual Scientific Session of American College of Cardiology*, Atlanta, GA, Mar. 29, 1998–Apr. 1, 1998.

Tilcock et al., "PEG–coated Lipid Vesicles with Encapsulated Technetium–99m as Blood Pool Agents for Nuclear Medicine." *2211b Nuclear Medicine and Biology*, 21, No. 2, pp. 165–170, 1994.

Tilcock et al., "$^{99m}$Tc–labeling of Lipid Vesicles Containing the Lipophilic Chelator PE–DTTA: Effect of Tin–to–chelate Ratio, Chelate Content and Surface Polymer on Labeling Efficiency and Biodistribution Behavior." *2211b Nuclear Medicine and Biology*, 21, No. 1, pp. 89–96, 1994.

Unger, et al., "In Vitro Studies of a New Thrombus–Specific Ultrasound Contrast Agent", *American Journal of Cardiology*, vol. 81, No. 12, Suppl. A, pp. 58G–61G, XP–002087505, Jun. 12, 1998 and *Symposium: Ninth International Congress on Echocardiography: Clinical Cardiology*, 1997.

Wu, et al., "Binding and Lysing of Blood clots Using MRX–408", *Investigative Radiology*, vol. 33, No. 12, pp. 880–885, XP–000952676, Dec. 1998.

Zarif et al., "Synergistic Stabilization of Perfluorocarbon–Pluronic F–68 Emulsion by Perfluoroalkylated Polyhydroxylated Surfactants." *JAOCS*, vol. 66, No. 10, pp. 1515–1523, 1989.

Reexamination of U.S. Patent No. 5,527,521, Reexam Control No. 90/004,719.

Reexamination of U.S. Patent No. 5,547,656, Reexam Control No. 90/004,720.

Fitzpatrick et al., "Metal Ion Catalyzed Decarboxylation: Kinetics and Mechanism of the Oxidative Decarboxylation of Copper (II) Complexes of Aminomalonic Acid in Aqueous Solution", *Inorganic Chemistry*, 1974, 13(3), 568–574.

Thanassi, "Aminomalonic Acid: Spontaneous Decarboxylation and Reaction with 5–Deoxypyridoxal", *Biochemistry*, 1970, 9(3), 525–532.

Stel'mashok et al., "Photolysis of Frozen Solutions of Malonate Complexes", *Koordinatsionnaya khimiya*, 1977, 3(4), 524–527 (Russian and English language versions).

Mayhew et al., "High–Pressure Continuous–Flow System for Drug Entrapment in Liposomes", *Methods in Enzymology*, 1987, 149, 64–77.

Mayhew et al., "Characterization of Liposomes Prepared Using a Microemulsifier", *Biochim. et Biophys. Acta*, 1984, 775, 169–174.

Hope et al., "Production of Large Unilamellar Vesicles by a Rapid Extrusion Procedure: Characterization of Size Distribution, Trapped vol., and Ability to Maintain a Membrane Potential", *Biochim. et Biophys. Acta*, 1985, 812, 55–65.

Mayer et al., "Vesicles of Variable Size Produced by a Rapid Extrusion Procedure", *Biochim. et Biophys. Acta*, 1986, 858, 161–168.

Cheng et al., "The Production and Evaluation of Contrast-Carrying Liposomes Made with an Automatic High Pressure System", *Invest. Radiol.*, 1987, 22, 47–55.

Jain et al., "Facilitated Transport", *Introduction to Biological Membranes*, John Wiley and Sons, N.Y., 1980, Ch. 9, 192–231.

Sigel, H., (ed.), *Metal Ions in Biological Systems: Anti–biotics and Their Complexes*, Marcel Dekker, N.Y., 1985, 19, 1–387.

Nayar et al., "Generation of Large Unilamellar Vesicles From Long–chain Saturated Phosphatidylcholines by Extrusion Technique", *Biochim. et Biophys. Acta*, 1989, 986, 200–206.

Hope et al., "Generation of Multilamellar and Unilamellar Phospholipid Vesicles", *Chem. Phys. Lipids*, 1986, 40, 89–107.

Mattrey et al., "Perfluorochemicals as US Contrast Agents for Tumor–Imaging and Hepatosplenography: Preliminary Clinical Results", *Radiology*, 1987, 163, 339–343.

Mattrey et al., "Perfluoroctylbromide: A Liver/Spleen–Specific and Tumor Imaging Ultrasound Contrast Material", *Radiology*, 1982, 145, 759–762.

Keller et al., "Successful Left Ventricular Opacification Following Peripheral Venous Injection of Sonicated Contrast Agent: An Experimental Evaluation", *LV Contrast Echocardiography*, 1987, 114(3), 570–575.

Feinstein et al., "Two–Dimensional Contrast Echocardiography, I: In Vitro Development and Quantitative Analysis of Echo Contrast Agents", *JACC*, 1984, 3(1), 14–20.

Ten Cate et al., "Two–Dimensional Contrast Echocardiography, II: Transpulmonary Studies", *JACC*, 1984, 3(1), 21–27.

Unger et al., "Hepatic Metastases: Liposomal Gd–DTPA–enhanced MR Imaging", *Radiology*, 1989, 171, 81–85.

Deamer et al., "Permeability of Lipid Bilayers to Water and Ionic Solutes", *Chem. Phys. Lipids*, 1986, 40, 167–188.

Gutknecht et al., "Diffusion of Carbon Dioxide Through Lipid Bilayer Membranes: Effect of Carbonic Anhydrase, Bicarbonate, and Unstirred Layers", *Chemical Abstracts*, 1977, 87, 34772q.

Scarpa et al., "Cation Permeability of Liposomes as a Function of the Chemical Composition of the Lipid Bilayers", *Biochimica et Biophysica Acta*, 1971, 241, 789–797.

MacNaughton et al., "Effects of Gaseous Anesthetics and Inert Gases on the Phase Transition in Smectic Mesophases of Dipalmitoyl Phosphatidylcholine", *Biochim. et Biophys. Acta*, 1980, 597, 193–198.

Tilcock et al., "Liposomal Gd–DTPA: Preparation and Characterization of Relaxivity", *Radiology*, 1989, 171, 77–80.

Mann et al., "Formation of Iron Oxides in Unilamellar Vesicles", *J. Colloid Interface Sci.*, 1988, 122(2), 326–335.

Anderson et al., "Manganese (III) Complexes in Oxidative Decarboxylation of Acids", *J. Am. Chem. Soc.*, 1970, 92(8), 2450–2460.

Muhlradt et al., "Vitamin B6 Analogs: An Improved Synthesis of 5–Deoxypyridoxal", *New Compounds*, 1967, 10, 129–130.

Chapman D., "Physiochemical Properties of Phospholipids and Lipid Water Systems", *Liposome Technology*, Gregoriadis, G., (ed.), CRC Press, Boca Raton, FL, 1984, 1, 1–18.

Violante et al., "Particulate Suspensions as Ultrasonic Contrast Agents for Liver and Spleen", *Inv. Rad.*, 1988, 23, S294–S297.

Fritzsch et al., "Preclinical and Clinical Results with an Ultrasonic Contrast Agent", *Inv. Rad.*, 1988, 23, S302–S305.

Brochure, *Experience*, Sonicator™, Heat Systems–Ultrasonics, Inc., 1987, 3 pages.

Ostro, M. (ed.), "Liposomes", Marcel Dekker, Inc., New York, 1983, 102–103.

Fukuda et al., "Polymer–Encased Vesicles Derived from Diotadecyldimethylammonium Methacrylate", *J. Am. Chem. Soc.*, 1986, 108, 2321–2327.

Regen, "Polymerized Vesicles", *J. Am. Chem. Soc.*, 1980, 102, 6638–6640.

Rose, A. et al., (eds.), "The Condensed Chemical Dictionary", Seventh Edition, Reinhold Publishing Corporation, New York, 1966, 728 and 743.

Belykh, A.G., "Effect of Radiographic Contrast Agents on the Structure and Function of Hepatocyte Plasma Membranes", *Farmakol Toksikol. (MOSC)*, 1981, 44(3), 322–326 (abstract).

Vion–Dury, J. et al., "Liposome–Mediated Delivery of Gadolinium Diethylenetriaminepentaacetic Acid to Hepatic Cells a Phosphorus–31 NMR Study", *J. Pharmacol. Exper. Ther.*, 1989, 250(3), 1113–1118 (abstract).

Zalutsky, M.R. et al., "Characterization of Liposomes Containing Iodine–125–Labeled Radiographic Contrast Agents", *Invest. Radiol.*, 1987, 22(2), 141–147 (abstract).

Crowe et al., "Preservation of Freeze–Dried Liposomes by Trehalose", *Archives Biochem. Biophys.*, 1985, 242(1), 240–247.

Crowe et al., "Preservation of Structural and Functional Activity in Lyophilized Sarcoplasmic Reticulum", *Archives Biochem. Biophys.*, 1983, 220(2) 477–484.

Dorland's Illustrated Medical Dictionary, 27th Edition, W.B. Saunders Company, Philadelphia, 1988, 946.

Gregoriadis, G., (Ed.), "Preparation of Liposomes", *Liposome Technology*, vol. I, CRC Press, Inc., Boca Raton, FL, 1984, 1–18, 30–35, 51–65 and 79–107.

Madden et al., "The accumulation of drugs within large unilamellar vesicles exhibiting a proton gradient: a survey", *Chem. Phys. Lipids*, 1990, 53, 37–46.

Sinkula et al., "Rationale for Design of Biologically Reversible Drug Derivatives: Prodrugs", *J. Pharm. Sci.*, 1975, 64 181–210.

Shiina et al., "Hyperthermiably Low–frequency Synthesized Ultrasound", *IEEE Engineering*, 1988, 2, 879–880 (abstract).

McAvoy et al., "Ultrasonics Symposium Proceedings", *IEEE Engineering*, 1989, 2, 677–1248 (abstract).

Chapman et al., "Biomembrane Phase Transitions", *J. Biol. Chem.*, 1974, 249(8), 2512–2521.

Hug et al., "Liposomes for the Transformation of Eukaryotic Cells", *Biochim. et Biophys. Acta*, 1991, 1097, 1–17.

Marsh, *CRC Handbook of Lipid Bilayers*, CRC Press, Boca Raton, FL, 1990, 139–141.

Szoka et al., "Procedure for preparation of liposomes with large internal aqueous space and high capture by reverse–phase evaportion", *Proc. Natl. Acad. Sci. USA*, 1978, 75(9), 4194–4198.

Acoustic Imaging; AI5200; Convex Curved Linear Array Ultrasound Transducers Operator's Manual, Nov. 20, 1989, 4700–0003–1C, p. 4.

Bangham et al., "Diffusion of Univalent Ions across the Lamellae of Swollen Phospholipids", *J. Mol. Biol.*, 1965, 13, 238–252.

Carson et al., "Ultrasonic Power and Intensities Produced by Diagnostic Ultrasound Equipment", *Ultrasound Med. & Biol.*, 1978, 3, 341–350.

Kost et al., "Ultrasonic Modulated Drug Delivery Systems", *Polymers in Medicine II: Biomedical and Pharmaceutical Applications*, Chiellini et al. (Eds.), Plenum Press, New York and London, 1985, 387–396.

deGier et al., "Relations Between Liposomes and Biomembranes", *Annals New York Acad. Sci.*, 1978, 308, 85–99.

Felgner et al., "Lipofection: A highly efficient, lipid–mediated DNA–transfection procedure", *Proc. Natl. Acad. Sci. USA*, 1987, 84, 7413–7417.

Gabizon et al., "Liposome formulations with prolonged circulation time in blood and enhanced uptake by tumors", *Proc. Natl. Acad. Sci. USA*, 1988, 85, 6949–6953.

Garelli et al., "Incorporation of new amphiphilic perfluoroalkylated bipyridine platinum and palladium complexes into liposomes: stability and structure–incorporation relationships", *Biochim. et Biophys. Acta*, 1992, 1127, 41–48.

Kawai et al., "New Procedure for DNA Transfection with Polycation and Dimethyl Sulfoxide", *Mol. Cell. Biol.*, 1984, 4(6), 1172–1174.

Kuo et al., "Metallocene Antitumor Agents. Solution and Solid–State Molybdenocene Coordination Chemistry of DNA Constituents", *J. Am. Chem. Soc.*, 1991, 113, 9027–9045.

MacDonald, "Genetic engineering of animal cells", *Mammalian Cell Biotechnology: A Practical Approach*, M. Butler (Ed.), Oxford University Press, New York, 1991, 57–70.

Mathiowitz et al., "Photochemical Rupture of Microcapsules: A Model System", *J. Applied Poly. Sci.*, 1981, 26, 809–822.

May et al., "Cationic Liposomes Enable Bovine Herpesvirus Type 2 DNA to Infect Cells", *Acta virol.*, 1991, 35, 107.

Poznansky et al., "Biological Approaches to the Controlled Delivery of Drugs: A Critical Review", *Pharmacol. Rev.*, 1984, 36(4), 277–336.

Sato et al., "Recent Aspects in the Use of Liposomes in Biotechnology and Medicine", *Prog. Lipid Res.*, 1992, 31(4), 345–372.

Simons et al., "Antisense c–myb oligonucleotides inhibit intimal arterial smooth muscle cell accumulation in vivo", *Nature*, 1992, 359, 67–70.

Thompson, L., "At Age 2, Gene Therapy Enters a Growth Phase", *Science*, 1992, 258, 744–746.

Trubetskoy et al. "Cationic liposomes enhance targeted delivery and expression of exogenous DNA medidated by N–terminal modified poly(L–lysine) –antibody conjugate in mouse lung endothelial cells", Biochim. et Biophys. Acta, 1992, 1131, 311–313.

Umemura et al., "Studies on Sonodynamic Cancer Therapy", *IEEE*, 1992, 354–355.

Williams, "Human Gene Therapy: Searching for Better Vectors", *ASM News*, 1992, 58(2), 67–69.

Woodle et al., "Versatility in lipid compositions showing prolonged circulation with sterically stabilized liposomes", *Biochim. et Biophys. Acta*, 1992, 1105, 193–200.

Zhou et al., "Targeted delivery of DNA by liposomes and polymers", *J. Control. Release*, 1992, 19, 269–274.

Mathiowitz et al., "Polyanhydride Microspheres as Drug Carriers", *J. Appl. Poly. Sci.*, 1988, 35, 755–774.

Sankaram et al., "Cholesterol–Induced Fluid–Phase Immiscibility in Membranes", *Proc. Natl. Acad. Sci. USA*, 1991, 88, 8686–8690.

*Scientific Apparatus Catalog 92/93*, VWR Scientific, "Syringes", 1511–1513; "Filtration, Syringe Filters", 766–768; "Filtration, Membranes", 750–753; "Filtration, Filter Holders", 744, 1991.

Gramiak et al., "Detection of Intracardiac Blood Flow by Pulsed Echo–Ranging", *Radiology*, 1971, 415–418.

Feigenbaum et al., "Identification of Ultrasound Echoes from the Left Ventricle by Use of Intracardiac Injections of Indocyanine Green", *Circulation*, 1970, vol. XL1, 615–621.

Santaella et al., "Extended In Vivo Blood Circulation Time of Fluorinated Liposomes", *FEBS 13463*, 1993, 336(3), 481–484.

Brown et al., "Transdermal Delivery of Drugs", *Ann. Rev. Med.*, 1988, 39, 221–229.

Moseley, et al., "Microbubbles: A Novel MR Susceptibility Contrast Agent", Napa, California Meeting of the Society for Magnetic Resonance in Medicine, 1991, 1020, Abstract.

Ter–Pogossian et al., "Physical Principles and Instrumentation", *Computed Body Tomography*, Lee et al. (Eds.), Raven Press, New York, 1988, Ch. 1, 1–7.

Aronberg, "Techniques", *Computed Body Tomography*, Lee et al., (Eds.), Raven Press, New York, 1988, Ch. 2, 9–36.

Miller, "Ultrasonic detection of resonant cavitation bubbles in a flow tube by their second–harmonic emissions," *Ultrasonics*, 1981, 217–224.

Dittrich, "Cardiac Muscle Ischemia and Infarction", *The Second Annual International Symposium on Contrast Agents in Diagnostic Ultrasound*, Atlantic City, NJ, May 7, 1996, 3 pages, abstract.

Pantely, "Intravenous Contrast Echocardiography–Tissue Imaging & Quantification of Coronary Blood Flow", *The Second Annual International Symposium on Contrast Agents in Diagnostic Ultrasound*, Atlantic City, NJ, May 7, 1996, 6 pages, abstract.

Schutt et al., "Osmotically Stabilized Microbubble Sonographic Contrast Agents", *Acad. Radiol.*, 1996, 3 (Suppl. 2), S188–S190.

Frézard et al., "Permeability and stability in buffer and in human serum of fluorinated phospholipid–based liposomes", *Biochim. et Biophys. Acta*, 1994, 1192, pp. 61–70.

Frézard et al., "Fluorinated Phospholipid–Based Vesicles as Potential Drug Carriers: Encapsulation/Sustaining of Drugs and Stability in Human Serum", *Art, Cells, Blood Subs., and Immob. Biotech.*, 1994, 22(4), 1403–1408.

Chang et al., "Semipermeable Aqueous Microcapsules", *Canadian J. Phys. Pharm.*, 1966, 44, 115–128.

Chang, "Semipermeable Microcapsules", *Science*, 1964, 146, 524–525.

Deasy, *Microencapsulation and Related Drug Processes*, Marcel Dekkar, Inc., NY, 1983, vol. 20, Chs. 9 and 10, 195–240.

Yeung et al., "Preparation of Microencapsulated Liposomes", *J. Microencapsulation*, 1988, 5(4), 331–337.

Mattrey et al., "Gas Emulsions as Ultrasound Contrast Agents; Preliminary Results in Rabbits and Dogs", *Invest. Radiol.*, 1994, 29(Suppl. 2), S139–S141.

Meltzer et al., "Transmission of Ultrasonic Contrast Through the Lungs", *Ultrasound Med. Biol.*, 1981, 7(4), 377–384.

PR Newswire, Apr. 1, 1986, 1 page.

Swanson et al., "Enhancement Agents for Ultrasound: Fundamentals", *Pharmaceuticals In Medical Imaging*, 1990, Ch. 22, 682–687.

Jacobs, "Intraocular gas measurement using A–scan ultrasound", *Current Eye Research*, 1986, 5(8), 575–578.

Lincoff et al., "Intravitreal Expansion of Perfluorocarbon Bubbles", *Arch. Ophthalmol.*, 1980, 98, 1646.

Lincoff et al., "Intravitreal Longevity of Three Perfluorocarbon Gases", *Arch. Ophthalmol.*, 1980, 98, 1610–1611.

Lincoff et al., "The Perfluorocarbon Gases in the Treatment of Retinal Detachment", *Ophthalmology*, 1983, 90(5), 546–551.

Gardner et al., "A Survey of Intraocular Gas Use in North America", *Arch. Ophthalmol.*, 1988, 106, 1188–1189.

Unger et al., "Liposomal MR Contrast Agents", *J. Liposome Research*, 1994, 4(2), 811–834.

Feinstein, S., "Myocardial Perfusion Imaging: Contrast Echocardiography Today and Tomorrow," *JACC*, 1986, 8(1), 251–253.

Keller et al., "The Behavior of Sonicated Albumin Microbubbles Within the Microcirulation: A Basis for Their Use During Myocardial Contrast Echocardiography", *Circul. Res.*, 1989, 65(2), 458–465.

Lincoff et al., "Perfluoro–n–butane: A Gas for Maximum Duration Retinal Tamponade," *Arch Opthalmology*, 1983, 101, 460–462.

*Remington's Pharmaceutical Sciences*, Hoover (Ed.), Mack Publishing Company, Easton, PA, 1975, pp. 295–298; 736; 1242–1244.

*Handbook of Pharmaceutical Excipients*, "Methylecllulose", American Pharmaceutical Association, Washington, D.C. and The Pharmaceutical Society of Great Britain, London, England, 1986, 181–183.

Barnhart et al., "Characteristics of Albunex™: Air–Filled Microspheres for Echocardiography Contrast Enhancement," *Invest. Radiol.*, 1990, 25, S162–164.

Levene et al., "Characterization of Albunex™," *J. Acoust. Soc. Am.*, 1990, 87(Suppl. 1), 569–570.

Miller et al., "Physiochemical Approaches to the Mode of Action of General Anesthetics," *J. Amer. Soc. Anesthesiol.*, 1972, 36(4), 339–351.

"Properties and Applications of the 'Freon' Fluorocarbons" in DuPont Freon Technical Bulletin B–2, E.I. DuPont de Nemours and Company, Wilmington, DE, 1964, 1–11.

"'Freon' Fluorocarbons: Properties and Applications" in DuPont Technical Bulletin G–1, E.I. DuPont de Nemours and Company, Wilmington, DE, 1987, 1–10.

"Encyclopedia of Polymer Science and Engineering," John Wiley & Sons, New York, 1985, 1, 164–169.

Kroschwitz, J. (Ed.), *Concise Encyclopedia of Polymer Science and Engineering*, John Wiley & Sons, New York, 1990, 12–13.

Wheatley et al., "Contrast Agents for Diagnostic Ultrasound: Development and Evaluation of Polymer–Coated Microbubbles," *Biomaterials*, 1990, 11, 713–717.

Villanueva et al., "Characterization of Spatial Patters of Flow Within the Reperfused Myocardium by Myocardial Contrast Echocardiography", *Circulation*, 1993, 88(6), 2596–2606.

Desir et al., "Assessment of regional myocardial perfusion with myocardial contrast echocardiography in a canine model of varying degrees of coronary stenosis", *Am. Heart J.*, 1994, 127(1), 56–63.

Sekins et al., "Lung Cancer Hyperthermia via Ultrasound and PFC Liquids", *Published in Proceedings of 5th International Symposium on Hyperthermic Oncology*, Kyoto, Japan, Aug. 29–Sep. 3, 1998, 3 pages.

Pietersen, "A New Warning System for Fires of Electrical Origin", *CERN European Organization for Nuclear Research, Health and Safety Division*, Mar. 1977, 1–5.

Nomura et al., "US Contrast Enhancement of Hepatic Tumor with Helium Gas Microbubbles: A Preliminary Report", *Jpn. J. Med. Ultrasonics*, 1991, 18(5), 28–35 (Japanese with English language abstract).

Frézard, F., et al., "Fluorinated phosphatidylcholine–based liposomes: $H^+/Na^+$ permeability, active doxorubicin encapsulation and stability in human serum," *Biochimica et Biophysica Acta 1194*, XP–000990899, 1994, 61–68.

Gross, U., et al., "Phospholipid vesiculated fluorocarbon—promising trend in blood substitutes," *Biomat., Art. Cells & Immob. Biotech.*, XP–000990913, 1992, 20(2–4), 831–833.

Riess, J.G., "Du fluor dans nos artères (!)," *New J. Chem.*, XP000990897, 1995, 19, 891–909 (English Abstract).

Riess, J.G., "Introducing a new element–fluorine–into the liposomal membrane," *J. Liposome Research*, XP 000525914, 1995, 5(3), 413–430.

Santaella, C., et al., "Extended in vivo blood circulation time of fluorinated liposomes," XP–000990861, *FEBS 13463*, XP–000990861, 1993, 336(3), 481–484.

Trevino, L., et al., "Incorporation of a perfluoroalkylalkane ($R_FR_H$) into the phospholipid bilayer of DMPC liposomes results in greater encapsulation stability," *J. Liposome Research*, XP 000457303, 1994, 4(2), 1017–1028.

Zarif, L., et al., "Biodistribution and excretion of a mixed fluorocarbon–hydrocarbon "Dowel" emulsion as determined by $^{19}F$ NMR," XP–00099014, 1994, 22(4), 1193–1198.

Porter, T.R., et al., "Multifold sonicated dilutions of albumin with fifty percent dextrose improve left ventricular contrast videointensity after intravenous injuction in human beings," *J. Am. Soc. Echocardiogr*, XP 000590864, Sep./Oct. 1994, 7(5), 465–471.

Porter, T.R., et al., "Noninvasive identification of acute myocardinal ischemia and reperfusion with contrast ultrasound using intravenous perfluoropropane–exposed sonicated dextrose albumin," *Am. College of Cardiology*, XP 000590865, Jul. 1995, 26(1), 33–40.

Porter, T.R., et al., "Visually discernible myocardial echocardiographic contrast after intravenous injection of sonicated dextrose albumin microbubbles containing high molecular weight, less soluble gases," *Am. College of Cardiology*, Feb. 1995, 25(2), 509–515.

Srinivasan, S.K., et al., "Characterization of binding sites, extent of binding, and drug interactions of oligonucleotides with albumin," *Antisense Res. And Develop.*, 1995, 5, 131–139.

Xie, F., et al., "Acute myocardial ischemia and reperfusion can be visually identified non–invasively with intravenous perfluoropropane–enhanced sonicated dextrose albumin ultrasound contrast," *Circulation*, Oct. 1994, 90(4), Part 2, Abstract 2989, 1 page.

* cited by examiner

NBD-DPPE-Dexamethasone

A = Septum Cap
B = Glass vial
C = Preselected glass
D = Aqueous media
E = Oil with drug

A　　B

ACOUSTICALLY ACTIVE DRUG DELIVERY SYSTEMS

REFERENCE TO RELATED APPLICATIONS

This application claims priority to U.S. provisional application 60/046,379, filed May 13, 1997, incorporated herein by reference in its entirety.

FIELD OF THE INVENTION

The invention relates to novel compositions and methods useful in delivering targeted therapeutics. More particularly, the present invention relates to methods for targeting a region of a patient by administering to the patient compositions having a surfactant and a therapeutic.

BACKGROUND OF THE INVENTION

The ability to move active agents from the locus of administration to an area of activity has provided a continuing challenge to investigators. Providing a stable drug delivery vehicle which both preserves the integrity of the drug and allows for a localized release have escaped these efforts. Eye diseases such as diabetic retinopathy and retinitis pigmentosa are uniquely suited for treatment by non-invasive techniques utilizing the delivery of therapeutics to the site of action. Of the many other diseases where targeted release is important, benign prostatic hyperplasia (BPH) and its pharmacological treatment is also particularly amenable to drug delivery vehicles.

Solubilization of a drug in a surfactant and optionally a carrier, preferably a nonpolar carrier, would serve to optimize delivery of many drugs where polar media are inappropriate. The embodiments of the present invention meet the needs for stable, localized non-polar drug delivery and local drug release.

Microspheres consisting of both hydrophilic and relatively hydrophobic domains or layers are known in the art. In PCT Publication WO95/26376 Coombes et al. discloses a composition with a hydrophilic polymer outer coat and a hydrophobic core polymer, the two layers linked by polyethylene glycol.

Ball milling of nanoparticles is also known as, for example, in the disclosure of Wong, U.S. Pat. No. 5,569,448, wherein sulfated nonionic block copolymers form shells for the sequestration of therapeutic or diagnostic agents. Similarly, other dry powder compositions have been formulated combining nucleic acids with hydrophilic excipients, then drying by lyophilization or spray drying. See, for example, Eljamel, et al. in PCT Publication WO96/32116.

The use of surfactants to stabilize preparations of bioactive molecules is reported in the literature. Not all surfactants or conditions of use, however, enhance sorption or binding of particular drugs to a delivery vehicle. One system was reported in Harmia, et al., *Int. J. Pharm.* 1986 33:45–54. Harmia et al. report that non-ionic surfactants below their critical micelle concentration prior to lyophilization improved sorption of pilocarpine to polymethacrylate.

Another problem to be overcome in the formulation of useful delivery forms for biopolymers relates to denaturation of proteins, especially enzymes. Spray drying, particularly at elevated temperatures and/or pressures selectively denatures some proteins. Broadhead, et al., *J. Pharm. Pharmocol.* 1994 46:458–467, however, reports conditions of spray drying which maintain 70% yields of active β-galactosidase.

Treatment of several diseases would be enhanced with improvements in drug delivery technology. Retinal disease, for example, currently is difficult to treat. No effective treatments are available for the most common diseases. Another ophthalmologic disease, diabetic retinopathy, is a common complication of diabetes. In this disease neovascularization results in a proliferation of blood vessels which destroy the retina. Diabetic retinopathy is treated by medical management of diabetes (better control of blood sugar) and ablating neovascularity with laser photocoagulation.

Macular degeneration is probably the most common cause of blindness afflicting the retina. In this disease there are two predominant forms, neovascularization and primary photoreceptor death. Neovascularization results in a proliferation of vessels which irreversibly damage the retina. Primary photoreceptor cell death is associated with Drusen formation. Drusen formation is believed to represent breakdown products from the photoreceptors. Drusen deposits increase as macular degeneration progresses. Currently, there is no good treatment for macular degeneration.

Veno-occlusive disease is caused by venous thrombosis in the retinal vessels and is diagnosed by retinal hemorrhages. There is no effective treatment for retinal venous occlusive disease.

Accordingly, new and/or better targeted therapeutics, as well as methods of delivering and making the same, are needed. The present invention is directed to these, as well as other important ends.

SUMMARY OF THE INVENTION

The present invention is directed to a targeted therapeutic delivery system comprising a gas or gaseous precursor filled microsphere wherein said gas or gaseous precursor filled microsphere comprises an oil, a surfactant, and a therapeutic compound. Methods of preparing the targeted therapeutic delivery system are also embodied by the present invention. The present invention includes a method comprising processing a solution comprising an oil and a surfactant in the presence of a gaseous precursor, at a temperature below the gel to liquid crystalline phase transition temperature of the surfactant to form gas or gaseous precursor filled microsphere, and adding to said microspheres a therapeutic compound resulting in a targeted therapeutic delivery system, wherein said processing is selected from the group consisting of controlled agitation, controlled drying, and a combination thereof.

Methods of administering the compositions of the present invention are also set forth herein.

These and other aspects of the invention will become more apparent from the following detailed description.

DETAILED DESCRIPTION OF THE INVENTION

Definitions

Figure 1:
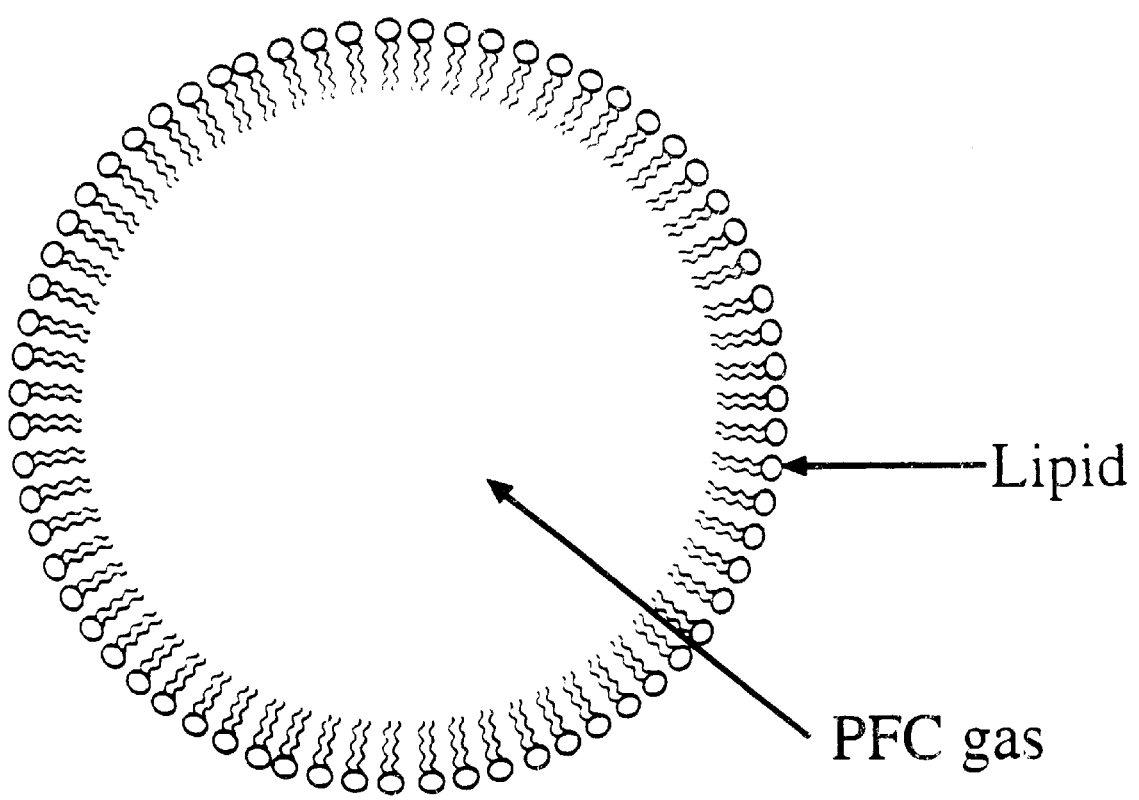
FIG. 1 represents a conventional gas-filled phospholipid microsphere.
Figure 2:
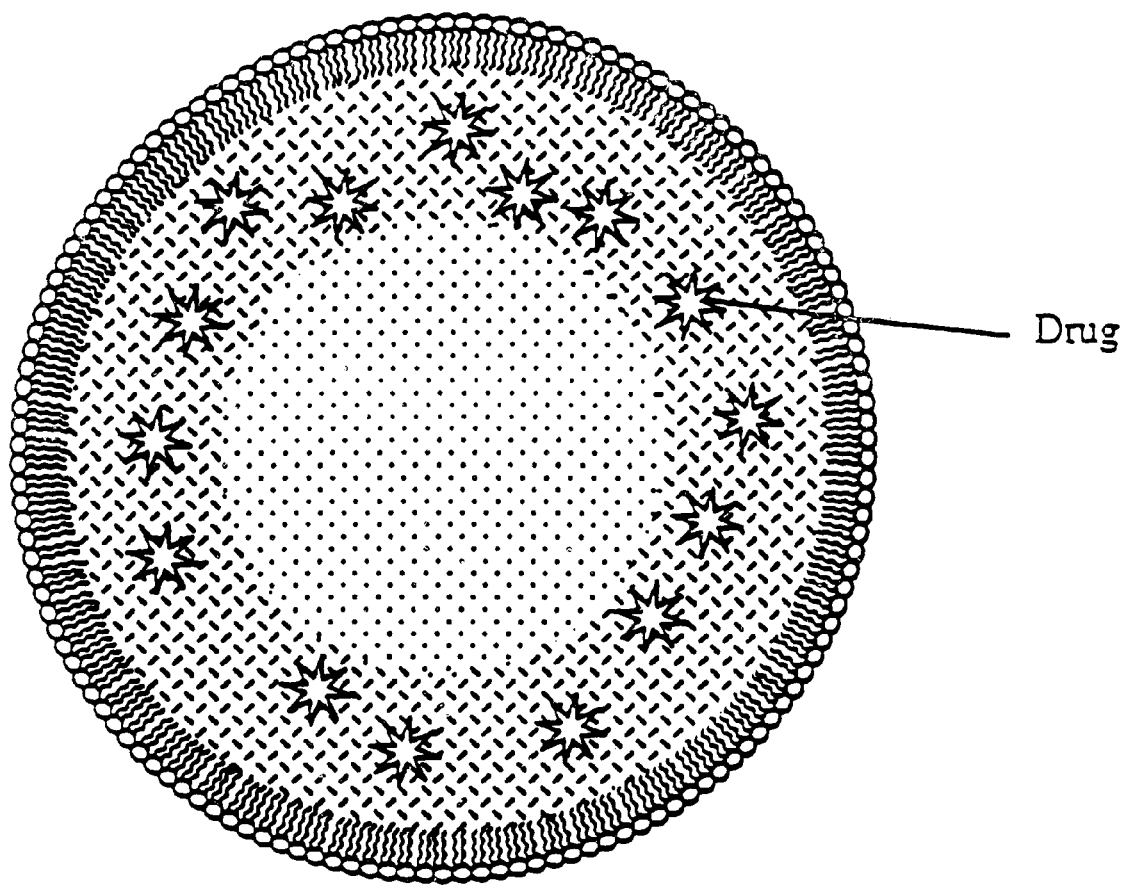
FIG. 2 represents a therapeutic delivery system in accordance with the present invention.

As employed above and throughout the disclosure, the following terms, unless otherwise indicated, shall be understood to have the following meanings.

"Surfactant" or "surface active agent" refer to a substance that alters energy relationship at interfaces, such as, for example, synthetic organic compounds displaying surface activity, including, inter alia, wetting agents, detergents, penetrants, spreaders, dispersing agents, and foaming agents. Preferable examples of surfactants useful in the present invention are hydrophobic compounds, and include phospholipids, oils, and fluorosurfactants.

"Emulsion" refers to a mixture of two or more generally immiscible liquids, and is generally in the form of a colloid. The mixture may be of lipids, for example, which may be homogeneously or heterogeneously dispersed throughout the emulsion. Alternatively, the lipids may be aggregated in the form of, for example, clusters or layers, including monolayers or bilayers.

"Dry" and variations thereof, refer to a physical state that is dehydrated or anhydrous, i.e., substantially lacking liquid. Drying includes for example, spray drying, lyophilization, and vacuum drying.

"Spray drying" refers to drying by bringing an emulsion of surfactant and a therapeutic, or portions thereof, in the form of a spray into contact with a gas, such as air, and recovering in the form of a dried emulsion. A blowing agent, such as methylene chloride, for example, may be stabilized by the surfactant.

"Lyophilize" or freeze drying refers to the preparation of a lipid composition in dry form by rapid freezing and dehydration in the frozen state (sometimes referred to as sublimation). Lyophilization takes place at a temperature which results in the crystallization of the lipids to form a lipid matrix. This process may take place under vacuum at a pressure sufficient to maintain frozen product with the ambient temperature of the containing vessel at about room temperature, preferably less than about 500 mTorr, more preferably less than about 200 mTorr, even more preferably less than about 1 mTorr. Due to the small amount of lipids used to prepare the lipid composition of the present invention, lyophilization is not difficult to conduct. The lipid composition in the present invention is an improvement over conventional microsphere compositions because the amount of lipids are reduced in comparison to the prior art and the lipid composition is formulated to minimize loss due to filtration of large (>0.22 $\mu$m) particulate matter. The latter is particularly important with lipids having a net negative charge (i.e. phosphatidic acid) because their solubility in aqueous-based diluents is marginal.

"Vacuum drying" refers to drying under reduced air pressure resulting in drying at a lower temperature than required at full pressure.

"Ball milling" refers to pulverizing in a hollow, usually cylindrical, drum that contains pebbles of material, such as steel balls, and optionally a liquid, that is revolved or agitated so the pebbles create a crushing action as they roll about the drum.

"Resuspending" refers to adding a liquid to change a dried physical state of a substance to a liquid physical state. For example, a dried therapeutic delivery system may be resuspended in a liquid such that it has similar characteristics in the dried and resuspended states. The liquid may be an aqueous liquid or an organic liquid, for example. In addition, the resuspending medium may be a cryopreservative. Polyethylene glycol, sucrose, glucose, fructose, mannose, trebalose, glycerol, propylene glycol, and sodium chloride may be useful as resuspending medium.

"Carrier" refers to a pharmaceutically acceptable vehicle, which is a nonpolar, hydrophobic solvent, and which may serve as a reconstituting medium. The carrier may be aqueous-based or organic-based. Carriers include, inter alia, lipids, proteins, polysaccharides, sugars, polymers, copolymers, and acrylates.

"Lipid" refers to a naturally-occurring, synthetic or semi-synthetic (i.e., modified natural) compound which is generally amphipathic. The lipids typically comprise a hydrophilic component and a hydrophobic component. Exemplary lipids include, for example, fatty acids, neutral fats, phosphatides, oils, glycolipids, surface-active agents (surfactants), aliphatic alcohols, waxes, terpenes and steroids. The phrase semi-synthetic (or modified natural) denotes a natural compound that has been chemically modified in some fashion.

"Polymer" or "polymeric" refers to molecules formed from the chemical union of two or more repeating units. Accordingly, included within the term "polymer" may be, for example, dimers, trimers and oligomers. The polymer may be synthetic, naturally-occurring or semisynthetic. In a preferred form, "polymer" refers to molecules which comprise 10 or more repeating units.

"Protein" refers to molecules comprising, and preferably consisting essentially of, $\alpha$-amino acids in peptide linkages. Included within the term "protein" are globular proteins such as albumins, globulins and histones, and fibrous proteins such as collagens, elastins and keratins. Also included within the term "protein" are "compound proteins," wherein a protein molecule is united with a nonprotein molecule, such as nucleoproteins, mucoproteins, lipoproteins and metalloproteins. The proteins may be naturally-occurring, synthetic or semi-synthetic.

"Stabilizing material" or "stabilizing compound" refers to any material which is capable of improving the stability of compositions containing the gases, gaseous precursors, steroid prodrugs, targeting ligands and/or other bioactive agents described herein, including, for example, mixtures, suspensions, emulsions, dispersions, vesicles, or the like. Encompassed in the definition of "stabilizing material" are certain of the present bioactive agents. The improved stability involves, for example, the maintenance of a relatively balanced condition, and may be exemplified, for example, by increased resistance of the composition against destruction, decomposition, degradation, and the like. In the case of preferred embodiments involving vesicles filled with gases, gaseous precursors, liquids, steroid prodrugs and/or bioactive agents, the stabilizing compounds may serve to either form the vesicles or stabilize the vesicles, in either way serving to minimize or substantially (including completely) prevent the escape of gases, gaseous precursors, steroid prodrugs and/or bioactive agents from the vesicles until said release is desired. The term "substantially," as used in the present context of preventing escape of gases, gaseous precursors, steroid prodrugs and/or bioactive agents from the vesicles, means greater than about 50% is maintained entrapped in the vesicles until release is desired, and preferably greater than about 60%, more preferably greater than about 70%, even more preferably greater than about 80%, still even more preferably greater than about 90%, is maintained entrapped in the vesicles until release is desired. In particularly preferred embodiments, greater than about 95% of the gases, gaseous precursors, steroid prodrugs and/or bioactive agents are maintained entrapped until release is desired. The gases, gaseous precursors, liquids, steroid prodrugs and/or bioactive agents may also be completely maintained entrapped (i.e., about 100% is maintained entrapped), until release is desired. Exemplary stabilizing materials include, for example, lipids, proteins, polymers, carbohydrates and surfactants. The resulting mixture, suspension, emulsion or the like may comprise walls (i.e., films, membranes and the like) around the steroid prodrug, bioactive agent, gases and/or gaseous precursors, or may be substantially devoid of walls or membranes, if desired. The stabilizing may, if desired, form droplets. The stabilizing material may also comprise salts and/or sugars. In certain embodiments, the stabilizing materials may be substantially (including completely) cross-linked. The stabilizing material may be neutral, positively or negatively charged.

"Droplet" refers to a spherical or spheroidal entity which may be substantially liquid or which may comprise liquid and solid, solid and gas, liquid and gas, or liquid, solid and gas. Solid materials within a droplet may be, for example, particles, polymers, lipids, proteins, or surfactants.

"Vesicle" refers to an entity which is generally characterized by the presence of one or more walls or membranes which form one or more internal voids. Vesicles may be formulated, for example, from a stabilizing material such as a lipid, including the various lipids described herein, a proteinaceous material, including the various proteins described herein, and a polymeric material, including the various polymeric materials described herein. As discussed herein, vesicles may also be formulated from carbohydrates, surfactants, and other stabilizing materials, as desired. The lipids, proteins, polymers and/or other vesicle forming stabilizing materials may be natural, synthetic or semi-synthetic. Preferred vesicles are those which comprise walls or membranes formulated from lipids. The walls or membranes may be concentric or otherwise. The stabilizing compounds may be in the form of one or more monolayers or bilayers. In the case of more than one monolayer or bilayer, the monolayers or bilayers may be concentric. Stabilizing compounds may be used to form a unilamellar vesicle (comprised of one monolayer or bilayer), an oligolamellar vesicle (comprised of about two or about three monolayers or bilayers) or a multilamellar vesicle (comprised of more than about three monolayers or bilayers). The walls or membranes of vesicles may be substantially solid (uniform), or they may be porous or semi-porous. The vesicles described herein include such entities commonly referred to as, for example, liposomes, liposhperes, particles, nanoparticles, micelles, bubbles, microbubbles, microspheres, lipid-coated bubbles, polymer-coated bubbles and/or protein-coated bubbles, microbubbles and/or microspheres, nanospheres, microballoons, microcapsules, aerogels, clathrate bound vesicles, hexagonal H II phase structures, and the like. The internal void of the vesicles may be filled with a wide variety of materials including, for example, water, oil, gases, gaseous precursors, liquids, fluorinated liquids, liquid perfluorocarbons, liquid perfluoroethers, therapeutics, and bioactive agents, if desired, and/or other materials. The vesicles may also comprise a targeting ligand, if desired.

"Liposome" refers to a generally spherical or spheroidal cluster or aggregate of amphipathic compounds, including lipid compounds, typically in the form of one or more concentric layers, for example, bilayers. They may also be referred to herein as lipid vesicles. The liposomes may be formulated, for example, from ionic lipids and/or non-ionic lipids. Liposomes formulated from non-ionic lipids may be referred to as niosomes.

"Liposphere" refers to an entity comprising a liquid or solid oil surrounded by one or more walls or membranes.

"Micelle" refers to colloidal entities formulated from lipids. In certain preferred embodiments, the micelles comprise a monolayer, bilayer, or hexagonal H II phase structure.

"Aerogel" refers to generally spherical or spheroidal entities which are characterized by a plurality of small internal voids. The aerogels may be formulated from synthetic materials (for example, a foam prepared from baking resorcinol and formaldehyde), as well as natural materials, such as carbohydrates (polysaccharides) or proteins.

"Clathrate" refers to a solid, semi-porous or porous particle which may be associated with vesicles. In a preferred form, the clathrates may form a cage-like structure containing cavities which comprise one or more vesicles bound to the clathrate, if desired. A stabilizing material may, if desired, be associated with the clathrate to promote the association of the vesicle with the clathrate. Clathrates may be formulated from, for example, porous apatites, such as calcium hydroxyapatite, and precipitates of polymers and metal ions, such as alginic acid precipitated with calcium salts.

Figure 3:
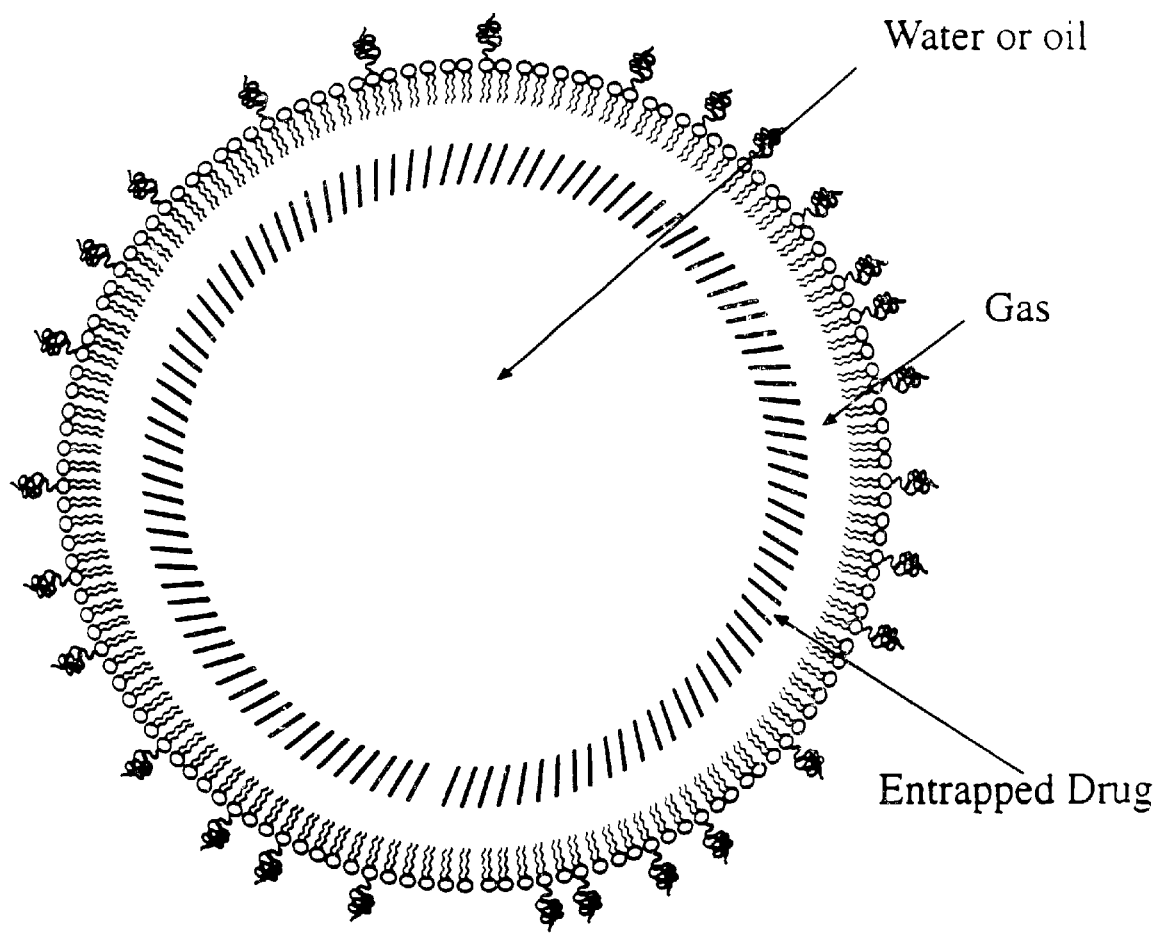
FIG. 3 represents a therapeutic delivery system configuration as an antibubble.
Figure 4:
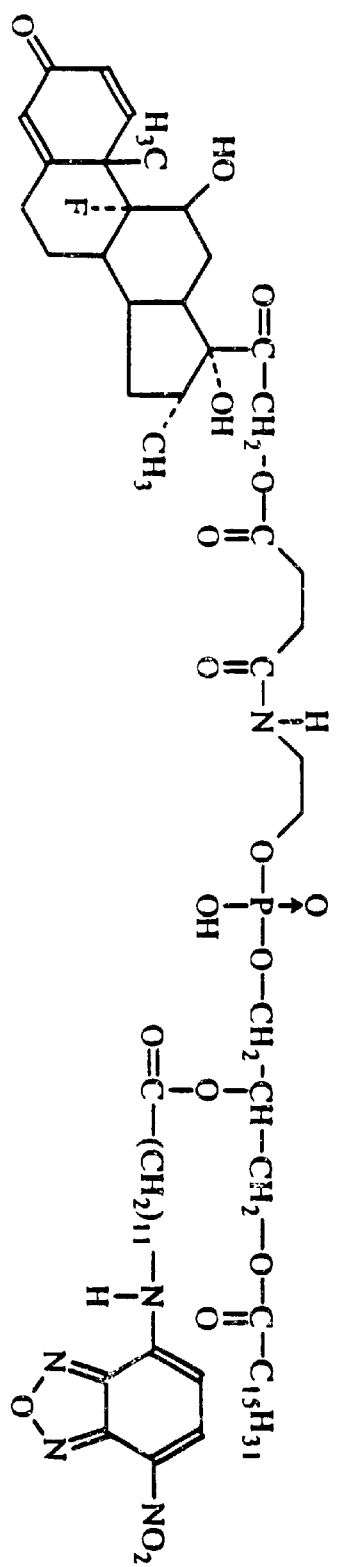
FIG. 4 shows NBD-DPPE-Dexamethasone, a new lipid soluble conjugate suitable for delivery in a therapeutic delivery system.

"Antibubble" refers to a composition having a central sphere of lipid surrounded by a gas, liquid, or gas/liquid mixture, such as, for example, a perfluorocarbon, which in turn is surrounded by a stabilizing material, such as, for example, a surfactant or oil. One or more targeting ligands may be incorporated into the surface of the antibubble as shown in FIG. 3.

"Gas filled vesicle" refers to a vesicle having a gas encapsulated therein. "Gaseous precursor filled vesicle" refers to a vesicle having a gaseous precursor encapsulated therein. The vesicles may be minimally, partially, substantially, or completely filled with the gas and/or gaseous precursor. The term "substantially" as used in reference to the gas and/or gaseous precursor filled vesicles means that greater than about 30% of the internal void of the substantially filled vesicles comprises a gas and/or gaseous precursor. In certain embodiments, greater than about 40% of the internal void of the substantially filled vesicles comprises a gas and/or gaseous precursor, with greater than about 50% being more preferred. More preferably, greater than about 60% of the internal void of the substantially filled vesicles comprises a gas and/or gaseous precursor, with greater than about 70% or 75% being more preferred. Even more preferably, greater than about 80% of the internal void of the substantially filled vesicles comprises a gas and/or gaseous precursor, with greater than about 85% or 90% being still more preferred. In particularly preferred embodiments, greater than about 95% of the internal void of the vesicles comprises a gas and/or gaseous precursor, with about 100% being especially preferred. Alternatively, the vesicles may contain no or substantially no gas or gaseous precursor.

"Suspension" or "dispersion" refers to a mixture, preferably finely divided, of two or more phases (solid, liquid or gas), such as, for example, liquid in liquid, solid in solid, gas in liquid, and the like which preferably can remain stable for extended periods of time.

"Hexagonal H II phase structure" refers to a generally tubular aggregation of lipids in liquid media, for example, aqueous media; in which the hydrophilic portion(s) of the lipids generally face inwardly in association with an aqueous liquid environment inside the tube. The hydrophobic portion(s) of the lipids generally radiate outwardly and the complex assumes the shape of a hexagonal tube. A plurality of tubes is generally packed together in the hexagonal phase structure.

"Patient" refers to animals, including mammals, preferably humans.

"Region of a patient" refers to a particular area or portion of the patient and in some instances to regions throughout the entire patient. Exemplary of such regions are the eye, gastrointestinal region, the cardiovascular region (including myocardial tissue), the renal region as well as other bodily regions, tissues, lymphocytes, receptors, organs and the like, including the vasculature and circulatory system, and as well as diseased tissue, including cancerous tissue, such as the prostate and breast. "Region of a patient" includes, for example, regions to be imaged with diagnostic imaging, regions to be treated with a bioactive agent, regions to be targeted for the delivery of a bioactive agent, and regions of elevated temperature. The "region of a patient" is preferably internal, although, if desired, it may be external. The phrase "vasculature" denotes blood vessels (including arteries, veins and the like). The phrase "gastrointestinal region" includes the region defined by the esophagus, stomach, small and large intestines, and rectum. The phrase "renal region" denotes the region defined by the kidney and the vasculature that leads directly to and from the kidney, and includes the abdominal aorta.

"Region to be targeted" or "targeted region" refer to a region of a patient where delivery of a therapeutic is desired. "Region to be imaged" or "imaging region" denotes a region of a patient where diagnostic imaging is desired.

"Therapeutic" refers to any pharmaceutical, drug or prophylactic agent which may be used in the treatment (including the prevention, diagnosis, alleviation, or cure) of a malady, affliction, disease or injury in a patient. Therapeutic includes contrast agents and dyes for visualization. Therapeutically useful peptides, polypeptides and polynucleotides may be included within the meaning of the term pharmaceutical or drug.

"Genetic material" refers generally to nucleotides and polynucleotides, including deoxyribonucleic acid (DNA) and ribonucleic acid (RNA). The genetic material may be made by synthetic chemical methodology known to one of ordinary skill in the art, or by the use of recombinant technology, or by a combination thereof. The DNA and RNA may optionally comprise unnatural nucleotides and may be single or double stranded. "Genetic material" also refers to sense and anti-sense DNA and RNA, that is, a nucleotide sequence which is complementary to a specific sequence of nucleotides in DNA and/or RNA.

"Bioactive agent" refers to a substance which may be used in connection with an application that is therapeutic or diagnostic, such as, for example, in methods for diagnosing the presence or absence of a disease in a patient and/or methods for the treatment of a disease in a patient. "Bioactive agent" also refers to substances which are capable of exerting a biological effect in vitro and/or in vivo. The bioactive agents may be neutral, positively or negatively charged. Exemplary bioactive agents include, for example, prodrugs, targeting ligands, diagnostic agents, pharmaceutical agents, drugs, synthetic organic molecules, proteins, peptides, vitamins, steroids, steroid analogs and genetic material, including nucleosides, nucleotides and polynucleotides.

"Targeting ligand" refers to any material or substance which may promote targeting of tissues and/or receptors in vivo or tit vitro with the compositions of the present invention. The targeting ligand may be synthetic, semi-synthetic, or naturally-occurring. Materials or substances which may serve as targeting ligands include, for example, proteins, including antibodies, antibody fragments, hormones, hormone analogues, glycoproteins and lectins, peptides, polypeptides, amino acids, sugars, saccharides, including monosaccharides and polysaccharides, carbohydrates, vitamins, steroids, steroid analogs, hormones, cofactors, bioactive agents, and genetic material, including nucleosides, nucleotides, nucleotide acid constructs and polynucleotides.

A "precursor" to a targeting ligand refers to any material or substance which may be converted to a targeting ligand. Such conversion may involve, for example, anchoring a precursor to a targeting ligand. Exemplary targeting precursor moieties include maleimide groups, disulfide groups, such as ortho-pyridyl disulfide, vinylsulfone groups, azide groups, and $\alpha$-iodo acetyl groups.

"Diagnostic agent" refers to any agent which may be used in connection with methods for imaging an internal region of a patient and/or diagnosing the presence or absence of a disease in a patient. Exemplary diagnostic agents include, for example, contrast agents for use in connection with ultrasound imaging, magnetic resonance imaging or computed tomography imaging of a patient. Diagnostic agents may also include any other agents useful in facilitating diagnosis of a disease or other condition in a patient, whether or not imaging methodology is employed.

"Vesicle stability" refers to the ability of vesicles to retain the gas, gaseous precursor and/or other bioactive agents entrapped therein after being exposed, for about one minute, to a pressure of about 100 millimeters (mm) of mercury (Hg). Vesicle stability is measured in percent (%), this being the fraction of the amount of gas which is originally entrapped in the vesicle and which is retained after release of the pressure. Vesicle stability also includes "vesicle resilience" which is the ability of a vesicle to return to its original size after release of the pressure.

"Cross-link," "cross-linked" and "cross-linking" generally refer to the linking of two or more stabilizing materials, including lipid, protein, polymer, carbohydrate, surfactant stabilizing materials and/or bioactive agents, by one ore more bridges. The bridges may be composed of one or more elements, groups, or compounds, and generally serve to join an atom from a first stabilizing material molecule to an atom of a second stabilizing material molecule. The cross-link bridges may involve covalent and/or non-covalent associations. Any of a variety of elements, groups, and/or compounds may form the bridges in the cross-links, and the stabilizing materials may be cross-linked naturally or through synthetic means. For example, cross-linking may occur in nature in material formulated from peptide chains which are joined by disulfide bonds of cystine residues, as in keratins, insulins and other proteins. Alternatively, cross-linking may be effected by suitable chemical modification, such as, for example, by combining a compound, such as a stabilizing material, and a chemical substance that may serve as a cross-linking agent, which may cause to react by, for example, exposure to heat, high-energy radiation, ultrasonic radiation and the like. Examples include cross-linking by sulfur to form disulfide linkages, cross-linking using organic peroxides, cross-linking of unsaturated materials by means of high-energy radiation, cross-linking with dimethylol carbamate, and the like. If desired, the stabilizing compounds and/or bioactive agents may be substantially cross-linked. The term "substantially" means that greater than about 50% of the stabilizing compounds contain cross-linking bridges. If desired, greater than about 60%, 70%, 80%, 90%, 95% or even 100% of the stabilizing compounds contain such cross-linking bridges. Alternatively, the stabilizing materials may be non-cross-linked, i.e., such that greater than about 50% of the stabilizing compounds are devoid of cross-linking bridges, and if desired, greater than about 60%, 70%, 80%, 90%, 95% or even 100% of the stabilizing compounds are devoid of cross-linking bridges.

"Covalent association" refers to an intermolecular association or bond which involves the sharing of electrons in the bonding orbitals of two atoms.

"Non-covalent association" refers to intermolecular interaction among two or more separate molecules which does not involve a covalent bond. Intermolecular interaction is dependent upon a variety of factors, including, for example, the polarity of the involved molecules, and the charge (positive or negative), if any, of the involved molecules. Non-covalent associations are selected from ionic interactions, dipole-dipole interactions, van der Waal's forces, and combinations thereof.

"Ionic interaction" or "electrostatic interaction" refers to intermolecular interaction among two or more molecules, each of which is positively or negatively charged. Thus, for example, "ionic interaction" or "electrostatic interaction" refers to the attraction between a first, positively charged molecule and a second, negatively charged molecule. Ionic or electrostatic interactions include, for example, the attraction between a negatively charged stabilizing material, for example, genetic material, and a positively charged lipid, for example, a cationic lipid, such as lauryltrimethylammonium bromide.

"Dipole-dipole interaction" refers generally to the attraction which can occur among two or more polar molecules. Thus, "dipole-dipole interaction" refers to the attraction of the uncharged, partial positive end of a first polar molecule, commonly designated as $\delta^+$, to the uncharged, partial negative end of a second polar molecule, commonly designated as $\delta^-$. Dipole-dipole interactions are exemplified by the attraction between the electropositive head group, for example, the choline head group, of phosphatidylcholine and an electronegative atom, for example, a heteroatom, such as oxygen, nitrogen or sulphur, which is present in a stabilizing material, such as a polysaccharide. "Dipole-dipole interaction" also refers to intermolecular hydrogen bonding in which a hydrogen atom serves as a bridge between electronegative atoms on separate molecules and in which a hydrogen atom is held to a first molecule by a covalent bond and to a second molecule by electrostatic forces.

"Van der Waal's forces" refers to the attractive forces between non-polar molecules that are accounted for by quantum mechanics. Van der Waal's forces are generally associated with momentary dipole moments which are induced by neighboring molecules and which involve changes in electron distribution.

"Hydrogen bond" refers to an attractive force, or bridge, which may occur between a hydrogen atom which is bonded covalently to an electronegative atom, for example, oxygen, sulfur, or nitrogen, and another electronegative atom. The hydrogen bond may occur between a hydrogen atom in a first molecule and an electronegative atom in a second molecule (intermolecular hydrogen bonding). Also, the hydrogen bond may occur between a hydrogen atom and an electronegative atom which are both contained in a single molecule (intramolecular hydrogen bonding).

"Hydrophobic interaction" refers to molecules or portions of molecules which do not substantially bind with, absorb and/or dissolve in water.

"Hydrophilic interaction" refers to molecules or portions of molecules which may substantially bind with, absorb and/or dissolve in water. This may result in swelling and/or the formation of reversible gels.

"Biocompatible" refers to materials which are generally not injurious to biological functions and which will not result in any degree of unacceptable toxicity, including allergenic responses and disease states.

"In combination with" refers to the incorporation of bioactive agents, steroid prodrugs, and/or targeting ligands, in a composition of the present invention, including emulsions, suspensions and vesicles. The steroid prodrug, bioactive agent and/or targeting ligand can be combined with the therapeutic delivery system and/or stabilizing compositions (including vesicles) in any of a variety of ways. For example, the steroid prodrug, bioactive agent and/or targeting ligand may be associated covalently and/or non-covalently with the delivery system or stabilizing materials. The steroid prodrug, bioactive agent and/or targeting ligand may be entrapped within the internal void(s) of the delivery system or vesicle. The steroid prodrug, bioactive agent and/or targeting ligand may also be integrated within the layer(s) or wall(s) of the delivery system or vesicle, for example, by being interspersed among stabilizing materials which form or are contained within the vesicle layer(s) or wall(s). In addition, it is contemplated that the steroid prodrug, bioactive agent and/or targeting ligand may be located on the surface of a delivery system or vesicle or non-vesicular stabilizing material. The steroid prodrug, bioactive agent and/or targeting ligand may be concurrently entrapped within an internal void of the delivery system or vesicle and/or integrated within the layer(s) or wall(s) of the delivery system or vesicles and/or located on the surface of a delivery system, or vesicle or non-vesicular stabilizing material. In any case, the steroid prodrug, bioactive agent and/or targeting ligand may interact chemically with the walls of the delivery system, vesicles, including, for example, the inner and/or outer surfaces of the delivery system, vesicle and may remain substantially adhered thereto. Such interaction may take the form of, for example, non-covalent association or bonding, ionic interactions, electrostatic interactions, dipole-dipole interactions, hydrogen bonding, van der Waal's forces, covalent association or bonding, cross-linking or any other interaction, as will be readily apparent to one skilled in the art, in view of the present disclosure. In certain embodiments, the interaction may result in the stabilization of the vesicle. The bioactive agent may also interact with the inner or outer surface of the delivery system or vesicle or the non-vesicular stabilizing material in a limited manner. Such limited interaction would permit migration of the bioactive agent, for example, from the surface of a first vesicle to the surface of a second vesicle, or from the surface of a first non-vesicular stabilizing material to a second non-vesicular stabilizing material. Alternatively, such limited interaction may permit migration of the bioactive agent, for example, from within the walls of the delivery system, vesicle and/or non-vesicular stabilizing material to the surface of the delivery system, vesicle and/or non-vesicular stabilizing material, and vice versa, or from inside a vesicle or non-vesicular stabilizing material to within the walls of a vesicle or non-vesicular stabilizing material and vice versa.

"Tissue" refers generally to specialized cells which may perform a particular function. The term "tissue" may refer to an individual cell or a plurality or aggregate of cells, for example, membranes, blood or organs. The term "tissue" also includes reference to an abnormal cell or a plurality of abnormal cells. Exemplary tissues include myocardial tissue, including myocardial cells and cardiomyocites, membranous tissues, including endothelium and epithelium, laminae, connective tissue, including interstitial tissue, and tumors.

"Receptor" refers to a molecular structure within a cell or on the surface of a cell which is generally characterized by the selective binding of a specific substance. Exemplary receptors include cell-surface receptors for peptide hormones, neurotransmitters, antigens, complement fragments, immunoglobulins and cytoplasmic receptors for steroid hormones.

"Intracellular" or "intracellularly" refers to the area within the plasma membrane of a cell, including the protoplasm, cytoplasm and/or nucleoplasm.

"Intracellular delivery" refers to the delivery of a bioactive agent, such as a targeting ligand and/or steroid prodrug, into the area within the plasma membrane of a cell.

"Cell" refers to any one of the minute protoplasmic masses which make up organized tissue, comprising a mass of protoplasm surrounded by a membrane, including nucleated and unnucleated cells and organelles.

"Alkyl" refers to linear, branched or cyclic hydrocarbon groups. Preferably, the alkyl is a linear or branched hydrocarbon group, more preferably a linear hydrocarbon group. Exemplary linear and branched alkyl groups include, for example, methyl, ethyl, n-propyl, i-propyl, n-butyl, t-butyl, n-pentyl, hexyl, heptyl, octyl, nonyl, and decyl groups. Exemplary cyclic hydrocarbon groups (cycloalkyl groups) include, for example, cyclopentyl, cyclohexyl and cycloheptyl groups. "Fluoroalkyl" refers to an alkyl group which is substituted with one or more fluorine atoms, including, for example, fluoroalkyl groups of the formula $CF_3(CF_2)_n(CH_2)_m$—, wherein each of m and n is independently an integer from 0 to about 22. Exemplary fluoroalkyl groups include perfluoromethyl, perfluoroethyl, perfluoropropyl, perfluorobutyl, perfluorocyclobutyl, perfluoropentyl, perfluorohexyl, perfluoroheptyl, perfluorooctyl, perfluorononyl, perfluorodecyl, perfluoroundecyl and perfluorododecyl.

"Acyl" refers to an alkyl-CO— group wherein alkyl is as previously described. Preferred acyl groups comprise alkyl of 1 to about 30 carbon atoms. Exemplary acyl groups include acetyl, propanoyl, 2-methylpropanoyl, butanoyl and palmitoyl. "Fluoroacyl" refers to an acyl group that is substituted with one or more fluorine atoms, up to and including perfluorinated acyl groups.

"Aryl" refers to an aromatic carbocyclic radical containing about 6 to about 10 carbon atoms. The aryl group may be optionally substituted with one or more aryl group substituents which may be the same or different, where "aryl group substituent" includes alkyl, alkenyl, alkynyl, aryl, aralkyl, hydroxy, alkoxy, aryloxy, aralkoxy, carboxy, aroyl, halo, nitro, trihalomethyl, cyano, alkoxycarbonyl, aryloxycarbonyl, aralkoxycarbonyl, acyloxy, acylamino, aroylamino, carbamoyl, alkylcarbamoyl, dialkylcarbamoyl, arylthio, alkylthio, alkylene and —NRR', where R and R' are each independently hydrogen, alkyl, aryl and aralkyl. Exemplary aryl groups include substituted or unsubstituted phenyl and substituted or unsubstituted naphthyl.

"Alkylaryl" refers to alkyl-aryl- groups (e.g., $CH_3$—$(C_6H_4)$—) and aryl-alkyl- groups (e.g., $(C_6H_5)$—$CH_2$—) where aryl and alkyl are as previously described. Exemplary alkylaryl groups include benzyl, phenylethyl and naphthylmethyl. "Fluoroalkylaryl" refers to an aikylaryl group that is substituted with one or more fluorine atoms, up to and including perfluorinated alkylaryl groups.

"Alkylene" refers to a straight or branched bivalent aliphatic hydrocarbon group having from 1 to about 30 carbon atoms. The alkylene group may be straight, branched or cyclic. The alkylene group may be also optionally unsaturated and/or substituted with one or more "alkyl group substituents," including halogen atoms, such as fluorine atoms. There may be optionally inserted along the alkylene group one or more oxygen, sulpihur or substituted or unsubstituted nitrogen atoms, wherein the nitrogen substituent is alkyl as previously described. Exemplary alkylene groups include methylene (—$CH_2$—), ethylene (—$CH_2CH_2$—), propylene (—$(CH_2)$—), cyclohexylene (—$C_6H_{10}$—), —CH=CH—CH=CH—, —CH=CH—$CH_2$—, —$(CF_2)_n(CH_2)_m$—, wherein n is an integer from about 1 to about 22 and m is an integer from 0 to about 22, —$(CH_2)_n$—N(R)—$(CH_2)_m$—, wherein each of m and n is independently an integer from 0 to about 30 and R is hydrogen or alkyl, methylenedioxy (—O—$CH_2$—O—) and ethylenedioxy (—O—$(CH_2)_2$—O—). It is preferred that the alkylene group has about 2 to about 3 carbon atoms.

"Halo," "halide" or "halogen" refers to chlorine, fluorine, bromine or iodine atoms.

The Solvent

The solvent of the present invention may be an aqueous solvent or an organic solvent. The preferable solvent of the present invention is selected from the group consisting of alkylated alcohols, ethers, acetone, alkanes, dimethyl sulfoxide, toluene, cyclic hydrocarbons, benzene, and gaseous precursors. The ethers are selected from the group consisting of methoxylated ethers, alkylated ethers, diether, triethers, oligo ethers, polyethers, cyclic ethers, and crown ethers; the alkylated alcohol may be methanol; and the alkane may be hexane. The solvent may be partially or fully fluorinated.

The solvent is a suspending medium for associating the surfactant with the therapeutic in the preparation of a therapeutic delivery system. The therapeutic is typically only marginally soluble in the solvent.

The solvent useful in the preparation of the present invention may be removed during the processing of the therapeutic delivery system. During spray drying, for example, the solvent, the surfactant, and the therapeutic, may be combined together with a blowing agent into a gaseous stream such that a substantial portion of the solvent is evaporated during spray drying. As a result, a therapeutic delivery system comprising a surfactant and a therapeutic is prepared.

The Oil, Wax, Fat

For purposes of the present invention, "oil", "oils", and variations thereof as used throughout the application, will be understood to include waxes and fats. Preferred oils, waxes and fats are those having melting points under 100° C. Especially preferred are synthetic oils with melting points between −20° C. and 66° C., more preferably those melting less than 60° C., and most preferably those melting less than 42° C. In this aspect, oils and waxes are generally used to dissolve the drugs but may also be used to suspend crystals of dried drugs, e.g., etoposide or bleomycin. Waxes melting at temperatures above 60° C. may also be used, but generally lower melting point waxes are preferred. Many natural oils known in the literature may be useful in the present invention. The melting points of some conventional oils are difficult to determine due to a multicomponent nature which decompose upon state change.

Other commercially-available synthetic oils and surfactants are also suitable to substitute for the oils listed above in accoustically active liposheres. Among these are those listed in U.S. Pat. No. 5,633,226 to Owen, et al., incorporated by reference herein, and include Captex 200 (a composition described in U.S. Pat. No. 5,633,226), Whitepsol H-15 and MYVACET 9–45K. Surfactants which can optionally be included in AALs from the same reference include capmul MCM, Myverol 18–92, Cremophor EL, Centrophase 31, derivatives of polyoxyethylene, and those disclosed in U.S. Pat. No. 5,573,781 of Brown, the disclosures of which are hereby incorporated herein by reference in its entirety.

Examples of oils, waxes and fasts suitable for the microspheres of the invention include, but are not limited, to those listed in the following table:

TABLE 1

MELTING POINTS OF WAXES, FATS AND OILS (° C.)

| | Melting Point | Natural Origin |
|---|---|---|
| Oils/Waxes/Fats | | |
| Jojoba | 11 | |
| Cay-cay | 30 | |
| Woolwax (anhydrous lanolin) | 39.5 | |
| Ucuhuba | 42.5 | |
| Spermaceti | 44 | |
| Hydrogenated Cocoa Oil | 44 | |
| Parrafin | 45–68 | |
| Orange skin | 46 | |
| Bayberry | 47 | |
| Cetyl alchol | 49 | |
| Japanwax | 49–52 | |
| Sorbitol distearate | 50 | |
| Lanette Wax | 50 | |
| Spermafol 52 | 51 | |
| Cetyl palmitate | 52 | |
| Insect wax (Ceroplastes) | 55 | |
| Diglycol stearate | 56.5 | |
| Indian Arjun | 59 | |
| Pliowax | 55.5 | |
| Ponderosa bark | 58 | |
| Chinese tallow tree | 57 | |
| Carbowax stearate | 57 | |
| Cetyl acetamide | 59 | |
| Jasmine floral | 60 | |
| Beeswax | 62 | |
| Saturated Fatty Acids | | |
| Formic | 8.4 | |
| Acetic | 16.6 | |
| Propionic | −22 | |
| Butyric | −8 | Milk fat |
| Valeric | 34.5 | |
| Caproic | −3.4 | Coconut Oil, 0.5% |
| Enanthic | −7.5 | |
| Caprylic | 16.7 | Coconut Oil, 9% |
| Pelargonic | 12.3 | |
| Capric | 31.6 | Coconut Oil, Elm Seed Oil |
| Hendecanoic | 28.5 | |
| Lauric | 44.2 | Coconut Oil, Palm Kernal Oil |
| Tridecanoic | 41.5 | |
| Myristic | 54.4 | Nutmeg Fat |
| Pentadecanoic | 52.3 | |
| Palmitic | 62.9 | Palm Oil, Cottonseed Oil |

TABLE 1-continued

MELTING POINTS OF WAXES, FATS AND OILS (° C.)

| | Melting Point | Natural Origin |
|---|---|---|
| Unsaturated Fatty Acids | | |
| Linderic | 5.3 | Seed Fat |
| Tsuzuic | 18.5 | Seed Fat |
| Palmitoleic | 0.5 | Soybean Oil, Sea Algaes |
| Petroselinic | 30 | Parsley seed oil |
| Oleic | 16.3 | Widely distributed |
| Elaidic | 43.7 | Partially hydrogenated fats |
| Erucic | 33.5 | Mustard Seed Oil |
| Brassidic | 60 | trans Isomer of Erucic |
| Linoleic | −5 | very widely distributed |
| Linolenic | −11 | Linseed oils |
| Santalbic | 42 | seed fat |
| α-Eleostearic | 49 | Tung oil |
| Punicic | 44 | Pomegranite seed oil |
| Synthetic Fats | | |
| Triolein | −4.5 | |
| Trimyristin | 56 | |
| Triacetin | −78 | |
| Tripalmitin | 66 | |
| Tristearin | 55 | |
| Tributyrin | −75 | |
| Glyceryl Monooctanoate | 29 | |
| Glyceryl Monosterate | 57 | |
| Natural Fats | | |
| Beef tallow | 43 | |
| Mutton tallow | 47 | |
| Lard | 41.5 | |
| Butter | 31 | |
| Cacao Butter | 24.5 | |
| Laurel Oil | 33 | |
| Palm Oil | 30 | |
| Cocoa Nut Oil | 24 | |
| Nutmeg Butter | 43.5 | |
| Soybean Oil | −13 (average) | |
| Rapeseed Oil | −6 (average) | |
| Corn Oil | −14 (average) | |
| Castor Oil | −14 (average) | |
| Japanese Anise Oil | −12.5 (average) | |
| Oil of Eucalyptus | −15.5 | |
| Mustard Seed Oil | −12 (average) | |
| Rose Oil | 20 | |
| Almond Oil | −20 | |

The Surfactant

The surfactant of the present invention is preferably hydrophobic, nonionic, and include lipids, such as and not limited to phospholipids and oils, and fluorosurfactants.

Surfactants include, for example, plant oils, such as for example, soybean oil, peanut oil, canola oil, olive oil, safflower oil, corn oil, and mazola oil, cod liver oil, mineral oil, silicone oil, an oil composed of fluorinated triglycerides, all biocompatible oils consisting of saturated, unsaturated, and/or partially hydrogenated fatty acids, silicon-based oils including, inter alia, vinyl-terminated, hydride terminated, siilanol terminated, amino terminated, epoxy terminated, carbinol terminated fluids, and other silicon-based oils such as (1) mercapto-modified silicon fluid and saturated, unsaturated, or aryl-alkyl substituted silicon oils, synthetic oils such as triglycerides composed of saturated and unsaturated chains of $C_{12}$–$C_{24}$ fatty acids, such as for example the glycerol triglyceride ester of oleic acid, terpenes, linolene, squalene, squalamine, or any other oil commonly known to be ingestible which is suitable for use as a stabilizing compound in accordance with the teachings herein. Additional surfactants include lauryltrimethylammnonium bromide (dodecyl-), cetyltrimethylammonium bromide (hexadecyl-), myristyltrimethylammonium bromide (tetradecyl-), alkyldimethylbenzylammonium chloride (where alkyl is $C_{12}$, $C_{14}$ or $C_{16}$,), benzyldimethyldodecylammonium bromide/chloride, benzyldimethyl hexadecylammonium bromide/chloride, benzyldimethyl tetradecylammonium bromide/chloride, cetyldimethylethylammonium bromide/chloride, or cetylpyridinium bromide/chloride. Other surfactants are disclosed, for example, in U.S. application Ser. No. 08/444,754, U.S. application Ser. No. 08/465,868, U.S. Pat. Nos. 4,684,479 (D'Arrigo), and 5,215,680 (D'Arrigo), and 5,562,893 (Lorhmann), the disclosures of each of which are hereby incorporated herein by reference in its entirety.

Fluorinated triglyceride oils may be prepared by reacting a reactive fluorinated species, such as for example, a fluorine gas, with unsaturated triglyceride oils to produce the desired fluorinated triglyceride.

Suitable proteins, or derivatives thereof, for use as surfactants in the present invention include, for example, albumin, hemoglobin, α-1-antitrypsin, α-fetoprotein, collagen, fibrin, aminotransferases, amylase, C-reactive protein, carcinoembryonic antigen, ceruloplasmin, complement, creatine phosphokinase, ferritin, fibrinogen, fibrin, transpeptidase, gastrin, serum globulins, myoglobin, immunoglobulins, lactate dehydrogenase, lipase, lipoproteins, acid phosphatase, alkaline phosphatase, α-1-serum protein fraction, α-2-serum protein fraction, β-protein fraction, γ-protein fraction and γ-glutamyl transferase. Other proteins that may be used in the present invention are described, for example, in U.S. Pat. Nos. 4,572,203, 4,718, 433, 4,774,958, and 4,957,656, the disclosures of which are hereby incorporated herein by reference in their entirety. Other protein-based surfactants, in addition to those described above and in the aforementioned patents, would be apparent to one of ordinary skill in the art, in view of the present disclosure. Polypeptides such as polyglutamic acid and polylysine may also be useful in the present invention.

In addition to surfactants formulated from lipids and/or proteins, embodiments of the present invention may also involve surfatants formulated from polymers which may be of natural, semi-synthetic (modified natural) or synthetic origin. Polymer denotes a compound comprised of two or more repeating monomeric units, and preferably 10 or more repeating monomeric units. Semi-synthetic polymer (or modified natural polymer) denotes a natural polymer that has ben chemically modified in some fashion Examples of suitable natural polymers include naturally occurring polysaccharides, such as, for example, arabinans, fructans, fucans, galactans, galacturonans, glucans, mannans, xylans (such as, for example, inulin), levan, fucoidan carrageenan, galatocarolose, pectic acid, pectins, including amylose, pullulan, glycogen, amylopectin, cellulose, dextran, dextrin, dextrose, glucose, polyglucose, polydextrose, pustulan, chitin, agarose, keratin, chondroitin, dermatan, hyaluronic acid, alginic acid, xanthin gum, starch, such as HETA-starch, and various other natural homopolymer or heteropolymers, such as those containing one or more of the following aldoses, ketoses, acids or amines: erythrose, threose, ribose, arabinose, xylose, lyxose, allose, altrose, glucose, dextrose, mannose, gulose, idose, galactose, talose, erythrulose, ribulose, xylulose, psicose, fructose, sorbose, tagatose, mannitol, sorbitol, lactose, sucrose, trehalose, maltose, cellobiose, glycine, serine, threonine, cysteine, tyrosine, asparagine, glutamine, aspartic acid, glutamic acid, lysine, arginine, histidine, glucuronic acid, gluconic acid, glucaric acid, galacturonic acid, mannuronic acid, glucosamine, galactosamine, and neuraminic acid, and naturally occuring derivatives thereof. Accordingly, suitable polymers include, for example, proteins, such as albumin. Exemplary semi-synthetic polymers include carboxymethylcellulose, hydroxymethylcellulose, hydroxypropylmethylcellulose, methylcellulose, and methoxycellulose. Exemplary synthetic polymers suitable for use in the present invention include polyphosphazenes, polyethylenes (such as, for example, polyethylene glycol (including, for example, the class of compounds referred to as Pluronics®, which are generically known as poloxamers and are commercially available from BASF, Parsippany, N.J.), polyoxyethylene, and polyethylene terephthlate), polypropylenes (such as, for example, polypropylene glycol), polyurethanes (such as, for example, polyvinyl alcohol (PVA), polyvinyl chloride and polyvinylpyrrolidone), polyamides including nylon, polystyrene, polylactic acids, fluorinated hydrocarbon polymers, fluorinated carbon polymers (such as, for example, polytetrafluoroethylene), acrylate, methacrylate, and polymethylmethacrylate, and derivatives thereof. Preferred are biocompatible synthetic polymers or copolymers prepared from monomers, such as acrylic acid, methacrylic acid, ethyleneimine, crotonic acid, acrylamide, ethyl acrylate, methyl methacrylate, 2-hydroxyethyl methacrylate (HEMA), lactic acid, glycolic acid, ε-caprolactone, acrolein, cyanoacrylate, bisphenol A, epichlorhydrin, hydroxyalkylacrylates, siloxane, dimethylsiloxane, ethylene oxide, ethylene glycol, hydroxyalkyl-methacrylates, N-substituted acrylamides, N-substituted methacrylamides, N-vinyl-2-pyrrolidone, 2,4-pentadiene-1-ol, vinyl acetate, acrylonitrile, styrene, p-amino-styrene, p-amino-benzylstyrene, sodium styrene sulfonate, sodium 2-sulfoxyethylmethacrylate, vinyl pyridine, aminoethyl methacrylates, 2-methacryloyloxy-trimethylammonium chloride, and polyvinylidene, as well polyfunctional crosslinking monomers such as N,N'-methylenebisacrylamide, ethylene glycol dimethacrylates, 2,2'-(p-phenylenedioxy)-diethyl dimethacrylate, divinylbenzene, triallylamine, polylactidecoglycolide, polyethylene-polypropyleneglycol, and methylenebis-(4-phenylisocyanate), including combinations thereof. Preferable polymers include polyacrylic acid, polyetyleneimine, polymethacrylic acid, polymethylmethacrylate, polysiloxane, polydimethylsiloxane, polylactic acid, poly(ε-caprolactone), epoxy resin, poly(ethylene oxide), poly(ethylene glycol), and polyamide (nylon) polymers. Preferable copolymers include the following: polyvinylidene-polyacrylonitrile, polyvinylidene-polyacrylonitrile-polymethylmethacrylate, polystyrene-polyacrylonitrile and poly d-1, lactide co-glycolide polymers. A preferred copolymer is polyvinylidene-polyacrylonitrile. Other suitable biocompatible monomers and polymers will be apparent to those skilled in the art, in view of the present disclosure.

Surfactants may be prepared from other materials, provided that they meet the stability and other criteria set forth herein. Additional synthetic organic monomeric repeating units which can be used to form polymers suitable for shell materials within the present invention are hydroxyacids, lactones, lactides, glycolides, acryl containing compounds, aminotriazol, orthoesters, anhydrides, ester imides, imides, acetals, urethanes, vinyl alcohols, enolketones, and organosiloxanes.

The introduction of fluorine into the shell material can be accomplished by any known method. For example, the introduction of perfluoro-t-butyl moieties is described in U.S. Pat. No. 5,234,680; SYNTHESIS OF FLUOROORGANIC COMPOUNDS (Springer-Vertag, New York, 1985); Zeifman, Y. V. et al., Uspekhi Khimii (1984) 53 p. 431; and Dyatkin, B. L. et al., Uspekhi Khimii (1976) 45, p. 1205, the disclosures of which are hereby incorporated herein by reference in their entirety. These methods generally involve the reaction of perfluoroalkyl carbanions with host molecules as follows:

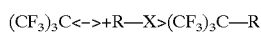

$(CF_3)_3C\text{<->}+R\text{—}X\text{>}(CF_3)_3C\text{—}R$ where R is a host molecule and X is a good leaving group, such as Br, Cl, I or a sulfonato group. After adding a leaving group to the foregoing monomeric shell materials using methods well known in the art, perfluoro-t-butyl moieties can then be easily introduced to these derivatized shell materials (the host molecules) in the manner described above.

Additional methods are known for the introduction of trifluoromethyl groups into various organic compounds. One such method describes the introduction of trifluoromethyl groups by nucleophilic perfluoroalkylation using perfluoroalkyl-trialkylsilanes. (SYNTHETIC FLUORINE CHEMISTRY pp. 227–245 (John Wiley & Sons, Inc., New York, 1992) the disclosures of which are hereby incorporated herein by reference in their entirety).

Fluorine can be introduced into any of the aforementioned materials either in their monomeric or polymeric form. Preferably, fluorine moieties are introduced into monomers, such as fatty acids, amino acids or polymerizable synthetic organic compounds, which are then polymerized for subsequent use as microsphere shell-forming material.

The introduction of fluorine into the surfactant may also be accomplished by forming microspheres in the presence of a perfluorocarbon gas. For example, when microspheres are formed from proteins such as human serum albumin in the presence of a perfluorocarbon gas, such as perfluoropropane, using mechanical cavitation, fluorine from the gas phase becomes bound to the protein shell during formation. The presence of fluorine in the shell material can be later detected by NMR of shell debris which has been purified from disrupted microspheres. Fluorine can also be introduced into microsphere shell material using other methods for forming microspheres, such as sonication, spray-drying or emulsification techniques.

Another way in which fluorine can be introduced is by using a fluorine-containing reactive compound. The term "reactive compound" refers to compounds which are capable of interacting with the surfactant in such a manner that fluorine moieties become covalently attached to thereto. When the surfactant is a protein, preferred reactive compounds are either alkyl esters or acyl halides which are capable of reacting with the protein's amino groups to form an amide linkage via an acylation reaction (see ADVANCED ORGANIC CHEMISTRY pp. 417–418 (John Wiley & Sons, New York, N.Y., 4th ed., 1992) the disclosures of which are hereby incorporated herein by reference in their entirety). The reactive compound can be introduced at any stage during microsphere formation, but is preferably added to the gas phase prior to microsphere formation. For example, when microspheres are to be made using mechanical or ultrasound cavitation techniques, the reactive compound can be added to the gas phase by bubbling the gas to be used in the formation of the microspheres (starting gas) through a solution of the reactive compound. This solution is kept at a constant temperature which is sufficient to introduce a desired amount of reactive compound into the gas phase. The resultant gas mixture, which now contains the starting gas and the reactive compound, is then used to form microspheres. The microspheres are preferably formed by sonication of human serum albumin in the presence of the gas mixture as described in U.S. Pat. No. 4,957,656, the disclosures of which are hereby incorporated herein by reference in their entirety.

Suitable fluorine-containing alkyl esters and acyl halides are provided in

TABLE 2

| REACTIVE COMPOUND | BOILING POINT* (° C.) |
|---|---|
| ALKYL ESTERS | |
| diethyl hexafluoroglutarate | 75 (at 3 mm Hg) |
| diethyl tetrafluorosuccinate | 78 (at 5 mm Hg) |
| methyl heptafluorobutyrate | 95 |
| ethyl heptafluorobutyrate | 80 |
| ethyl pentafluoropropionate | 76 |
| methyl pentafluoropropionate | 60 |
| ethyl perfluorooctanoate | 167 |
| methyl perfluorooctanoate | 159 |
| ACYL HALIDES | |
| nonafluoropentanoyl chloride | 70 |
| perfluoropropionyl chloride | 8 |
| hexafluoroglutaryl chloride | 111 |
| heptafluorobutyryl chloride | 38 |

*at 1 atm (760 mm Hg) unless otherwise noted above

In addition to the use of alkyl esters and acid halides described above, it is well known to those skilled in synthetic organic chemistry that many other fluorine-containing reactive compounds can be synthesized, such as aldehydes, isocyanates, isothiocyanates, epoxides, sulfonyl halides, anhydrides, acid halides and alkyl sulfonates, which contain perfluorocarbon moieties ($-CF_3$, $-C_2F_5$, $-C_3F_4$, $-C(CF_3)_3$). These reactive compounds can then be used to introduce fluorine moieties into any of the aforementioned materials by choosing a combination which is appropriate to achieve covalent attachment of the fluorine moiety.

Materials for preparing the surfactants may be basic and fundamental, and may form the primary basis for creating or establishing the gas and gaseous precursor filled vesicles. For example, surfactants and fluorosurfactants may be basic and fundamental materials for preparing vesicles. On the other hand, the materials may be auxiliary, and act as subsidiary or supplementary agents which may enhance the functioning of the basic surfactant, or contribute some desired property in addition to that afforded by the basic surfactant.

It is not always possible to determine whether a given material is a basic or an auxiliary agent, since the functioning of the material is determined empirically, for example, by the results produced with respect to producing surfactants. As an example of how the basic and auxiliary materials may function, it has been observed that the simple combination of a biocompatible lipid and water or saline when shaken will often give a cloudy solution subsequent to autoclaving for sterilization. Such a cloudy solution may function as a contrast agent, but is aesthetically objectionable and may imply instability in the form of undissolved or undispersed lipid particles. Cloudy solutions may also be undesirable where the undissolved particulate matter has a diameter of greater than about 7 $\mu$m, and especially greater than about 10 $\mu$m. Manufacturing steps, such as sterile filtration, may also be problematic with solutions which contain undissolved particulate matter. Thus, propylene glycol may be added to remove this cloudiness by facilitating dispersion or dissolution of the lipid particles. Propylene glycol may also function as a wetting agent which can improve vesicle formation and stabilization by increasing the surface tension on the vesicle membrane or skin. It is possible that propylene glycol can also function as an additional layer that may coat the membrane or skin of the vesicle, thus providing additional stabilization. Compounds used to make mixed micelle systems also may be used as basic or auxiliary stabilizing materials. Clathrates may also be useful in the preparation of surfactants for use in the present invention, see for example WO 90/01952, the disclosure of which is incorporated herein by reference in its entirety.

It may be possible to enhance the stability of surfactants by incorporating in the surfactants at least a minor amount, for example, about 1 to about 10 mole percent, based on the total amount of lipid employed, of a negatively charged lipid. Suitable negatively charged lipids include, for example, phosphatidylserine, phosphatidic acid, and fatty acids. Without intending to be bound by any theory or theories of operation, it is contemplated that such negatively charged lipids provide added stability by counteracting the tendency of vesicles to rupture by fusing together. Thus, the negatively charged lipids may act to establish a uniform negatively charged layer on the outer surface of the vesicle, which will be repulsed by a similarly charged outer layer on other vesicles which are proximate thereto. In this way, the vesicles may be less prone to come into touching proximity with each other, which may lead to a rupture of the membrane or skin of the respective vesicles and consolidation of the contacting vesicles into a single, larger vesicle. A continuation of this process of consolidation will, of course, lead to significant degradation of the vesicles.

The lipids used, especially in connection with vesicles, are preferably flexible. This means, in the context of the present invention, that the vesicles can alter their shape, for example, to pass through an opening having a diameter that is smaller than the diameter of the vesicle.

The stability of vesicles may be attributable, at least in part, to the materials from which the vesicles are made, including, for example, the lipids, polymers, proteins and/or surfactants described above, and it is often not necessary to employ additional stabilizing materials, although it is optional and may be preferred to do so. In addition to, or instead of, the lipid, protein and/or polymer compounds discussed above, the compositions described herein may comprise one or more other stabilizing materials. Exemplary stabilizing materials include, for example, surfactants and biocompatible polymers. The stabilizing materials may be employed to desirably assist in the formation of vesicles and/or to assure substantial encapsulation of the gases, gaseous precursors and/or therapeutic. Even for relatively insoluble, non-diffusible gases, such as perfluoropropane or sulfur hexafluoride, improved vesicle compositions may be obtained when one or more stabilizing materials are utilized in the formation of the gas and/or gaseous precursor filled vesicles. These compounds may help improve the stability and the integrity of the vesicles with regard to their size, shape and/or other attributes.

Like the polymers discussed above, the biocompatible polymers useful as stabilizing materials for preparing the gas and/or gaseous precursor filled vesicles may be of natural, semi-synthetic (modified natural) or synthetic origin. Exemplary natural polymers include naturally occurring polysaccharides, such as, for example, arabinans, fructans, fucans, galactans, galacturonans, glucans, mannans, xylans (such as, for example, inulin), levan, fucoidan, carrageenan, galatocarolose, pectic acid, pectins, including amylose, pullulan, glycogen, amylopectin, cellulose, dextran, dextrin, dextrose, glucose, polyglucose, polydextrose, pustulan, chitin, agarose, keratin, chondroitin, dermatan, hyaluronic acid, alginic acid, xanthan gum, starch and various other natural homopolymer or heteropolymers, such as those containing one or more of the following aldoses, ketoses, acids or amines: erythrose, threose, ribose, arabinose, xylose, lyxose, allose, altrose, glucose, dextrose, mannose, gulose, idose, galactose, talose, erythrulose, ribulose, xylulose, psicose, fructose, sorbose, tagatose, mannitol, sorbitol, lactose, sucrose, trehalose, maltose, cellobiose, glycine, serine, threonine, cysteine, tyrosine, asparagine, glutamine, aspartic acid, glutamic acid, lysine, arginine, histidine, glucuronic acid, gluconic acid, glucaric acid, galacturonic acid, mannuronic acid, glucosamine, galactosamine, and neuraminic acid, and naturally occurring derivatives thereof. Accordingly, suitable polymers include, for example, proteins, such as albumin. Exemplary semi-synthetic polymers include carboxymethylcellulose, hydroxymethylcellulose, hydroxypropylmethylcellulose, methylcellulose, and methoxycellulose. Exemplary synthetic polymers include polyphosphazenes, polyethylenes (such as, for example, polyethylene glycol (including the class of compounds referred to as Pluronics®, commercially available from BASF, Parsippany, N.J.), polyoxyethylene, and polyethylene terephthlate), polypropylenes (such as, for example, polypropylene glycol), polyurethanes (such as, for example, polyvinyl alcohol (PVA), polyvinyl chloride and polyvinylpyrrolidone), polyamides including nylon, polystyrene, polylactic acids, fluorinated hydrocarbon polymers, fluorinated carbon polymers (such as, for example, polytetrafluoroethylene), acrylate, methacrylate, and polymethylmethacrylate, and derivatives thereof. Methods for the preparation of vesicles which employ polymers as stabilizing compounds will be readily apparent to those skilled in the art, in view of the present disclosure, when coupled with information known in the art, such as that described and referred to in Unger, U.S. Pat. No. 5,205,290, the disclosure of which is hereby incorporated herein by reference in its entirety.

Particularly preferred embodiments of the present invention involve vesicles which comprise three components: (1) a neutral lipid, for example, a nonionic or zwitterionic lipid, (2) a negatively charged lipid, and (3) a lipid bearing a stabilizing material, for example, a hydrophilic polymer. Preferably, the amount of the negatively charged lipid will be greater than about 1 mole percent of the total lipid present, and the amount of lipid bearing a hydrophilic polymer will be greater than about 1 mole percent of the total lipid present. Exemplary and preferred negatively charged lipids include phosphatidic acids. The lipid bearing a hydrophilic polymer will desirably be a lipid covalently linked to the polymer, and the polymer will preferably have a weight average molecular weight of from about 400 to about 100,000. Suitable hydrophilic polymers are preferably selected from the group consisting of polyethylene glycol (PEG), polypropylene glycol, polyvinylalcohol, and polyvinylpyrrolidone and copolymers thereof, with PEG polymers being preferred. Preferably, the PEG polymer has a molecular weight of from about 1000 to about 7500, with molecular weights of from about 2000 to about 5000 being more preferred. The PEG or other polymer may be bound to the lipid, for example, DPPE, through a covalent bond, such as an amide, carbamate or amine linkage. In addition, the PEG or other polymer may be linked to a targeting ligand, or other phospholipids, with a covalent bond including, for example, amide, ester, ether, thioester, thioamide or disulfide bonds. Where the hydrophilic polymer is PEG, a lipid bearing such a polymer will be said to be "pegylated." In preferred form, the lipid bearing a hydrophilic polymer may be DPPE-PEG, including, for example, DPPE-PEG5000, which refers to DPPE having a polyethylene glycol polymer of a mean weight average molecular weight of about 5000 attached thereto (DPPE-PEG5000). Another suitable pegylated lipid is distearoylphosphatidylethanolamine-polyethylene glycol 5000 (DSPE-PEG5000).

In certain preferred embodiments of the present invention, the lipid compositions may include about 77.5 mole % DPPC, 12.5 mole % of DPPA, and 10 mole % of DPPE-PEG5000. Also preferred are compositions which comprise about 80 to about 90 mole % DPPC, about 5 to about 15 mole % DPPA and about 5 to about 15 mole % DPPE-PEG5000. Especially preferred are compositions which comprise DPPC, DPPA and DPPE-PEGS000 in a mole % ratio of 82:10:8, respectively. DPPC is substantially neutral, since the phosphatidyl portion is negatively charged and the choline portion is positively charged. Consequently, DPPA, which is negatively charged, may be added to enhance stabilization in accordance with the mechanism described above. DPPE-PEG provides a pegylated material bound to the lipid membrane or skin of the vesicle by the DPPE moiety, with the PEG moiety free to surround the vesicle membrane or skin, and thereby form a physical barrier to various enzymatic and other endogenous agents in the body whose function is to degrade such foreign materials. The DPPE-PEG may provide more vesicles of a smaller size which are safe and stable to pressure when combined with other lipids, such as DPPC and DPPA, in the given ratios. It is also theorized that the pegylated material, because of its structural similarity to water, may be able to defeat the action of the macrophages of the human immune system, which would otherwise tend to surround and remove the foreign object. The result is an increase in the time during which the stabilized vesicles may function as diagnostic imaging contrast media. A wide variety of targeting ligands may be attached to the free ends of PEG. The PEG typically functions as a spacer and improves targeting.

The terms "stable" or "stabilized" mean that the vesicles may be substantially resistant to degradation, including, for example, loss of vesicle structure or encapsulated gas, gaseous precursor and/or bioactive agent, for a useful period of time. Typically, the vesicles employed in the present invention have a desirable shelf life, often retaining at least about 90% by volume of its original structure for a period of at least about two to three weeks under normal ambient conditions. In preferred form, the vesicles are desirably stable for a period of time of at least about 1 month, more preferably at least about 2 months, even more preferably at least about 6 months, still more preferably about eighteen months, and yet more preferably up to about 3 years. The vesicles described herein, including gas and/or gaseous precursor filled vesicles, may also be stable even under adverse conditions, such as temperatures and pressures which are above or below those experienced under normal ambient conditions.

The gas and/or gaseous precursor filled vesicles used in the present invention may be controlled according to size, solubility and heat stability by choosing from among the various additional or auxiliary stabilizing materials described herein. These materials can affect the parameters of the vesicles, especially vesicles formulated from lipids, not only by their physical interaction with the membranes, but also by their ability to modify the viscosity and surface tension of the surface of the gas and/or gaseous precursor filled vesicle. Accordingly, the gas and/or gaseous precursor filled vesicles used in the present invention may be favorably modified and further stabilized, for example, by the addition of one or more of a wide variety of (i) viscosity modifiers, including, for example, carbohydrates and their phosphorylated and sulfonated derivatives; polyethers, preferably with molecular weight ranges between 400 and 100,000; and di- and trihydroxy alkanes and their polymers, preferably with molecular weight ranges between 200 and 50,000; (ii) emulsifying and/or solubilizing agents including, for example, acacia, cholesterol, diethanolamine, glyceryl monostearate, lanolin alcohols, lecithin, mono- and di-glycerides, mono-ethanolamine, oleic acid, oleyl alcohol, poloxamer, for example, poloxamer 188, poloxamer 184, poloxamer 181, Pluronics® (BASF, Parsippany, N.J.), polyoxyethylene 50 stearate, polyoxyl 35 castor oil, polyoxyl 10 oleyl ether, polyoxyl 20 cetostearyl ether, polyoxyl 40 stearate, polysorbate 20, polysorbate 40, polysorbate 60, polysorbate 80, propylene glycol diacetate, propylene glycol monostearate, sodium lauryl sulfate,- sodium stearate, sorbitan mono-laurate, sorbitan mono-oleate, sorbitan mono-palmitate, sorbitan monostearate, stearic acid, trolamine, and emulsifying wax; (iii) suspending and/or viscosity-increasing agents, including, for example, acacia, agar, alginic acid, aluminum mono-stearate, bentonite, magma, carbomer 934P, carboxymethylcellulose, calcium and sodium and sodium 12, carrageenan, cellulose, dextran, gelatin, guar gum, locust bean gum, veegum, hydroxyethyl cellulose, hydroxypropyl methylcellulose, magnesium-aluminum-silicate, Zeolites®, methylcellulose, pectin, polyethylene oxide, povidone, propylene glycol alginate, silicon dioxide, sodium alginate, tragacanth, xanthan gum, α-d-gluconolactone, glycerol and mannitol; (iv) synthetic suspending agents, such as polyethylene glycol (PEG), polyvinylpyrrolidone (PVP), polyvinylalcohol (PVA), polypropylene glycol (PPG), and polysorbate; and (v) tonicity raising agents which stabilize and add tonicity, including, for example, sorbitol, mannitol, trehalose, sucrose, propylene glycol and glycerol.

The present compositions are desirably formulated in an aqueous environment which can induce the lipid, because of its hydrophobic-hydrophilic nature, to form vesicles, which may be the most stable configuration which can be achieved in such an environment. The diluents which can be employed to create such an aqueous environment include, for example, water, including deionized water or water containing one or more dissolved solutes, such as salts or sugars, which preferably do not interfere with the formation and/or stability of the vesicles or their use as diagnostic agents, such as ultrasound contrast agents, MRI contrast agents, CT contrast agents and optical imaging contrast agents; and normal saline and physiological saline.

Synthetic organic polymers are also suitable for forming microsphere shells. These polymers can consist of a single repeating unit or different repeating units which form a random, alternating or block-type co-polymer. These organic polymers include cross-linked polyelectrolytes such as phosphazenes, imino-substituted polyphosphazenes, polyacrylic acids, polymethacrylic acids, polyvinyl acetates, polyvinyl amines, polyvinyl pyridine, polyvinyl imidazole, and ionic salts thereof. Cross-linking of these polyelectrolytes is accomplished by reaction with multivalent ions of the opposite charge. Further stabilization can be accomplished by adding a polymer of the same charge as the polyelectrolyte. See U.S. Pat. No. 5,149,543 which is incorporated herein by reference. In addition, nonionic surfactants selected from the group consisting of Triton-X® (octoxynols), Tweens® (polyoxyethylene sorbitans), Brij® (polyoxyethylene ethers), Pluronics® (polyethylene glycol), Zonyls® (fluorosurfactants), and Fluorads® may be useful in the present invention.

In certain embodiments, the composition may contain, in whole or in part, a fluorinated compound. Suitable fluorinated compounds include, for example, fluorinated surfactants, including alkyl surfactants, and amphiphilic compounds. A wide variety of such compounds may be employed, including, for example, the class of compounds which are commercially available as ZONYL® fluorosurfactants (the DuPont Company, Wilmington, Del.), including the ZONYL® phosphate salts ($[F(CF_2CF_2)_{3-8}CH_2CH_2O]_{1,2}P(O)(O^-NH_4^+)_{2,1}$) and ZONYL® sulfate salts ($F(CF_2CF_2)_{3-8}$ $CH_2CH_2SCH_2CH_2N^+(CH_3)_3^-$ $OSO_2OCH_3$.), which have terminal phosphate or sulfate groups. Suitable ZONYL® surfactants also include, for example, ZONYL® surfactants identified as Telomer B, including Telomer B surfactants which are pegylated (i.e., have at least one polyethylene glycol group attached thereto), also known as PEG-Telomer B, available from the DuPont Company.

A wide variety of lipids may be suitable for the preparation of compositions of the present invention. The lipids may be of either natural, synthetic or semi-synthetic origin, including for example, fatty acids, neutral fats, phosphatides, oils, glycolipids, surface-active agents (surfactants), aliphatic alcohols, waxes, terpenes and steroids.

Exemplary lipids which may be used to prepare the present invention include, for example, fatty acids, lysolipids, fluorolipids, phosphocholines, such as those associated with platelet activation factors (PAF) (Avanti Polar Lipids, Alabaster, Ala.), including 1-alkyl-2-acetoyl-sn-glycero 3-phosphocholines, and 1-alkyl-2-hydroxy-sn-glycero 3-phosphocholines, which target blood clots; phosphatidylcholine with both saturated and unsaturated lipids, including dioleoylphosphatidylcholine; dimyristoylphosphatidylcholine; dipentadecanoylphosphatidyl-choline; dilauroylphosphatidylcholine; dipalmitoylphosphatidylcholine (DPPC); distearoylphosphatidylcholine (DSPC); and diarachidonylphosphatidylcholine (DAPC); phosphatidylethanolamines, such as dioleoylphosphatidylethanolamine, dipalmitoylphosphatidylethanolamine (DPPE) and distearoylphosphatidylethanolamine (DSPE); phosphatidylserine; phosphatidylglycerols, including distearoylphosphatidylglycerol (DSPG); phosphatidylinositol; sphingolipids such as sphingomyelin; glycolipids such as ganglioside GM1 and GM2; glucolipids; sulfatides; glycosphingolipids; phosphatidic acids, such as dipalmitoylphosphatidic acid (DPPA) and distearoylphosphatidic acid (DSPA); palmitic acid; stearic acid; arachidonic acid; oleic acid; lipids bearing polymers, such as chitin, hyaluronic acid, polyvinylpyrrolidone or polyethylene glycol (PEG), also referred to herein as "pegylated lipids" with preferred lipid bearing polymers including DPPE-PEG (DPPE-PEG), which refers to the lipid DPPE having a PEG polymer attached thereto, including, for example, DPPE-PEG5000, which refers to DPPE having attached thereto a PEG polymer having a mean average molecular weight of about 5000; lipids bearing sulfonated mono-, di-, oligo- or polysaccharides; cholesterol, cholesterol sulfate and cholesterol hemisuccinate; tocopherol hemisuccinate; lipids with ether and ester-linked fatty acids; polymerized lipids (a wide variety of which are well known in the art); diacetyl phosphate; dicetyl phosphate; stearylamine; cardiolipin; phospholipids with short chain fatty acids of about 6 to about 8 carbons in length; synthetic phospholipids with asymmetric acyl chains, such as, for example, one acyl chain of about 6 carbons and another acyl chain of about 12 carbons; ceramides; non-ionic liposomes including niosomes such as polyoxyethylene fatty acid esters, polyoxyethylene fatty alcohols, polyoxyethylene fatty alcohol ethers, polyoxyalkylene sorbitan fatty acid esters (such as, for example, the class of compounds referred to as TWEEN™, commercially available from ICI Americas, Inc., Wilmington, Del.), including polyoxyethylated sorbitan fatty acid esters, glycerol polyethylene glycol oxystearate, glycerol polyethylene glycol ricinoleate, ethoxylated soybean sterols, ethoxylated castor oil, polyoxyethylene-polyoxypropylene polymers, and polyoxyethylene fatty acid stearates; sterol aliphatic acid esters including cholesterol sulfate, cholesterol butyrate, cholesterol isobutyrate, cholesterol palmitate, cholesterol stearate, lanosterol acetate, ergosterol palmitate, and phytosterol n-butyrate; sterol esters of sugar acids including cholesterol glucuronide, lanosterol glucuronide, 7-dehydrocholesterol glucuronide, ergosterol glucuronide, cholesterol gluconate, lanosterol gluconate, and ergosterol gluconate; esters of sugar acids and alcohols including lauryl glucuronide, stearoyl glucuronide, myristoyl glucuronide, lauryl gluconate, myristoyl gluconate, and stearoyl gluconate; esters of sugars and aliphatic acids including sucrose laurate, fructose laurate, sucrose palmitate, sucrose stearate, glucuronic acid, gluconic acid and polyuronic acid; saponins including sarsasapogenin, smilagenin, hederagenin, oleanolic acid, and digitoxigenin; glycerol dilaurate, glycerol trilaurate, glycerol dipalmitate, glycerol and glycerol esters including glycerol tripalmitate, glycerol distearate, glycerol tristearate, glycerol dimyristate, glycerol trimyristate; long chain alcohols including n-decyl alcohol, lauryl alcohol, myristyl alcohol, cetyl alcohol, and n-octadecyl alcohol; 6-(5-cholesten-3β-yloxy)-1-thio-β-D-galactopyranoside; digalactosyldiglyceride; 6-(5-cholesten-3β-yloxy)-hexyl-6-amino-6-deoxy-1-thio-β-D-galactopyranoside; 6-(5-cholesten-3β-yloxy)hexyl-6-amino-6-deoxyl-1-thio-α-D-mannopyranoside; 12-(((7'-diethylamino-coumarin-3-yl)-carbonyl)-methylamino)-octadecanoic acid; N-[12-(((7'-diethylamino-coumarin-3-yl)-carbonyl)-methylamino)-octadecanoyl]- 2-aminopalmitic acid; cholesteryl(4'-trimethyl-ammonio)-butanoate; N-succinyldioleoylphosphatidylethanol-amine; 1,2-dioleoyl-sn-glycerol; 1,2-dipalmitoyl-sn-3-succinylglycerol; 1,3-dipalmitoyl-2-succinylglycerol; 1-hexadecyl-2-palmitoylglycerophosphoethanolamine and palritoylhomocysteine, and/or any combinations thereof.

Examples of polymerized lipids include unsaturated lipophilic chains such as alkenyl or alkynyl, containing up to about 50 carbon atoms. Further examples are phospholipids such as phosphoglycerides and sphingolipids carrying polymerizable groups, and saturated and unsaturated fatty acid derivatives with hydroxyl groups, such as for example triglycerides of d-12-hydroxyoleic acid, including castor oil and ergot oil. Polymerization may be designed to include hydrophilic substituents such as carboxyl or hydroxyl groups t,- enhance dispersability so that the backbone residue resulting from biodegradation is water soluble. Exemplary polymerizable lipid compounds which may be utilized in the compositions of the present invention are illustrated below.

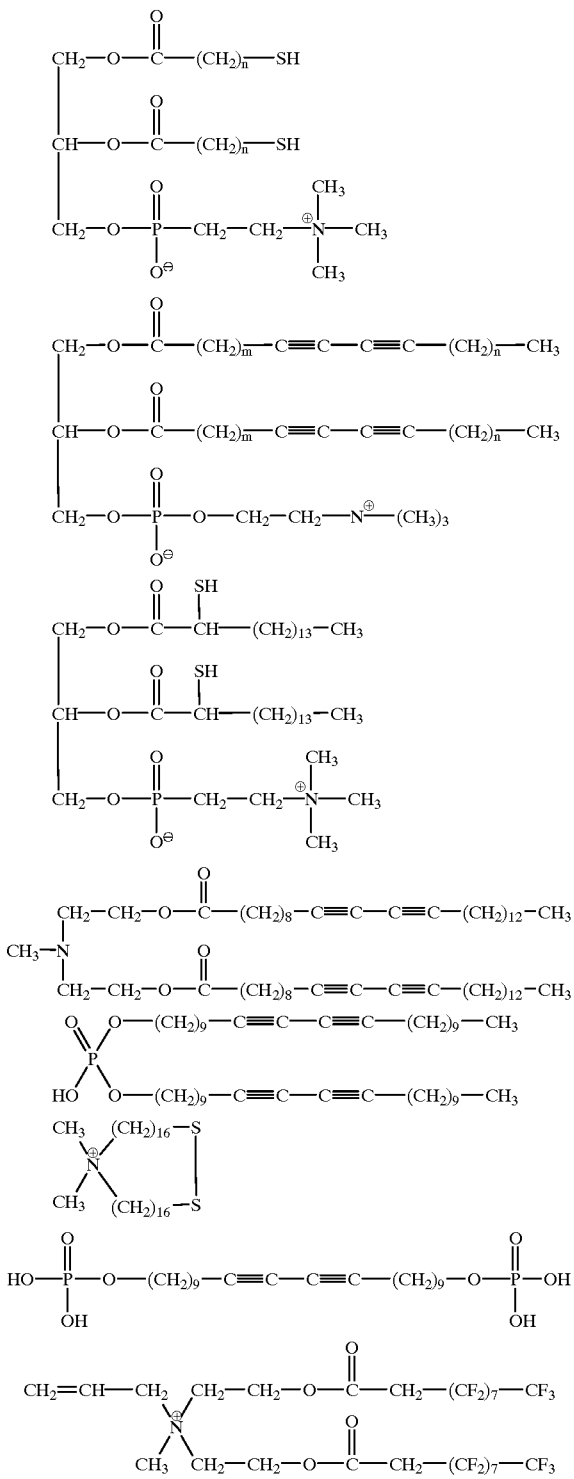

In preferred embodiments, the surfactant comprises phospholipids, including one or more of DPPC, DPPE, DPPA, DSPC, DSPE, DSPG, and DAPC (20 carbon atoms).

If desired, the stabilizing material may comprise a cationic lipid, such as, for example, N-[1-(2,3-dioleoyloxy) propyl]-N,N,N-trimethylammonium chloride (DOTMA), 1,2-dioleoyloxy-3-(trimethylammonio)propane (DOTAP); and 1,2-dioleoyl-3-(4'-trimethylammonio)-butanoyl-sn-glycerol (DOTB). If a cationic lipid is employed in the stabilizing materials, the molar ratio of cationic lipid to non-cationic lipid may be, for example, from about 1:1000 to about 1:100. Preferably, the molar ratio of cationic lipid to non-cationic lipid may be from about 1:2 to about 1:10, with a ratio of from about 1:1 to about 1:2.5 being preferred. Even more preferably, the molar ratio of cationic lipid to non-cationic lipid may be about 1:1.

If desired, compositions may be constructed of one or more charged lipids in association with one or more polymer bearing lipids, optionally in association with one or more neutral lipids. The charged lipids may either be anionic or cationic. Typically, the lipids are aggregated in the presence of a multivalent species, such as a counter ion, opposite in charge to the charged lipid. For delivery of therapeutics such as prodrugs and/or bioactive agents to selective sites in vivo, therapeutic delivery systems of the present invention may be of micron or sub-micron size. Preferably the therpeutic delivery systems are less than about 10 microns, more preferably under about 2 microns, more preferably less than about 1 micron, more preferably under about 0.5 microns, and even more preferably under about 200 nm are desired. Most preferably the lipid aggregates are under 200 nm in size and may be as small as about 5 to about 10 nm in size. The therapeutic delivery sytems may be from about 100 microns to about 1 millimeter in size as well. For IV and pulmonary administration, smaller therapeutic delivery systems are preferred.

Exemplary anionic lipids include phosphatidic acid and phosphatidyl glycerol and fatty acid esters thereof, amides of phosphatidyl ethanolamine such as anandamides and methanandamides, phosphatidyl serine, phosphatidyl inositol and fatty acid esters thereof, cardiolipin, phosphatidyl ethylene glycol, acidic lysolipids, sulfolipids, and sulfatides, free fatty acids, both saturated and unsaturated, and negatively charged derivatives thereof. Phosphatidic acid and phosphatidyl glycerol and fatty acid esters thereof are preferred anionic lipids.

When the charged lipid is anionic, a multivalent (divalent, trivalent, etc.) cationic material may be used. Useful cations include, for example, cations derived from alkaline earth metals, such as berylium ($Be^{+2}$), magnesium ($Mg^{+2}$), calcium ($Ca^{+2}$), strontium ($Sr^{+2}$), and barium ($Ba^{+2}$); amphoteric ions such as aluminum ($Al^{+3}$), gallium ($Ga^{+3}$), germanium ($Ge^{+3}$), tin ($Sn^{+4}$), and lead ($Pb^{+2}$ and $Pb^{+4}$); transition metals such as titanium ($Ti^{+3}$ and $Ti^{+4}$), vanadium ($V^{+2}$ and $V^{+3}$), chromium ($Cr^{+2}$ and $Cr^{+3}$), manganese ($Mn^{+2}$ and $Mn^{+3}$), iron ($Fe^{+2}$ and $Fe^{+3}$), cobalt ($Co^{+2}$ and $Co^{+3}$), nickel ($Ni^{+2}$ and $Ni^{+3}$), copper ($Cu^{+2}$), zinc ($Zn^{+2}$), zirconium ($Zr^{+4}$), niobium ($Nb^{+3}$), molybdenum ($Mo^{+2}$ and $Mo^{+3}$), cadmium ($Cd^{+2}$), indium ($In^{+3}$), tungsten ($W^{+2}$ and $W_{+4}$), osmium ($Os^{+2}$, $Os^{+3}$ and $Os^{+4}$), iridium ($Ir^{+2}$, $Ir^{+3}$ and $Ir^{+4}$), mercury ($Hg^{+2}$), and bismuth ($Bi^{+3}$); and rare earth lanthanides, such as lanthanum ($La^{+3}$), and gadolinium ($Gd^{+3}$). It is contemplated that cations in all of their ordinary valence states will be suitable for forming aggregates and cross-linked lipids. Preferred cations include calcium ($Ca^{+}_2$), magnesium ($Mg^{+2}$), and zinc ($Zn^{+2}$) and paramagnetic cations such as manganese (preferably $Mn^{+2}$) and gadolinium ($Gd^{+3}$). Particularly preferred is calcium ($Ca^{+2}$). As will be apparent to one skilled in the art, some of the above ions (notably lead and nickel) may have associated toxicity and thus may be inappropriate for in vivo use.

When the charged lipid is cationic, an anionic material, for example, may be used. Preferably, the anionic material is multivalent, such as, for example, divalent. Examples of useful anionic materials include monatomic and polyatomic anions such as carboxylate ions, sulfide ion, sulfite ions, sulfate ions, oxide ions, nitride ions, carbonate ions, and phosphate ions. Anions of ethylene diamine tetraacetic acid (EDTA), diethylene triamine pentaacetic acid (DTPA), and 1, 4, 7, 10-tetraazocyclododecane-N', N', N", N"-tetraacetic acid (DOTA) may also be used. Further examples of useful anionic materials include anions of polymers and copolymers of acrylic acid, methacrylic acid, other polyacrylates and methacrylates, polymers with pendant $SO_3H$ groups, such as sulfonated polystyrene, and polystyrenes containing carboxylic acid groups.

Examples of cationic lipids include those listed hereinabove. A preferred cationic lipid for formation of aggregates is N-[1-(2,3-dioleoyloxy)propyl]-N,N,N-trimethylammonium chloride ("DOTMA"). Synthetic cationic lipids may also be used. These include common natural lipids derivatized to contain one or more basic functional groups. Examples of lipids which can be so modified include dimethyldioctadecylammonium bromide, sphinolipids, sphingomyelin, lysolipids, glycolipids such as ganglioside GM1, sulfatides, glycosphingolipids, cholesterol and cholesterol esters and salts, N-succinyldioleoylphosphatidylethanolamine, 1,2,-dioleoyl-sn-glycerol, 1,3-dipalmitoyl-2-succinylglycerol, 1,2-dipalmitoyl-sn-3-succinylglycerol, 1-hexadecyl-2-palmitoylglycerophosphatidylethanolamine and palmitoylhomocystiene.

Specially synthesized cationic lipids also function in the embodiments of the invention. Among these are those disclosed in pending U.S. patent application Ser. No. 08/391,938, filed Feb. 21, 1995, the disclosure of which is hereby incorporated herein by reference in its entirety, and include, for example, N,N'-bis (dodecyaminocarbonyl-methylene)-N,N'-bis (β-N,N,N-trimethylammoniumethyl-aminocarbonylmethyleneethylene-diamine tetraiodide; N,N"-bis hexadecylaminocarbonylmethylene)-N,N',N"-tris (β-N,N,N-trimethylammoniumethylami-nocarbonylmethylenediethylenetriamine hexaiodide; N,N'-Bis(dodecylaminocarbonylmethylene)-N,N"-bis(β-N,N,N-trimethylammoniumethylamino-carbonylmethylene) cyclohexylene-1,4-diaminetetraiodide; 1,1,7,7-tetra-(β-N,N,N-tetramethylammoniumethylaminocarbonylmethylene)-3-hexadecylaminocarbonyl-methylene-1,3,7-triaazaheptane heptaiodide; and N,N,N'N'-tetraphosphoethanolamino-carbonylmethylene)diethylenetriamine tetraiodide.

In the case of surfactants which contain both cationic and non-cationic lipids, a wide variety of lipids, as described above, may be employed as the non-cationic lipid. Preferably, the non-cationic lipid comprises one or more of DPPC, DPPE and dioleoylphosphatidylethanolamine. In lieu of the cationic lipids listed above, lipids bearing cationic polymers, such as polylysine or polyarginine, as well as alkyl phosphonates, alkyl phosphinates, and alkyl phosphites, may also be used in the stabilizing materials. Those of skill in the art will recognize, in view of the present disclosure, that other natural and synthetic variants carrying positive charged moieties will also function in the invention.

Saturated and unsaturated fatty acids which may be employed in the present stabilizing materials include molecules that preferably contain from about 12 carbon atoms to about 22 carbon atoms, in linear or branched form. Hydrocarbon groups consisting of isoprenoid units and/or prenyl groups can be used. Examples of suitable saturated fatty acids include, for example, lauric, myristic, palmitic, and stearic acids. Examples of suitable unsaturated fatty acids include, for example, lauroleic, physeteric, myristoleic, palmitoleic, petroselinic, and oleic acids. Examples of suitable branched fatty acids include, for example, isolauric, isomyristic, isopalmitic, and isostearic acids.

Other useful lipids or combinations thereof apparent to those skilled in the art which are in keeping with the spirit of the present invention are also encompassed by the present invention. For example, carbohydrate-bearing lipids may be employed, as described in U.S. Patent No. 4,310,505, the disclosure of which is hereby incorporated herein by reference in its entirety.

Alternatively, it may be desirable to use a fluorinated compound, especially a perfluorocarbon compound, which may be in the liquid state at the temperature of use, including, for example, the in vivo temperature of the human body, to assist or enhance the stability of the lipid and/or vesicle compositions, and especially, gas filled vesicles. Suitable liquid perfluorocarbons which may be used include, for example, perfluorodecalin, perfluorododecalin, perfluorooctyliodide, perfluorooctylbromide, perfluorotripropylamine, and perfluorotributylamine. In general, perfluorocarbons comprising about six or more carbon atoms will be liquids at normal human body temperature. Among these perfluorocarbons, perfluorooctylbromide and perfluorohexane, which are liquids at room temperature, are preferred. The gas which is present may be, for example, nitrogen or perfluoropropane, or may be derived from a gaseous precursor, which may also be a perfluorocarbon, for example, perfluoropentane. In the latter case, stabilizing materials and/or vesicle compositions may be prepared from a mixture of perfluorocarbons, which for the examples given, would be perfluoropropane (gas) or perfluoropentane (gaseous precursor) and perfluorooctylbromide (liquid). Although not intending to be bound by any theory or theories of operation, it is believed that, in the case of vesicle compositions, the liquid fluorinated compound may be situated at the interface between the gas and the membrane or wall surface of the vesicle. There may be thus formed a further stabilizing layer of liquid fluorinated compound on the internal surface of the vesicle, for example, a biocompatible lipid used to form the vesicle, and this perfluorocarbon layer may also prevent the gas from diffusing through the vesicle membrane. A gaseous precursor, within the context of the present invention, is a liquid at the temperature of manufacture and/or storage, but becomes a gas at least at or during the time of use.

A liquid fluorinated compound, such as a perfluorocarbon, when combined with a gas and/or gaseous precursor ordinarily used to make the lipid and/or vesicles described herein, may confer an added degree of stability not otherwise obtainable with the gas and/or gaseous precursor alone. Thus, it is within the scope of the present invention to utilize a gas and/or gaseous precursor, such as a perfluorocarbon gaseous precursor, for example, perfluoropentane, together with a perfluorocarbon which remains liquid after administration to a patient, that is, whose liquid to gas phase transition temperature is above the body temperature of the patient, for example, perfluorooctylbromide. Perfluorinated surfactants, such as the DuPont Company's ZONYL® fluorinated surfactants, ZONYL® phosphate salts, ZONYL® sulfate salts, and ZONYL® surfactants identified as Telomer B, including Telomer B surfactants which are pegylated (i.e., have at least one polyethylene glycol group attached thereto), also known as PEG-Telomer B, may be used to stabilize the lipid and/or vesicle compositions, and to act, for example, as a coating for vesicles. Preferred perfluorinated surfactants are the partially fluorinated phosphocholine surfactants. In these preferred fluorinated surfactants, the dual alkyl compounds may be fluorinated at the terminal alkyl chains and the proximal carbons may be hydrogenated. These fluorinated phosphocholine surfactants may be used for making the compositions of the present invention.

Other suitable fluorinated compounds for use as the stabilizing material of the present invention are set forth in U.S. Pat. No. 5,562,893, the disclosure of which is hereby incorporated herein by reference in its entirety. For example, synthetic organic monomeric repeating units may be used to form polymers suitable as stabilizing materials in the present invention, including hydroxyacids, lactones, lactides, glycolides, acryl containing compounds, aminotriazol, orthoesters, anyhdrides, ester imides, imides, acetals, urethanes, vinyl alcohols, enolketones, and organosiloxanes.

The method of introducing fluorine into any of these materials is well known in the art. For example, the introduction of perfluoro-t-butyl moieties is described in U.S. Pat. No. 5,234,680, the disclosure of which is hereby incorporated by reference herein in its entirety. These methods generally involve the reaction of perfluoroalkyl carbanions with host molecules as follows: $(CF_3)_3C^- + R—X \rightarrow (CF_3)_3C—R$, where R is a host molecule and X is a good leaving group, such as bromine, chlorine, iodine or a sulfonato group. After adding a leaving group to the foregoing stabilizing material using methods well known in the art, perfluoro-t-butyl moieties can then be easily introduced to these derivatized stabilizing materials as described above.

Additional methods are known for the introduction of trifluoromethyl groups into various organic compounds are well known in the art. For example, trifluoromethyl groups may be introduced by nucleophilic perfluoroalkylation using perfluoroalkyl-trialkylsilanes.

Fluorine can be introduced into any of-the aforementioned stabilizing materials or vesicles either in their monomeric or polymeric form. Preferably, fluorine moieties are introduced into monomers, such as fatty acids, amino acids or polymerizable synthetic organic compounds, which are then polymerized for subsequent use as stabilizing materials and/or vesicles.

The introduction of fluorine into stabilizing materials and/or vesicles may also be accomplished by forming vesicles in the presence of a perfluorocarbon gas. For example, when vesicles are formed from proteins, such as human serum albumin in the presence of a perfluorocarbon gas, such as perfluoropropane, using mechanical cavitation, fluorine from the gas phase becomes bound to the protein vesicles during formation. The presence of fluorine in the vesicles and/or stabilizing materials can be detected by NMR of vesicle debris which has been purified from disrupted vesicles. Fluorine can also be introduced into stabilizing materials and/or vesicles using other methods, such as sonication, spray-drying or emulsification techniques. Another way in which fluorine can be introduced into the shell material is by using a fluorine-containing reactive compound. The term "reactive compound" refers to compounds which are capable of interacting with the stabilizing material and/or vesicle in such a manner that fluorine moieties become covalently attached to the stabilizing material and/or vesicle. When the stabilizing material is a protein, preferred reactive compounds are either alkyl esters or acyl halides which are capable of reacting with the protein's amino groups to form an amide linkage via an acylation reaction. The reactive compound can be introduced at any stage during vesicle formation, but is preferably added to the gas phase prior to vesicle formation. For example, when vesicles are to be made using mechanical or ultrasound cavitation techniques, the reactive compound can be added to the gas phase by bubbling the gas to be used in the formation of the vesicles (starting gas) through a solution of the reactive compound into the gas phase. The resultant gas mixture, which now contains the starting gas and the reactive compound, is then used to form vesicles. The vesicles are preferably formed by sonication of human serum albumin in the presence of a gas mixture, as described in U.S. Pat. No. 4,957,656, the disclosure of which is hereby incorporated herein by reference in its entirety.

Suitable fluorine containing alkyl esters and acyl halides for use as stabilizing materials and/or vesicle forming materials in the present invention include, for example, diethyl hexafluoroglutarate, diethyl tetrafluorosuccinate, methyl heptafluorobutyrate, ethyl heptafluorobutyrate, ethyl pentafluoropropionate, methyl pentafluoropropionate, ethyl perfluorooctanoate, methyl perfluorooctanoate, nonafluoropentanoyl chloride, perfluoropropionyl chloride, hexafluoroglutaryl chloride and heptafluorobutyryl chloride.

Other fluorine containing reactive compound can also be synthesized and used as the stabilizing materials and/or vesicle forming materials in the present invention, including, for example, aldehydes, isocyanates, isothiocyanates, epoxides, sulfonyl halides, anhydrides, acid halides and alkyl sulfonates, which contain perfluorocarbon moieties, including $—CF_3$, $—C_2F_5$, $—C_3F_4$ and $—C(CF_3)_3$. These reactive compounds can be used to introduce fluorine moieties into any of the aforementioned stabilizing materials by choosing a combination which is appropriate to achieve covalent attachment of the fluorine moiety.

Sufficient fluorine should be introduced to decrease the permeability of the vesicle to the aqueous environment. This will result in a slower rate of gas exchange with the aqueous environment which is evidenced by enhanced pressure resistance. Although the specific amount of fluorine necessary to stabilize the vesicle will depend on the components of the vesicle and the gas contained therein, after introduction of fluorine the vesicle will preferably contain 0.5 to 20% by weight, and more preferably about 1 to 10% by weight fluorine.

The Therapeutic

Therapeutics, such as for example genetic and bioactive materials, may be attached to the targeted therapeutic delivery system such that it is incorporated into the void of the microsphere or onto the inner or outer microsphere surface.

Therapeutics with a high octanol/water partition coefficient may be incorporated directly into the layer or wall surrounding the gas but incorporation onto the surface of either the surfactant or carrier is more preferred. To accomplish this, groups capable of binding therapeutics may generally be incorporated into the surfactant or carrier which will then bind these materials. In the case of genetic materials, this is readily accomplished through the use of cationic lipids or cationic polymers which may be incorporated into the dried starting materials.

The octanol partition coefficient may be determined for various drugs by measuring the amounts of drug which partitions into octanol and water. Table 3 below shows the octanol/water partition coefficients of a variety of drugs. In general, acoustically active liposheres (AALs) are best for drugs with an octanol partition coefficient of greater than 1.0, even more preferably a partition coefficient of greater than 10 to 1, and still even more preferably greater than 50. Taxol is an exemplary drug well suited to AALs as its octanol partition coefficient is 99. Drugs with low octanol/water partition coefficients may be alkylated or acylated to increase their lipophilicity. Alternatively hydrophilic drugs can be suspended as insoluble crystals within the oil of AALs.

TABLE 3

Octanol/Water Partition Coefficients of Drugs

| Hexamethylene | $2 \times 10^7$ |
|---|---|
| Parsol | $5 \times 10^6$ |
| Lauramide o-padimate | $3.98 \times 10^6$ |
| Dietylstilbesterol | $1.26 \times 10^5$ |
| Biotin | $4.09 \times 10^4$ |
| Ethanolamine | $3.67 \times 10^4$ |
| Anthracene | $3.16 \times 10^4$ |
| Progesterone | $7.9 \times 10^3$ |
| Clomipramine | $3.8 \times 10^3$ |
| Clotiazepam | $3.06 \times 10^3$ |
| Testosterone | $2.0 \times 10^3$ |
| Chlorpromazine | $1.90 \times 10^3$ |
| Trihexyphenidyl | $1.47 \times 10^3$ |
| Promethazine | $1.27 \times 10^3$ |
| Diazepam | $9.7 \times 10^2$ |
| Hexanoyl Acyclovir | $8.58 \times 10^2$ |
| Biperiden | $6.78 \times 10^2$ |
| Haloperidol | $4.85 \times 10^2$ |
| Bunulol | $2.51 \times 10^2$ |
| Valeryl Acyclovir | $2.01 \times 10^2$ |
| Halothane | $2 \times 10^2$ |
| Oxazepam | $1.78 \times 10^2$ |
| Nitrazepam | $1.62 \times 10^2$ |
| Pentazocin | $1.50 \times 10^2$ |
| Fluoromethalone | $1.26 \times 10^2$ |
| Ampicillin | $1.15 \times 10^2$ |
| Taxol | 99 |
| Tetracaine | 79.4 |
| Bupivicaine | 28.2 |
| Clonidine | 25.1 |
| Cimetidine | 2.51 |
| Lidocaine | 2.28 |

When a drug has a relatively low octanol/water partition coefficient, e.g, less than 10, the drug may be modified to increase its lipophilicity by reaction with hydrophobic groups such as alkyl or arylalkyl moities which may be optionally fluorinated. Lipophilic drugs may also be modified in this manner. For example, dexamethasone can be made more amphiphilic by conversion to DPGS-dexamethasone, as described in U.S. application Ser. No. 08/851,780, or cholesterol can be used as with cholesterol hemisuccinate or other cholesterol derivatives modified with a reactive moiety. As those skilled in the art will appreciate, such amphiphilic forms of hydrophobic chemicals readily partition into organic solvents, but also retain a degree of water solubility that allows them not to precipitate in serum in small quantities. Hydrophilic drugs can also be used in the AALs by forming micro- or nanocrystalline materials surrounded by a surfactant and then suspending in the oil phase. This is generally accomplished by mixing powdered, dry quantities of the drug into the oil or wax to form microprecipitates within the solvent. Chemotherapeutics such as bleomycin and etoposide may be prepared in this manner. Dried drugs, generally in the ratio of from 0.001% to 90% by weight in oil or wax may be prepared in this way.

Other suitable therapeutics include, antifungal agents, and bioactive agents, such as for example, antineoplastic agents, such as platinum compounds (e.g., spiroplatin, cisplatin, and carboplatin), methotrexate, adriamycin, taxol, mitomycin, ansamitocin, bleomycin, cytosine arabinoside, arabinosyl adenine, mercaptopolylysine, vincristine, busulfan, chlorambucil, melphalan (e.g., L-sarolysin (L-PAM, also known as Alkeran) and phenylalanine mustard (PAM)), mercaptopurine, mitotane, procarbazine hydrochloride, dactinomycin (actinomycin D), daunorubicin hydrochloride, doxorubicin hydrochloride, mitomycin, plicamycin (mithramycin), aminoglutethimide, estramustine phosphate sodium, flutamide, leuprolide acetate, megestrol acetate, tamoxifen citrate, testolactone, trilostane, amsacrine (m-AMSA), asparaginase (L-asparaginase) Erwina asparaginase, etoposide (VP-16), interferon α-2a, interferon α-2b, teniposide (VM-26), vinblastine sulfate (VLB), vincristine sulfate, bleomycin, bleomycin sulfate, methotrexate, adriamycin, carzelesin, and arabinosyl; blood products such as parenteral iron, hemin, hematoporphyrins and their derivatives; biological response modifiers such as muramyldipeptide, muramyltripeptide, prostaglandins, microbial cell wall components, lymphokines (e.g., bacterial endotoxin such as lipopoly-saccharide, macrophage activation factor), sub-units of bacteria (such as Mycobacteria and Corynebacteria), the synthetic dipeptide N-acetyl-muramyl-L-alanyl-D-isoglutamine; anti-fungal agents such as ketoconazole, nystatin, griseofulvin, flucytosine (5-fc), miconazole, amphotericin B, ricin, and β-lactam antibiotics (e.g., sulfazecin); hormones such as growth hormone, melanocyte stimulating hormone, estradiol, beclomethasone dipropionate, betamethasone, betamethasone acetate and betamethasone sodium phosphate, vetamethasone disodium phosphate, vetamethasone sodium phosphate, cortisone acetate, dexamethasone, dexamethasone acetate, dexamethasone sodium phosphate, flunsolide, hydrocortisone, hydrocortisone acetate, hydrocortisone cypionate, hydrocortisone sodium phosphate, hydrocortisone sodium succinate, methylprednisolone, methylprednisolone acetate, methylprednisolone sodium succinate, paramethasone acetate, prednisolone, prednisolone acetate, prednisolone sodium phosphate, prednisolone tebutate, prednisone, triamcinolone, triamcinolone acetonide, triamcinolone diacetate, triamcinolone hexacetonide, fludrocortisone. acetate, progesterone, testosterone, and adrenocorticotropic hormone; vitamins such as cyanocobalamin neinoic acid, retinoids and derivatives such as retinol palmitate, α-tocopherol, naphthoquinone, cholecalciferol, folic acid, and tetrahydrofolate; peptides, such as angiostatin, manganese super oxide dismutase, tissue plasminogen activator, glutathione, insulin, dopamine, peptides with affinity for the GPIIbIIIa receptor (usually found on activated receptor platelets) such as RGD, AGD, RGE, KGD, KGE, and KQAGDV, opiate peptides (such as enkephalines and endorphins), human chorionic gonadotropin, corticotropin release factor, cholecystokinins, bradykinins, promoters of bradykinins, inhibitors of bradykinins, elastins, vasopressins, pepsins, glucagon, substance P (a pain moderation peptide), integrins, Angiotensin Converting Enzyme (ACE) inhibitors (such as captopril, enalapril, and lisinopril), adrenocorticotropic hormone, oxytocin, calcitonins, IgG, IgA, IgM, ligands for Effector Cell Protease Receptors, thrombin, streptokinase, urokinase, Protein Kinase C, interferons (such as interferon α, interferon β, and interferon γ), colony stimulating factors, granulocyte colony stimulating factors, granulocyte-macrophage colony stimulating factors, tumor necrosis factors, nerve growth factors, platelet derived growth factors, lymphotoxin, epidermal growth factors, fibroblast growth factors, vascular endothelial cell growth factors, erythropoeitin, transforming growth factors, oncostatin M, interleukins (such as interleukin 1, interleukin 2, interleukin 3, interleukin 4, interleukin 5, interleukin 6, interleukin 7, interleukin 8, interleukin 9, interleukin 10, interleukin 11, and interleukin 12.), metalloprotein kinase ligands, and collagenases; enzymes such as alkaline phosphatase and cyclooxygenases; anti-allergic agents such as amelexanox; anti-coagulation agents such as phenprocoumon and heparin; circulatory drugs such as propranolol; metabolic potentiators such as glutathione; antituberculars such as para-aminosalicylic acid, isoniazid, capreomycin sulfate cycloserine, ethambutol hydrochloride ethionanide, pyrazinamide, rifampin, and streptomycin sulfate; antivirals such as acyclovir, amantadine azidothymidine (AZT or Zidovudine), ribavirin, amantadine, vidarabine, and vidarabine monohydrate (adenine arabinoside, ara-A); antianginals such as diltiazem, nifedipine, verapamil, erythrityl tetranitrate, isosorbide dinitrate, nitroglycerin (glyceryl trinitrate) and pentaerythritol tetranitrate; anticoagulants such as phenprocoumon, heparin; antibiotics such as dapsone, chloramphenicol, neomycin, cefaclor, cefadroxil, cephalexin, cephradine erythromycin, clindamycin, lincomycin, amoxicillin, ampicillin, bacampicillin, carbenicillin, dicloxacillin, cyclacillin, picloxacillin, hetacillin, methicillin, nafcillin, oxacillin, penicillin G, penicillin V, ticarcillin, rifampin and tetracycline; antiinflammatories such as difimisal, ibuprofen, indomethacin, meclofenamate, mefenamic acid, naproxen, oxyphenbutazone, phenylbutazone, piroxicam, sulindac, tolmetin, aspirin and salicylates; antiprotozoans such as chloroquine, hydroxychloroquine, metronidazole, quinine and meglumine antimonate; antirheumatics such as penicillamine; narcotics such as paregoric and opiates such as codeine, heroin, methadone, morphine and opium; cardiac glycosides such as deslanoside, digitoxin, digoxin, digitalin and digitalis; neuromuscular blockers such as atracurium besylate, gallamine triethiodide, hexafluorenium bromide, metocurine iodide, pancuronium bromide, succinylcholine chloride (suxamethonium chloride), tubocurarine chloride and vecuronium bromide; sedatives (hypnotics) such as amobarbital, amobarbital sodium, aprobarbital, butabarbital sodium, chloral hydrate, ethchlorvynol, ethinamate, flurazepam hydrochloride, glutethimide, methotrimeprazine hydrochloride, methyprylon, midazolam hydrochloride, paraldehyde, pentobarbital, pentobarbital sodium, phenobarbital sodium, secobarbital sodium, talbutal, temazepam and triazolam; local anesthetics such as bupivacaine hydrochloride, chloroprocaine hydrochloride, etidocaine hydrochloride, lidocaine hydrochloride, mepivacaine hydrochloride, procaine hydrochloride and tetracaine hydrochloride; general anesthetics such as droperidol, etomidate, fentanyl citrate with droperidol, ketamine hydrochloride, methohexital sodium and thiopental sodium; and radioactive particles or ions such as strontium, iodide rhenium, technetium, cobalt, and yttrium. In certain preferred embodiments, the bioactive agent is a monoclonal antibody, such as a monoclonal antibody capable of binding to melanoma antigen.

Certain preferred therapeutics, such as for the treatment of ophthalmologic diseases and prostate cancer, for example, include ganciclovir, vascular endothelial growth factor, foscarnet, S-(1,3 hydroxyl-2-phosphonylmethoxypropyl) cytosine, nitric oxide synthase inhibitors, aldose reductase inhibitors (such as sorbinil and tolrestat), LY333531 (an isozyme-selective inhibitor of protein kinase C-β, see Faul, et al., "Synthesis of LY333531, an isozyme selective inhibitor of protein kinase C-β", *Abstracts of papers of the American Chemical Society* 1997 213, part 2, 567, the disclosure of which is incorporated herein by reference in its entirety), cidofovir, vitamin E, aurintricarboxylic acid, somatuline, Trolox™, sorvudine, α-interferon, etofibrate, filgastrim, aminoguanidine, ticlopidine, ponalrestat, epalrestat, granulocyte macrophage colony stimulating factor (GM-CSF), dipyridamole+aspirin, nipradilol, haloperidol, latanoprost, dipifevrin, vascular endothelial growth factor, timolol, dorzolamide, adaprolol enantiomers, bifemelane hydrochloride, apraclonidine hydrochloride, vaninolol, betaxolol, etoposide, 3-α, 5-β-tetrahydrocortisol, pilocarpine, bioerodible poly(ortho ester), levobunolol, prostanoic acid, N-4 sulphanol benzyl-imidazole, imidazo pyridine, 3-(Bicyclyl methylene) oxindole, 15-deoxy spergualin, benzoylcarbinol salts, fumagillin, lecosim, bendazac, N-acyl-5-hydroxytryptamine, cetrorelix acetate, 17-α-acyl steroids, azaandrosterone, 5-α-reductase inhibitor, and antiestrogenics (such as 2-4-{1,2-diphenyl-1-butenyl}phenoxy)-N,N-dimethylethanamine).

Other preferred therapeutics include genetic material such as nucleic acids, RNA, and DNA, of either natural or synthetic origin, including recombinant RNA and DNA and antisense RNA and DNA. Types of genetic material that may be used include, for example, genes carried on expression vectors such as plasmids, phagemids, cosmids, yeast artificial chromosomes (YACs), and defective or "helper" viruses, antigene nucleic acids, both single and double stranded RNA and DNA and analogs thereof, such as phosphorothioate and phosphorodithioate oligodeoxynucleotides. Additionally, the genetic material may be combined, for example, with proteins or other polymers. Examples of genetic material that may be applied using the liposomes of the present invention include, for example, DNA encoding at least a portion of LFA-3, DNA encoding at least a portion of an HLA gene, DNA encoding at least a portion of dystrophin, DNA encoding at least a portion of CFTR, DNA encoding at least a portion of IL-2, DNA encoding at least a portion of TNF, and an antisense oligonucleotide capable of binding the DNA encoding at least a portion of Ras.

DNA encoding certain proteins may be used in the treatment of many different types of diseases. For example, adenosine deaminase may be provided to treat ADA deficiency; tumor necrosis factor and/or interleukin-2 may be provided to treat advanced cancers; HDL receptor may be provided to treat liver disease; thymidine kinase may be provided to treat ovarian cancer, brain tumors, or HIV infection; HLA-B7 may be provided to treat malignant melanoma; interleukin-2 may be provided to treat neuroblastoma, malignant melanoma, or kidney cancer; interleukin-4 may be provided to treat cancer; HIV env may be provided to treat HIV infection; antisense ras/p53 may be provided to treat lung cancer; and Factor VIII may be provided to treat Hemophilia B. See, for example, *Science* 258:744–746.

Dyes are included within the definition of therapeutics. Dyes may be useful for identifying the location of a vesicle within a patient's body or particular region of a patient's body. Following administration of the vesicle compositions, and locating, with energy, such compositions within a region of a patient's body to be treated, the dye may be released from the composition and visualized by energy. Dyes useful in the present invention include fluorescent dyes and colorimetric dyes, such as sudan black, fluorescein, R-Phycoerythrin, texas red, BODIPY FL, oregon green, rhodamine red-X, tetramethylrhodamine, BODIPY TMR, BODIPY-TR, YOYO-1, DAPI, Indo-1, Cascade blue, fura-2, amino methylcoumarin, FM1-43, NBD, carbosy-SNARF, lucifer yellow, dansyl+R—$NH_2$, propidium iodide, methylene blue, bromocresol blue, acridine orange, bromophenol blue, 7-amino-actinomycin D, allophycocyanin, 9-azidoacridine, benzoxanthene-yellow, bisbenzidide H 33258 fluorochrome, 3HCl, 5-carboxyfluorescein diacetate, 4-chloro-1-naphthol, chromomycin-$A_3$, DTAF, DTNB, ethidium bromide, fluorescein-5-maleimide diacetate, mithramycin A, rhodamine 123, SBFI, SIST, tetramethylbenzidine, tetramethyl purpurate, thiazolyl blue, TRITC, and the like. Fluorescein may be fluorescein isothiocyanate. The fluorescein isothiocyanate, includes, inter alia, fluorescein isothiocyanate albumin, fluorescein isothiocyanate antibody conjugates, fluorescein isothiocyanate α-bungarotoxin, fluorescein isothiocyanate- casein, fluorescein isothiocyanate-dextrans, fluorescein isothiocyanate—insulin, fluorescein isothiocyanate—Lectins, fluorescein isothiocyanate—peroxidase, and fluorescein isothiocyanate—protein A.

In addition to the therapeutics set forth above, the stabilizing materials of the present invention are particularly useful in connection with ultrasound (US), including diagnostic and therapeutic ultrasound. The stabilizing materials and/or vesicles of the present invention may be used alone, or may be used in combination with various contrast agents, including conventional contrast agents, which may serve to increase their effectiveness as contrast agents for diagnostic imaging.

The present stabilizing materials may also be employed, if desired, in connection with computed tomography (CT) imaging, magnetic resonance imaging (MRI), optical imaging, or other of the various forms of diagnostic imaging that are well known to those skilled in the art. For optical imaging, gas bubbles improve visualization of, for example, blood vessels on the imaging data set. With CT, for example, if a high enough concentration of the present contrast media, and especially gas filled vesicles, is delivered to the region of interest, for example, a blood clot, the clot can be detected on the CT images by virtue of a decrease in the overall density of the clot. In general, a concentration of about 1/10 of 1% of gas filled vesicles or higher (on a volume basis), may be needed to delivered to the region of interest, including the aforementioned blood clot, to be detected by CT.

Examples of suitable contrast agents for use in combination with the present stabilizing materials include, for example, stable free radicals, such as, stable nitroxides, as well as compounds comprising transition, lanthanide and actinide elements, which may, if desired, be in the form of a salt or may be covalently or non-covalently bound to complexing agents, including lipophilic derivatives thereof, or to proteinaceous macromolecules. Preferable transition, lanthanide and actinide elements include, for example, Gd(III), Mn(II), Cu(II), Cr(III), Fe(II), Fe(III), Co(II), Er(II), Ni(II), Eu(III) and Dy(III). More preferably, the elements may be Gd(III), Mn(II), Cu(II), Fe(II), Fe(III), Eu(III) and Dy(III), most preferably Mn(II) and Gd(III). The foregoing elements may be in the form of a salt, including inorganic salts, such as a manganese salt, for example, manganese chloride, manganese carbonate, manganese acetate, and organic salts, such as manganese gluconate and manganese hydroxylapatite. Other exemplary salts include salts of iron, such as iron sulfides, and ferric salts, such as ferric chloride.

The above elements may also be bound, for example, through covalent or noncovalent association, to complexing agents, including lipophilic derivatives thereof, or to proteinaceous macromolecules. Preferable complexing agents include, for example, diethylenetriaminepentaacetic acid (DTPA), ethylene-diaminetetraacetic acid (EDTA), 1,4,7,10-tetraazacyclododecane-N,N',N',N'''-tetraacetic acid (DOTA), 1,4,7,10-tetraazacyclododecane-N,N',N''-triacetic acid (DOTA), 3,6,9-triaza-12-oxa-3,6,9-tricarboxymethylene-10-carboxy-13-phenyl-tridecanoic acid (B-19036), hydroxybenzyl-ethylenediamine diacetic acid (HBED), N,N'-bis(pyridoxyl-5-phosphate)ethylene diamine, N,N'-diacetate (DPDP), 1,4,7-triazacyclononane-N,N',N''-triacetic acid (NOTA), 1,4,8,11-tetraazacyclotetradecane-N,N',N'',N'''-tetraacetic acid (TETA), kryptands (macrocyclic complexes), and desferrioxamine. More preferably, the complexing agents are EDTA, DTPA, DOTA, DO3A and kryptands, most preferably DTPA. Preferable lipophilic complexes include alkylated derivatives of the complexing agents EDTA, DOTA, for example, N,N'-bis-(carboxydecylamidomethyl-N-2,3-dihydroxypropyl)ethylenediamine-N,N'-diacetate (EDTA-DDP); N,N'-bis-(carboxyoctadecylamido-methyl-N-2,3-dihydroxypropyl)ethylenediamine-N,N'-diacetate (EDTA-ODP); and N,N'-Bis(carboxy-laurylamidomethyl-N-2,3-dihydroxypropyl)ethylenediamine-N,N'-diacetate (EDTA-LDP); including those described in U.S. Pat. No. 5,312,617, the disclosure of which is hereby incorporated herein by reference in its entirety. Preferable proteinaceous macromolecules include, for example, albumin, collagen, polyarginine, polylysine, polyhistidine, γ-globulin and β-globulin, with albumin, polyarginine, polylysine, and polyhistidine being more preferred. Suitable complexes therefore include Mn(II)-DTPA, Mn(II)-EDTA, Mn(II)-DOTA, Mn(II)-DO3A, Mn(II)-kryptands, Gd(III)-DTPA, Gd(III)-DOTA, Gd(III)-DO3A, Gd(III)-kryptands, Cr(III)-EDTA, Cu(II)-EDTA, or iron-desferrioxamine, more preferably Mn(II)-DTPA or Gd(III)-DTPA.

Nitroxides are paramagnetic contrast agents which increase both T1 and T2 relaxation rates on MRI by virtue of the presence of an unpaired electron in the nitroxide molecule. As known to one of ordinary skill in the art, the paramagnetic effectiveness of a given compound as an MRI contrast agent may be related, at least in part, to the number of unpaired electrons in the paraniagnetic nucleus or molecule, and specifically, to the square of the number of unpaired electrons. For example, gadolinium has seven unpaired electrons whereas a nitroxide molecule has one unpaired electron. Thus, gadolinium is generally a much stronger MRI contrast agent than a nitroxide. However, effective correlation time, another important parameter for assessing the effectiveness of contrast agents, confers potential increased relaxivity to the nitroxides. When the tumbling rate is slowed, for example, by attaching the paramagnetic contrast agent to a large molecule, it will tumble more slowly and thereby more effectively transfer energy to hasten relaxation of the water protons. In gadolinium, however, the electron spin relaxation time is rapid and will limit the extent to which slow rotational correlation times can increase relaxivity. For nitroxides, however, the electron spin correlation times are more favorable and tremendous increases in relaxivity may be attained by slowing the rotational correlation time of these molecules. The gas filled vesicles of the present invention are ideal for attaining the goals of slowed rotational correlation times and resultant improvement in relaxivity. Although not intending to be bound by any particular- theory of operation, it is contemplated that since the nitroxides may be designed to coat the perimeters of the vesicles, for example, by making alkyl derivatives thereof, the resulting correlation times can be optimized. Moreover, the resulting contrast medium of the present invention may be viewed as a magnetic sphere, a geometric configuration which maximizes relaxivity.

Exemplary superparamagnetic contrast agents suitable for use in the compositions of the present invention include metal oxides and sulfides which experience a magnetic domain, ferro- or ferrimagnetic compounds, such as pure iron, magnetic iron oxide, such as magnetite, $\gamma$-$Fe_2O_3$, $Fe_3O_4$, manganese ferrite, cobalt ferrite and nickel ferrite. Paramagnetic gases can also be employed in the present compositions, such as oxygen 17 gas ($^{17}O_2$). In addition, hyperpolarized xenon, neon, or helium gas may also be employed. MR whole body imaging may then be employed to rapidly screen the body, for example, for thrombosis, and ultrasound may be applied, if desired, to aid in thrombolysis.

The contrast agents, such as the paramagnetic and superparamagnetic contrast agents described above, may be employed as a component within the lipid and/or vesicle compositions. In the case of vesicle compositions, the aforementioned contrast agents may be entrapped within the internal void thereof, administered as a solution with the vesicles, incorporated with any additional stabilizing materials, or coated onto the surface or membrane of the vesicle. Mixtures of any one or more of the paramagnetic agents and/or superparamagnetic agents in the present compositions may be used. The paramagnetic and superparamagnetic agents may also be coadministered separately, if desired.

If desired, the paramagnetic or superparamagnetic agents may be delivered as alkylated or other derivatives incorporated into the compositions, especially the lipidic walls of the vesicles. In particular, the nitroxides 2,2,5,5-tetramethyl-1-pyrrolidinyloxy, free radical and 2,2,6,6-tetramethyl-1-piperidinyloxy, free radical, can form adducts with long chain fatty acids at the positions of the ring which are not occupied by the methyl groups via a variety of linkages, including, for example, an acetyloxy linkage. Such adducts are very amenable to incorporation into the lipid and/or vesicle compositions of the present invention.

The stabilizing materials and/or vesicles of the present invention, and especially the vesicles, may serve not only as effective carriers of the superparamagnetic agents described above, but also may improve the effect of the susceptibility contrast agents. Superparamagnetic contrast agents include metal oxides, particularly iron oxides but including manganese oxides, and as iron oxides, containing varying amounts of manganese, cobalt and nickel which experience a magnetic domain. These agents are nano or microparticles and have very high bulk susceptibilities and transverse relaxation rates. The larger particles, for example, particles having diameters of about 100 nm, have much higher R2 relaxivities as compared to R1 relaxivities. The smaller particles, for example, particles having diameters of about 10 to about 15 nm, have somewhat lower R2 relaxivities, but much more balanced R1 and R2 values. Much smaller particles, for example, monocrystalline iron oxide particles having diameters of about 3 to about 5 nm, have lower R2 relaxivities, but probably the most balanced R1 and R2 relaxation rates. Ferritin can also be formulated to encapsulate a core of very high relaxation rate superparamagnetic iron. It has been discovered that the lipid and/or vesicle compositions, especially vesicle compositions, including gas filled vesicles, can increase the efficacy and safety of these conventional iron oxide based MRI contrast agents.

The iron oxides may simply be incorporated into the stabilizing materials and/or vesicles. Preferably, in the case of vesicles formulated from lipids, the iron oxides may be incorporated into the walls of the vesicles, for example, by being adsorbed onto the surfaces of the vesicles, or entrapped within the interior of the vesicles as described in U.S. Pat. No. 5,088,499, the disclosure of which is hereby incorporated herein by reference in its entirety.

Without being bound to any particular theory or theories of operation, it is believed that the vesicles of the present invention increase the efficacy of the superparamagnetic contrast agents by several mechanisms. First, it is believed that the vesicles function to increase the apparent magnetic concentration of the iron oxide particles. Also, it is believed that the vesicles increase the apparent rotational correlation time of the MRI contrast agents, including paramagnetic and superparamagnetic agents, so that relaxation rates are increased. In addition, the vesicles appear to increase the apparent magnetic domain of the contrast medium according to the manner described hereinafter.

Certain of the vesicles of the present invention, and especially vesicles formulated from lipids, may be visualized as flexible spherical domains of differing susceptibility from the suspending medium, including, for example, the aqueous suspension of the contrast medium or blood or other body fluids, for example, in the case of intravascular injection or injection into other body locations. In the case of ferrites or iron oxide particles, it should be noted that the contrast provided by these agents is dependent on particle size. This phenomenon is very common and is often referred to as the "secular" relaxation of the water molecules. Described in more physical terms, this relaxation mechanism is dependent upon the effective size of the molecular complex in which a paramagnetic atom, or paramagnetic molecule, or molecules, may reside. One physical explanation may be described in the following Solomon-Bloembergen equations which define the paramagnetic contributions as a function of the $T_1$ and $T_2$ relaxation times of a spin ½ nucleus with gyromagnetic ratio g perturbed by a paramagnetic ion:

$1/T_1M=(2/15)S(S+1)\gamma^2g^2\beta^2/r^6[3\ \tau_c/(1+\omega_I^2\tau_c^2)+7\ \tau_c/(1+\omega_s^2\tau_c^2)]+(2/3)S(S+1)A^2/h^2[\tau_c/(1+\omega_s2\ \tau_e^2)]$ and $1/T_2M=(1/15)S(S+1)\gamma^2g^2\beta^2/r^6[4\ \tau_c+3\tau c/(1+\omega_I^2\tau_c^2)\ ^{+}13\ \tau_c/(1+w_s^2\tau_c^2)]+(1/3)S(S+1)A^2/h^2[\tau_I/(1+\omega_s2\ \tau_I^2)]$ where: S is the electron spin quantum number; g is the electronic g factor; β is the Bohr magneton; $\omega_I$ and $\omega_s$ (657 $w_I$) is the Larmor angular precession frequencies for the nuclear spins and electron spins; r is the ion-nucleus distance; A is the hyperfme coupling constant; $\tau_c$ and $\tau_e$ are the correlation times for the dipolar and scalar interactions, respectively; and h is Planck's constant. See, e.g., Solomon, I., *Phys. Rev.* Vol. 99, p. 559 (1955) and Bloembergen, N. *J. Chem. Phys.* Vol. 27, pp. 572, 595 (1957), the disclosures of each of which are hereby incorporated herein by reference in their entirety.

A few large particles may have a much greater effect than a larger number of much smaller particles, primarily due to a larger correlation time. If one were to make the iron oxide particles very large however, increased toxicity may result, and the lungs may be embolized or the complement cascade system may be activated. Furthermore, it is believed that the total size of the particle is not as important as the diameter of the particle at its edge or outer surface. The domain of magnetization or susceptibility effect falls off exponentially from the surface of the particle. Generally speaking, in the case of dipolar (through space) relaxation mechanisms, this exponential fall off exhibits an $r^6$ dependence for a paramagnetic dipole-dipole interaction. Interpreted literally, a water molecule that is 4 angstroms away from a paramagnetic surface will be influenced 64 times less than a water molecule that is 2 angstroms away from the same paramagnetic surface. The ideal situation in terms of maximizing the contrast effect would be to make the iron oxide particles hollow, flexible and as large as possible. It has not been possible to achieve this heretofore and it is believed that the benefits have been unrecognized heretofore also. By coating the inner or outer surfaces of the vesicles with the contrast agents, even though the individual contrast agents, for example, iron oxide nanoparticles or paramagnetic ions, are relatively small structures, the effectiveness of the contrast agents may be greatly enhanced. In so doing, the contrast agents may function as an effectively much larger sphere wherein the effective domain of magnetization is determined by the diameter of the vesicle and is maximal at the surface of the vesicle. These agents afford the advantage of flexibility, namely, compliance. While rigid vesicles might lodge in the lungs or other organs and cause toxic reactions, these flexible vesicles slide through the capillaries much more easily.

In contrast to the flexible vesicles described above, it may be desirable, in certain circumstances, to formulate vesicles from substantially impermeable polymeric materials including, for example, polymethyl methacrylate. This would generally result in the formation of vesicles which may be substantially impermeable and relatively inelastic and brittle. In embodiments involving diagnostic imaging, for example, ultrasound, contrast media which comprise such brittle vesicles would generally not provide the desirable reflectivity that the flexible vesicles may provide. However, by increasing the power output on ultrasound, the brittle microspheres can be made to rupture, thereby causing acoustic emissions which can be detected by an ultrasound transducer.

Nuclear Medicine Imaging (NMI) may-also be used in connection with the diagnostic and therapeutic method aspects of the present invention. For example, NMI may be used to detect radioactive gases, such as $Xe^{133}$, which may be incorporated in the present compositions in addition to, or instead of, the gases discussed above. Such radioactive gases may be entrapped within vesicles for use in detecting, for example, thrombosis. Preferably, bifunctional chelate derivatives are incorporated in the walls of vesicles, and the resulting vesicles may be employed in both NMI and ultrasound. In this case, high energy, high quality nuclear medicine imaging isotopes, such as technetium$^{99m}$ or indium$^{111}$ can be incorporated in the walls of vesicles. Whole body gamma scanning cameras can then be employed to rapidly localize regions of vesicle uptake in vivo. If desired, ultrasound may also be used to confirm the presence, for example, of a clot within the blood vessels, since ultrasound generally provides improved resolution as compared to nuclear medicine techniques. NMI may also be used to screen the entire body of the patient to detect areas of vascular thrombosis, and ultrasound can be applied to these areas locally to promote rupture of the vesicles and treat the clot.

For optical imaging, optically active gases, such as argon or neon, may be incorporated in the present compositions. In addition, optically active materials, for example, fluorescent materials, including porphyrin derivatives, may also be used. Elastography is an imaging technique which generally employs much lower frequency sound, for example, about 60 KHz, as compared to ultrasound which can involve frequencies of over 1 MHz. In elastography, the sound energy is generally applied to the tissue and the elasticity of the tissue may then be determined. In connection with preferred embodiments of the invention, which involve highly elastic vesicles, the deposition of such vesicles onto, for example, a clot, increases the local elasticity of the tissue and/or the space surrounding the clot. This increased elasticity may then be detected with elastography. If desired, elastography can be used in conjunction with other imaging techniques, such as MRI and ultrasound.

Gases and Gaseous Precursors

The present targeted therapeutic delivery systems preferably comprise a gas, such as an inert gas. The gas provides the targeted therapeutic delivery systems with enhanced reflectivity, particularly in connection with targeted therapeutic delivery systems in which the gas is entrapped within the carrier. This may increase their effectiveness as contrast agents or delivery vehicles.

Preferred gases are inert and biocompatible, and include, for example, air, noble gases, such as helium, rubidium, hyperpolarized xenon, hyperpolarized argon, hyperpolarized helium, necn, argon, xenon, carbon dioxide, nitrogen, fluorine, oxygen, sulfur-based gases, such as sulfur hexafluoride and sulfur tetrafluoride, fluorinated gases, including, for example, partially fluorinated gases or completely fluorinated gases, and mixtures thereof Exemplary fluorinated gases include fluorocarbon gases, such as perfluorocarbon gases and mixtures thereof. Paramagnetic gases, such as $^{17}O_2$ may also be used in the stabilizing materials and vesicles.

In certain preferred embodiments, a gas, for example, air or a perfluorocarbon gas, is combined with a liquid perfluorocarbon, such as perfluoropentane, perfluorohexane, perfluoroheptane, perfluorodecalin, perfluorododecalin, perfluorooctyliodide, perfluorooctylbromide, perfluorotripropylamine and perfluorotributylamine.

It may also be desirable to incorporate a precursor to a gaseous substance in the compositions of the present invention. Such precursors include materials that are capable of being converted to a gas in vivo, preferably where the gaseous precursor and gas produced are biocompatible.

Although a gas is preferred, liquid perfluorocarbons and liquid perfluoroethers add desirable properties such as fusogenicity (e.g., ability to fuse or tendency to bind to a membrane) and effectiveness to the resultant therapeutic delivery vehicles.

Among the gaseous precursors which are suitable for use in the compositions described herein are agents which are sensitive to pH. These agents include materials that are capable of evolving gas, for example, upon being exposed to a pH that is neutral or acidic. Examples of such pH sensitive agents include salts of an acid which is selected from the group consisting of inorganic acids, organic acids and mixtures thereof. Carbonic acid ($H_2CO_3$) is an example of a suitable inorganic acid, and aminomalonic acid is an example of a suitable organic acid. Other acids, including inorganic and organic acids, would be readily apparent to one skilled in the art in view of the present disclosure.

Gaseous precursors derived from salts are preferably selected from the group consisting of alkali metal salts, ammonium salts and mixtures thereof. More preferably, the salt is selected from the group consisting of carbonate, bicarbonate, sesquecarbonate, aminomalonate and mixtures thereof. Examples of suitable gaseous precursor materials which are derived from salts include, for example, lithium carbonate, sodium carbonate, potassium carbonate, lithium bicarbonate, sodium bicarbonate, potassium bicarbonate, magnesium carbonate, calcium carbonate, magnesium bicarbonate, ammonium carbonate, ammonium bicarbonate, ammonium sesquecarbonate, sodium sesquecarbonate, sodium aminomalonate and ammonium aminomalonate. Aminomalonate is well known in the art, and its preparation is described, for example, in Thanassi, *Biochemistry*, 9(3):525–532 (1970); Fitzpatrick et al., *Inorganic Chemistry*, 13(3):568–574 (1974); and Stelmashok et al., *Koordinatsionnaya Khimiya*, 3(4):524–527 (1977), the disclosures of which are hereby incorporated herein by reference in their entirety.

In addition to, or instead of, being sensitive to changes in pH, the gaseous precursor materials may also comprise compounds which are sensitive to changes in temperature.

Exemplary of suitable gaseous precursors which are sensitive to changes in temperature are the perfluorocarbons. As the artisan will appreciate, a particular perfluorocarbon may exist in the liquid state when the lipid compositions are first made, and are thus used as a gaseous precursor. Alternatively, the perfluorocarbon may exist in the gaseous state when the lipid compositions are made, and are thus used directly as a gas. Whether the perfluorocarbon is used as a liquid or a gas generally depends on its liquid/gas phase transition temperature; or boiling point. For example, a preferred perfluorocarbon, perfluoropentane, has a liquid/gas phase transition temperature (boiling point) of 29.5° C. This means that perfluoropentane is generally a liquid at room temperature (about 25° C.), but is converted to a gas within the human body, the normal temperature of which is about 37° C., which is above the transition temperature of perfluoropentane. Thus, under normal circumstances, perfluoropentane is a gaseous precursor. As a further example, there are the homologs of perfluoropentane, namely perfluorobutane and perfluorohexane. The liquid/gas transition of perfluorobutane is 4° C. and that of perfluorohexane is 57° C. Thus, perfluorobutane can be useful as a gaseous precursor, although more likely as a gas, whereas perfluorohexane can be useful as a gaseous precursor because of its relatively high boiling point. As known to one of ordinary skill in the art, the effective boiling point of a substance may be related to the pressure to which that substance is exposed. This relationship is exemplified by the ideal gas law: $PV=nRT$, where P is pressure, V is volume, n is moles of substance, R is the gas constant, and T is temperature. The ideal gas law indicates that as pressure increases, the effective boiling point increases also. Conversely, as pressure decreases, the effective boiling point decreases.

A wide variety of materials can be used as liquids, gases and gaseous precursors for entrapping within the carriers. For gaseous precursors, it is only required that the material be capable of undergoing a phase transition to the gas phase upon passing through the appropriate temperature. Exemplary gases and gaseous precursors for use in the present invention include, for example, hexafluoroacetone, isopropyl acetylene, allene, tetrafluoroallene, boron trifluoride, 1,2-butadiene, 2,3-butadiene, 1,3-butadiene, 1,2,3-trichloro-2-fluoro-1,3-butadiene, 2-methyl-1,3-butadiene, hexafluoro-1,3-butadiene, butadiene, 1-fluorobutane, 2-methylbutane, perfluorobutane, decafluorobutane, 1-butene, 2-butene, 2-methyl-1-butene, 3-methyl-1-butene, perfluoro-1-butene, perfluoro-2-butene, 4-phenyl-3-butene-2-one, 2-methyl-1-butene-3-yne, butyl nitrate, 1-butyne, 2-butyne, 2-chloro-1,1,1,4,4,4-hexafluorobutyne, 3-methyl-1-butyne, perfluoro-2-butyne, 2-bromobutyraldehyde, carbonyl sulfide, crotononitrile, cyclobutane, methylcyclobutane, octafluorocyclobutane, perfluorocyclobutene, 3-chlorocyclopentene, perfluorocyclopentane, octafluorocyclopentene, cyclopropane, perfluorocyclopropane, 1,2-dimethylcyclopropane, 1,1-dimethylcyclopropane, 1,2-dimethylcyclopropane, ethylcyclo-propane, methylcyclopropane, diacetylene, 3-ethyl-3-methyl diaziridine, 1,1,1-trifluoro-diazoethane, dimethylamine, hexafluorodimethylamine, dimethylethylamine, bis(dimethyl-phosphine)amine, perfluoroethane, perfluoropropane, perfluoropentane, perfluorohexane, perfluoroheptane, perfluorooctane, perfluorononane, perfluorodecane, hexafluoroethane, hexafluoropropylene, octafluoropropane, octafluorocyclopentene, 1,1-dichlorofluoroethane, hexafluoro-2-butyne, octafluoro-2-butene, hexafluorobuta-1,3-diene, 2,3-dimethyl-2-norborane, perfluorodimethylamine, dimethyloxonium chloride, 1,3-dioxolane-2-one, 4-methyl-1,1,1,2-tetrafluoroethane, 1,1,1-trifluoroethane, 1,1,2,2-tetrafluoroethane, 1,1,2-trichloro-1,2,2-trifluoroethane, 1,1-dichloroethane, 1,1-dichloroethylene, 1,1-dichloro-1,2-difluoroethylene, 1,1-dichloro-1,2,2,2-tetrafluoroethane, 1,2-difluoroethane, 1-chloro-1,1,2,2,2-pentafluoroethane, 2-chloro-1,1-difluoroethane, 1,1-dichloro-2-fluoroethane, 1-chloro-1,1,2,2-tetrafluoroethane, 2-chloro-1,1-difluoroethane, chloroethane, chloropentafluoroethane, dichlorotrifluoroethane, fluoroethane, nitropenta-fluoroethane, nitrosopentafluoroethane, perfluoroethylamine, ethyl vinyl ether, 1,1-dichloroethane, 1,1-dichloro-1,2-difluoroethane, 1,2-difluoroethane, 1,2-difluoroethylene, methane, trifluoromethanesulfonylchloride, trifluoromethanesulfenylchloride, (pentafluorothio)-trifluoromethane, trifluoromethanesulfonylfluoride, bromodifluoronitrosomethane, bromofluoromethane, bromochlorofluoromethane, bromotrifluoromethane, chlorodifluoronitromethane, chlorodinitromethane, chlorofluoromethane, chlorotrifluoromethane, chlorodifluoromethane, dibromodifluoromethane, dichlorodifluoromethane, dichlorofluoromethane, difluoromethane, difluoroiodomethane, disilanomethane, fluoromethane, perfluoromethane, iodomethane, iodotrifluoromethane, nitrotrifluoromethane, nitrosotrifluoromethane, tetrafluoromethane, trichlorofluoromethane, trifluoromethane, 2-methylbutane, methyl ether, methyl isopropyl ether, methyllactate, methylnitrite, methylsulfide, methyl vinyl ether, neon, neopentane, nitrogen, nitrous oxide, 1,2,3-nonadecanetricarboxylic acid 2-hydroxytrimethyl ester, 1-nonene-3-yne, oxygen, 1,4-pentadiene, n-pentane, perfluoropentane, 4-amino-4-methylpentan-2-one, 1-pentene, 2-pentene (cis and trans), 3-bromopent-1-ene, perfluoropent-1-ene, tetrachlorophthalic acid, 2,3,6-trimethyl-piperidine, propane, 1,1,1,2,2,3-hexafluoropropane, 1,2-epoxypropane, 2,2-difluoropropane, 2-aminopropane, 2-chloropropane, heptafluoro-1-nitropropane, heptafluoro-1-nitrosopropane, perfluoropropane, propene, hexafluoropropane, 1,1,1,2,3,3-hexafluoro-2,3-dichloropropane, 1-chloropropane, 1-chloropropylene, chloropropylene-(trans), chloropropane-(trans), 2-chloropropane, 2-chloropropylene, 3-fluoropropane, 3-fluoropropylene, perfluoropropylene, perfluorotetrahydropyran, perfluoromethyltetrahydrofuran, perfluorobutylmethylether, perfluoromethylpentylether, propyne, 3,3,3-trifluoropropyne, 3-fluorostyrene, sulfur (di)-decafluoride ($S_2F_{10}$), sulfur hexafluoride, 2,4-diaminotoluene, trifluoroacetonitrile, trifluoromethyl peroxide, trifluoromethyl sulfide, tungsten hexafluoride, vinyl acetylene, vinyl ether, xenon, 1-bromononafluorobutane, and perfluoroethers.

Preferred gases and gaseous precursors are compounds which are sparingly soluble in water but which may, in some cases, be liposoluble, such as low molecular weight alkanes and their fluorinated analogs. Preferred gases and gaseous precursors include, for example, nitrogen, perfluorocarbons, sulfur hexafluoride, perfluoroether compounds and combinations thereof. The perfluorocarbons and perfluoroethers preferably have from 1 to 4 carbon atoms and from 4 to 10 fluorine atoms, most preferably perfluorobutane ($C_4F_{10}$). Preferred gaseous precursors generally have from about 4 to 8 carbon atoms, more preferably 5 or 6 carbon atoms, and from about 12 to 15 fluorine atoms. Perfluoroethers generally contain one or two oxygen atoms, preferably one oxygen atom. Preferred gaseous precursors include perfluoropentane, perfluorohexane, perfluorodecalin, perfluorotripropylamine, perfluorooctylbromide, perfluorobutylmethylether, perfluorotetrahydropyran, perfluoromethyltetrahydrofuran, perfluoromethylpentylether and other perfluoroether analogues containing between 4 and 6 carbon atoms, and optionally containing one halide ion, preferably $Br^{1-}$. For example, compounds having the structure $C_nF_yH_xOBr$, wherein n is an integer from 1 to 6, y is an integer from 0 to 13, and x is an integer from 0 to 13, are useful as gaseous precursors. Examples of useful gaseous precursors having this formula include perfluoropropyloxylbromide and 2-bromooxyperfluoropropane.

Also useful as gaseous precursors in the present invention are partially or fully fluorinated ethers, preferably having a boiling point of from about 36° C. to about 60° C. Fluorinated ethers are ethers in which one or more hydrogen atoms is replaced by a fluorine atom. For purposes of this invention, fluorinated ethers have the general formula $CX_3(CX_2)_n$—O—$(CX_2)_nCX_3$, wherein X is H, F or another halogen provided that at least one of X is fluorine. Generally, fluorinated ethers containing about 4 to about 6 carbon atoms will have a boiling point within the preferred range for the invention, although smaller or larger chain fluorinated ethers may also be employed in appropriate circumstances. Exemplary fluorinated ethers include compounds having the formulae $CF_3CF_2OCF_2CF_3$, $CF_3O(CF_2)_2CF_3$ and $CF_3OCF(CF_3)_2$.

In preferred embodiments, the gas comprises a fluorinated gas, which includes gases containing one or more than one fluorine atom. Preferred are gases which contain more than one fluorine atom, with perfluorocarbons (fully fluorinated fluorocarbons) being more preferred. The perfluorocarbon gas may be saturated, unsaturated or cyclic, including, for example, perfluoromethane, perfluoroethane, perfluoropropane, perfluorocyclopropane, perfluorobutane, perfluorocyclobutane, perfluoropentane, perfluorocylcopentane, perfluorohexane, perfluoroheptane, perfluorooctane, perfluorononane, and mixtures thereof More preferably, the perfluorocarbon gas is perfluoropropane or perfluorobutane, with perfluoropropane being particularly preferred. Another preferable gas is sulfur hexafluoride. Yet another preferable gas is heptafluoropropane, including 1,1,1,2,3,3,3-heptafluoropropane and its isomer, 1,1,2,2,3,3,3-heptafluoropropane. Mixtures of different types of gases, such as mixtures of a perfluorocarbon gas and another type of gas, such as, for example, air or nitrogen, can also be used in the compositions of the present invention. Other gases, including the gases exemplified above, would be apparent to one skilled in the art in view of the present disclosure.

The gaseous precursor materials may be also photoactivated materials, such as a diazonium ion and aminomalonate. As discussed more fully hereinafter, certain carriers, particularly vesicles, may be formulated so that gas is formed at the target tissue or by the action of sound on the carrier. Examples of gaseous precursors are described, for example, in U.S. Pat. Nos. 5,088,499 and 5,149,319, the disclosures of each of which are hereby incorporated herein by reference in their entirety. Other gaseous precursors, in addition to those exemplified above, will be apparent to one skilled in the art in view of the present disclosure.

The gases and/or gaseous precursors are preferably incorporated in the targeted therapeutic delivery systems irrespective of the physical nature of the composition. Thus, it is contemplated that the gases and/or gaseous precursors may be incorporated, for example, in a surfactant randomly, such as emulsions, dispersions or suspensions, as well as in carriers, including vesicles which are formulated from lipids, such as micelles and liposomes. Incorporation of the gases and/or gaseous precursors in the surfactant may be achieved by using any of a number of methods. For example, in the case of vesicles based on lipids, the formation of gas filled vesicles can be achieved by shaking or otherwise agitating an aqueous mixture which comprises a gas and/or gaseous precursor and one or more lipids. This promotes the formation of stabilized vesicles within which the gas and/or gaseous precursor is encapsulated.

In addition, a gas may be bubbled directly into an aqueous mixture of surfactant. Alternatively, a gas instillation method can be used as disclosed, for example, in U.S. Pat. Nos. 5,352,435 and 5,228,446, the disclosures of each of which are hereby incorporated herein by reference in their entirety. Suitable methods for incorporating the gas and/or gaseous precursor in cationic lipid compositions are disclosed also in U.S. Pat. No. 4,865,836, the disclosure of which is hereby incorporated herein by reference in its entirety. Other methods would be apparent to one skilled in the art based on the present disclosure. Preferably, the gas may be instilled in the surfactant after or during the addition of the surfactant, and/or during formation of compositions of the present invention.

Embodiments include the gases and/or gaseous precursors incorporated in vesicle compositions, with micelles and liposomes being preferred. Vesicles in which a gas or gaseous precursor or both are encapsulated are advantageous in that they provide improved reflectivity in vivo.

It is preferred that the surfactant, be formulated from lipids and optional stabilizing compounds to promote the formation of stable vesicles, as discussed in detail above. Additionally, it is preferred that the surfactant comprise a highly stable gas as well. The phrase "highly stable gas" refers to a gas which has limited solubility and diffusability in aqueous media. Exemplary highly stable gases include perfluorocarbons since they are generally less diffusible and relatively insoluble in aqueous media. Accordingly, their use may promote the formation of highly stable vesicles.

Compositions employed herein may also include, with respect to their preparation, formation and use, gaseous precursors that can be activated to change from a liquid or solid state into a gas by temperature, pH, light, and energy (such as ultrasound). The gaseous precursors may be made into gas by storing the precursors at reduced pressure. For example, a vial stored under reduced pressure may create a headspace of perfluoropentane or perfluorohexane gas, useful for creating a preformed gas prior to injection. Preferably, the gaseous precursors may be activated by temperature. Set forth below is a table listing a series of gaseous precursors which undergo phase transitions from liquid to gaseous states at relatively close to normal body temperature (37° C.) or below, and the size of the emulsified droplets that would be required to form a vesicle of a maximum size of 10 $\mu$m.

TABLE 4

Physical Characteristics of Gaseous Precursors and Diameter of Emulsified Droplet to Form a 10 μm Vesicle*

Figure 5:
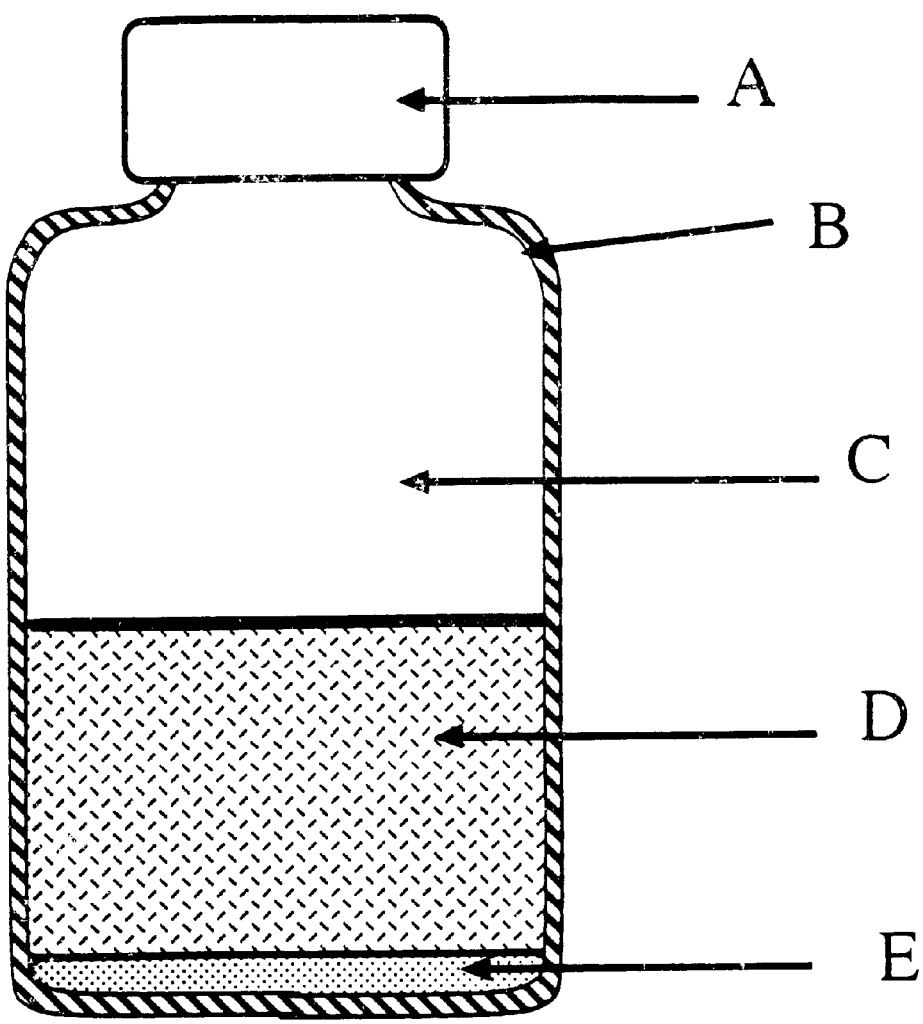
FIG. 5 shows the non-mixed components which form a therapeutic delivery system after mixing.
Figure 6:
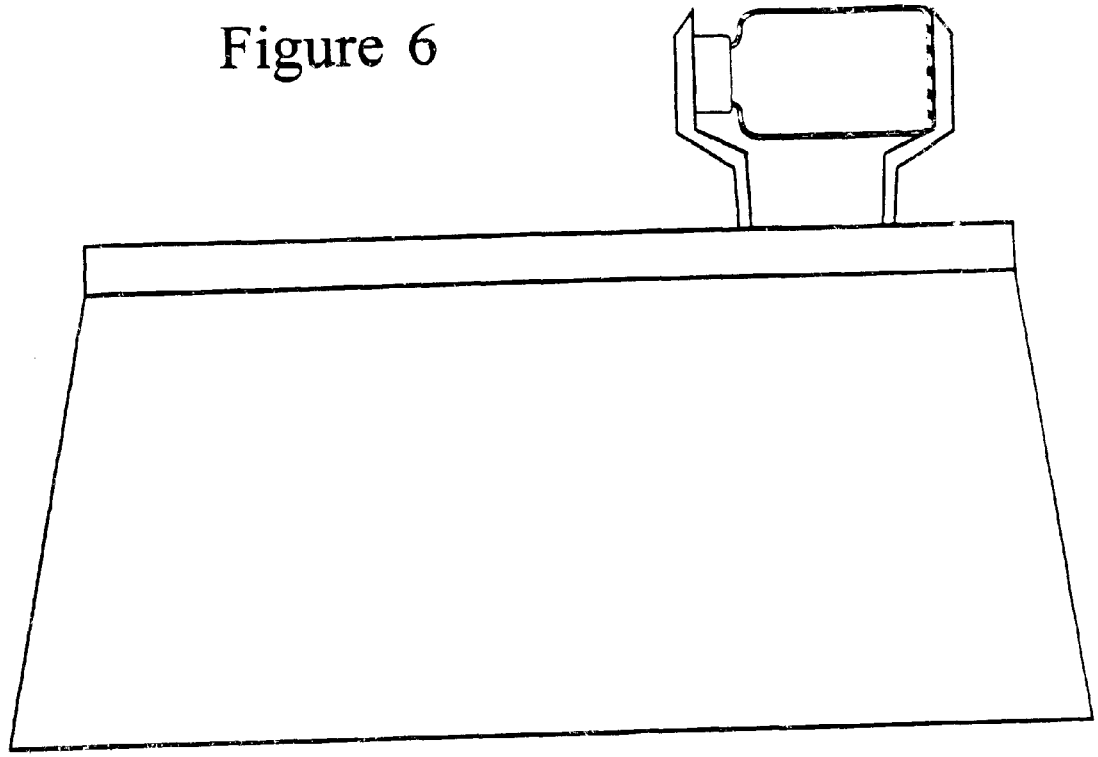
FIG. 6 illustrates the shaker for forming the a therapeutic delivery system in FIG. 5 as well as their pre- and post-shaking appearance.
Figure 6:
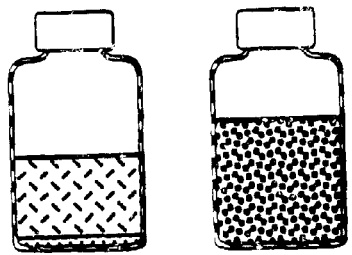

| Compound | Molecular Weight | Boiling Point (° C.) | Density | Diameter (μm) of emulsified droplet to make 10 micron vesicle |
|---|---|---|---|---|
| perfluoro pentane | 288.04 | 28.5 | 1.7326 | 2.9 |
| 1-fluorobutane | 76.11 | 32.5 | 0.67789 | 1.2 |
| 2-methyl butane (isopentane) | 72.15 | 27.8 | 0.6201 | 2.6 |
| 2-methyl 1-butene | 70.13 | 31.2 | 0.6504 | 2.5 |
| 2-methyl-2-butene | 70.13 | 38.6 | 0.6623 | 2.5 |
| 1-butene-3-yne-2-methyl | 66.10 | 34.0 | 0.6801 | 2.4 |
| 3-methyl-1-butyne | 68.12 | 29.5 | 0.6660 | 2.5 |
| octafluoro cyclobutane | 200.04 | −5.8 | 1.48 | 2.8 |
| decafluoro butane | 238.04 | −2 | 1.517 | 3.0 |
| hexafluoro ethane | 138.01 | −78.1 | 1.607 | 2.7 |

*Source: Chemical Rubber Company Handbook of Chemistry and Physics, Robert C. Weast and David R. Lide, eds., CRC Press, Inc. Boca Raton, Florida (1989–1990).

As noted above, it is preferred to optimize the utility of the surfactant, especially vesicles formulated from lipids, by using gases of limited solubility. The phrase "limited solubility" refers to the ability of the gas to diffuse out of the vesicles by virtue of its solubility in the surrounding aqueous medium. A greater solubility in the aqueous medium imposes a gradient with the gas in the vesicle such that the gas may have a tendency to diffuse out of the vesicle. A lesser solubility in the aqueous milieu, may, on the other hand, decrease or eliminate the gradient between the vesicle and the interface such that diffusion of the gas out of the vesicle may be impeded. Preferably, the gas entrapped in the vesicle has a solubility less than that of oxygen, that is, about 1 part gas in about 32 parts water. See *Matheson Gas Data Book*, 1966, Matheson Company Inc. More preferably, the gas entrapped in the vesicle possesses a solubility in water less than that of air; and even more preferably, the gas entrapped in the vesicle possesses a solubility in water less than that of nitrogen.

It may be desirable, in certain embodiments, to formulate vesicles from substantially impermeable polymeric materials. In these embodiments, it is generally unnecessary to employ a gas which is highly insoluble. For example, stable vesicles which comprise substantially impermeable polymeric materials may be formulated with gases having higher solubilities, for example, air or nitrogen.

Methods Of Preparation

The compositions of the present invention may be prepared using any of a variety of suitable methods. These are described below separately for the embodiments involving a targeted therapeutic delivery system comprising an oil, a surfactant, a therapeutic, and a gas, including a gas filled vesicle, and a targeted therapeutic delivery system comprising an oil, a surfactant, a therapeutic, and a gaseous precursor including a gaseous precursor filled vesicle. A targeting ligand may be attached to the surfactant of the targeted therapeutic delivery system by bonding to one or more of the materials employed in the compositions from which they are made, including the steroid prodrugs, lipids, proteins, polymers, and/or auxiliary stabilizing materials.

While not intending to be bound by any particular theory or theories of preparation, it is currently believed that the general principle involves dissolving lipophilic drugs in the oil or wax, with the drug selected from those having octanol/water partition coefficients preferably greater than 2 and even more preferably greater than 10. Most preferred are drugs with partition coefficients greater than 25. Taxol is exemplary of the choice, having a partition coefficient of 99.

After the lipophilic drug is mixed with the oil, it is simply added to or dispersed into an aqueous phase containing one or more surfactants and stabilizing media. As shown in FIG. 5, this may take place in a vial containing the suspending media. The vial is sealed with a head space of a pre-selected gas. The vial is then shaken as detailed in the Examples. This process preferrably results in lipospheres containing crystalized drug and a central gas bubble, see FIG. 2.

In the process of preparing the oil/drug suspension, it is preferred that the solvent be in the liquid state. After the drug crystals are thoroughly mixed into the solvent, preferably also with gas, the temperature may be lowered to emulsify or solidify the oil to form solid shells entrapping crystalline drug. Preferably the amount of drug is between 0.01% to 90% by weight. More preferably, the drug ranges from 5% to 75% by weight relative to the oil.

It has been discovered that a head space of gas in the vial is of importance. When the vials are agitated mechanically, as in a dental amalgamator, vibrations cause microsphere collapse and rupture. As the microsphere oscillates, the oil surrounding the microsphere is destabilized resulting in release of entrapped drugs. Drug release can be monitored by acoustic activity of the microspheres. As attenuation and backscatter diminish, drug release is verified. Alternatively, subharmonic and ultraharmonic profiles can be monitored to assess drug release.

Preferably the vial contains between 10% and 80% gas by volume and most preferably about 50% to 60% gas by volume. Gas in the head space, in general, results in a significantly more uniform distribution of particle sizes. For example perfluoropropane-instilled canola oil acoustically active lipospheres showed a modal distribution with a median size of 3.87 microns and 85% of the population under 8 microns. Conversely, the same composition liposheres made when the vial is filled without a gaseous headspace showed a relatively flat distribution curve with sizes of particles between 1–10 microns having no discemable peak sizes.

This concept is illustrated in FIGS. 5 and 6. In FIG. 5, the oil is generally immiscible in the aqueous medium. Depending on the density of the aqueous phase, the oil/drug mixture will settle to the bottom, or float to the top; in most instances the hydrophobic phase is denser.

FIG. 6 illustrates an ESPE Capmix Shaking Device containing the vial from FIG. 5. In front of the Camix, vials A and B are shown, where A represents pre-shaken mixture and B represents post-shaking. The contents of vial B appear as a homogeneous foam. The liquid layer has a slightly raised height in the vial due to incorporation of gas in the center of the lipospheres.

A wide variety of such lipid-insoluble drugs may be incorporated into oils. For example, etoposide or bleomycin may be added to soybean oil then subjected to agitation, e.g., in a Waring blender or Silverson mixer. Ball milling may also be employed. One or more emulsifying agents may also be incorporated into the oil, such as phospholipid, fatty acids, polyethylene glycol or other surfactants such as pluronic, Tween, Zonyl, and the like, to aid in preparation of a homogeneous suspension of crystalline drug. Alternatively, the drug may first be dissolved in an aqueous solvent, e.g., water, ethanol, or low boiling azeotropes and mixed with the oil under mechanical agitation. As the pressure is lowered and/or temperature raised, the solvent evaporates, leaving crystals of the drug within the oil or wax phase. The same process may be accomplished in a spray dryer.

Finer-sized crystalline drug emusions can also be prepared by microemulsification as in, for example, a microfluidizer. Note that viscous oils or oils with melting points above about 20° C. can be used to prepare stable dispersions of crystallized drugs in oil. Preferably the final form of the drug in oil is then placed in a vial as shown in FIG. 5 and shaken in the amalgamator.

A wide variety of methods are available for the preparation of the targeted therapeutic delivery system including vesicles, such as micelles and/or liposomes. Included among these methods are, for example, shaking, drying, gas-installation, spray drying, and the like. Suitable methods for preparing vesicle compositions are described, for example, in U.S. Pat. No. 5,469,854, the disclosure of which is hereby incorporated herein by reference in its entirety. The vesicles are preferably prepared from lipids which remain in the gel state.

Micelles may be prepared using any one of a variety of conventional micellar preparatory methods which will be apparent to those skilled in the art. These methods typically involve suspension of the surfactant, such as a lipid compound, in an organic solvent, evaporation of the solvent, resuspension in an aqueous medium, sonication and centrifugation. The foregoing methods, as well as others, are discussed, for example, in Canfield et al., *Methods in Enzymology*, 189:418–422 (1990); El-Gorab et al, *Biochem. Biophys. Acta*, 306:58–66 (1973); *Colloidal Surfactant*, Shinoda, K., Nakagana, Tamamushi and Isejura, Academic Press, NY (1963) (especially "The Formation of Micelles", Shinoda, Chapter 1, pp. 1–88); *Catalysis in Micellar and Macromolecular Systems*, Fendler and Fendler, Academic Press, NY (1975). The disclosures of each of the foregoing publications are hereby incorporated herein by reference in their entirety.

In liposomes, the lipid compound(s) may be in the form of a monolayer or bilayer, and the monolayer or bilayer lipids may be used to form one or more monolayers or bilayers. In the case of more than one monolayer or bilayer, the monolayers or bilayers are generally concentric. Thus, lipids may be used to form unilamellar liposomes (comprised of one monolayer or bilayer), oligolamellar liposomes (comprised of two or three monolayers or bilayers) or multilamellar liposomes (comprised of more than three monolayers or bilayers).

A wide variety of methods are available in connection with the preparation of vesicles, including liposomes. Accordingly, liposomes may be prepared using any one of a variety of conventional liposomal preparatory techniques which will be apparent to those skilled in the art, including, for example, solvent dialysis, French press, extrusion (with or without freeze-thaw), reverse phase evaporation, simple freeze-thaw, sonication, chelate dialysis, homogenization, solvent infusion, microemulsification, spontaneous formation, solvent vaporization, solvent dialysis, French pressure cell technique, controlled detergent dialysis, and others, each involving the preparation of the vesicles in various fashions. See, e.g., Madden et al., *Chemistry and Physics of Lipids*, 53:37–46 (1990), the disclosure of which is hereby incorporated herein by reference in its entirety. Suitable freeze-thaw techniques are described, for example, in International Application Serial No. PCT/US89/05040, filed Nov. 8, 1989, the disclosure of which is hereby incorporated herein by reference in its entirety. Methods which involve freeze-thaw techniques are preferred in connection with the preparation of liposomes. Preparation of the liposomes may be carried out in a solution, such as an aqueous saline solution, aqueous phosphate buffer solution, or sterile water. The liposomes may also be prepared by various processes which involve shaking or vortexing, which may be achieved, for example, by the use of a mechanical shaking device, such as a Wig-L-Bug™ (Crescent Dental, Lyons, Ill.), a Mixomat, sold by Degussa AG, Frankfurt, Germany, a Capmix, sold by Espe Fabrik Pharmazeutischer Praeparate GMBH & Co., Seefeld, Oberay Germany, a Silamat Plus, sold by Vivadent, Lechtenstein, or a Vibros, sold by Quayle Dental, Sussex, England. Conventional microemulsification equipment, such as a Microfluidizer™ (Microfluidics, Woburn, Mass.) may also be used.

Spray drying may be employed to prepare gas filled vesicles. Utilizing this procedure, the stabilizing materials, such as lipids, may be pre-mixed in an aqueous environment and then spray dried to produce gas filled vesicles. The vesicles may be stored under a headspace of a desired gas.

Many liposomal preparatory techniques which may be adapted for use in the preparation of vesicle compositions are discussed, for example, in U.S. Pat. Nos. 4,728,578, 4,728,575, 4,737,323, 4,533,254, 4,162,282, 4,310,505, and 4,921,706; U.K. Patent Application GB 2193095 A; International Application Serial No. PCT/US85/01161; Mayer et al., *Biochimica et Biophysica Acta*, 858:161–168 (1986); Hope et al., *Biochimica et Biophysica Acta*, 812:55–65 (1985); Mayhew et al., *Methods in Enzymology*, 149:64–77 (1987); Mayhew et al., *Biochimica et Biophysica Acta*, 755:169–74 (1984); Cheng et al, *Investigative Radiology*, 22:47–55 (1987); International Application Serial No. PCT/US89/05040; and *Liposome Technology*, Gregoriadis, ed., Vol. I, pp. 29–31, 51–67 and 79–108 (CRC Press Inc., Boca Raton, Fla. 1984), the disclosures of each of which are hereby incorporated by reference herein in their entirety.

In connection with stabilizing materials, and especially lipid compositions in the form of vesicles, it may be advantageous to prepare the lipid compositions at a temperature below the gel to liquid crystalline phase transition temperature of the lipids. This phase transition temperature is the temperature at which a lipid bilayer will convert from a gel state to a liquid crystalline state. See, for example, Chapman et al., *J. Biol. Chem.*, 249:2512–2521 (1974), the disclosure of which is hereby incorporated by reference herein in its entirety. It is generally believed that vesicles which are prepared from lipids that possess higher gel state to liquid crystalline state phase transition temperatures tend to have enhanced impermeability at any given temperature. See Derek Marsh, CRC *Handbook of Lipid Bilayers* (CRC Press, Boca Raton, Fla. 1990), at p. 139 for main chain melting transitions of saturated diacyl-sn-glycero-3-phosphocholines. The gel state to liquid crystalline state phase transition temperatures of various lipids will be readily apparent to those skilled in the art and are described, for example, in Gregoriadis, ed., *Liposome Technology*, Vol. I, 1–18 (CRC Press, 1984). The following table lists some of the representative lipids and their phase transition temperatures.

TABLE 5

Saturated Diacyl-sn-Glycero-3-Phosphocholines:
Main Chain Melting Transition Temperatures

| Number of Carbons in Acyl Chains | Main Phase Transition Temperature (° C.) |
|---|---|
| 1,2-(12:0) | −1.0 |
| 1,2-(13:0) | 13.7 |

TABLE 5-continued

Saturated Diacyl-sn-Glycero-3-Phosphocholines:
Main Chain Melting Transition Temperatures

| Number of Carbons in Acyl Chains | Main Phase Transition Temperature (° C.) |
|---|---|
| 1,2-(14:0) | 23.5 |
| 1,2-(15:0) | 34.5 |
| 1,2-(16:0) | 41.4 |
| 1,2-(17:0) | 48.2 |
| 1,2-(18:0) | 55.1 |
| 1,2-(19:0) | 61.8 |
| 1,2-(20:0) | 64.5 |
| 1,2-(21:0) | 71.1 |
| 1,2-(22:0) | 74.0 |
| 1,2-(23:0) | 79.5 |
| 1,2-(24:0) | 80.1 |

See, for example, Derek Marsh, CRC Handbook of Lipid Bilayers, p. 139 (CRC Press, Boca Raton, FL 1990).

Stabilizing materials, such as lipids, comprising a gas can be prepared by agitating an aqueous solution containing, if desired, a stabilizing material, in the presence of a gas. The term "agitating" means any shaking motion of an aqueous solution such that gas is introduced from the local ambient environment into the aqueous solution. This agitation is preferably conducted at a temperature below the gel to liquid crystalline phase transition temperature of the lipid. The shaking involved in the agitation of the solutions is preferably of sufficient force to result in the formation of a lipid composition, including vesicle compositions, and particularly vesicle compositions comprising gas filled vesicles. The shaking may be by swirling, such as by vortexing, side-to-side, or up and down motion. Different types of motion may be combined. Also, the shaking may occur by shaking the container holding the aqueous lipid solution, or by shaking the aqueous solution within the container without shaking the container itself.

The shaking may occur manually or by machine. Mechanical shakers that may be used include, for example, a shaker table such as a VWR Scientific (Cerritos, Calif.) shaker table, as well as any of the shaking devices described hereinbefore, with the Capmix (Espe Fabrik Pharmazeutischer Praeparate GMBH & Co., Seefeld, Oberay, Germany) being preferred. It has been found that certain modes of shaking or vortexing can be used to make vesicles within a preferred size range. Shaking is preferred, and it is preferred that the shaking be carried out using the Espe Capmix mechanical shaker. In accordance with this preferred method, it is preferred that a reciprocating motion be utilized to generate the lipid compositions, and particularly vesicles. It is even more preferred that the motion be reciprocating in the form of an arc. It is contemplated that the rate of reciprocation, as well as the arc thereof, is particularly important in connection with the formation of vesicles. Preferably, the number of reciprocations or full cycle oscillations is from about 1000 to about 20,000 per minute. More preferably, the number of reciprocations or oscillations is from about 2500 to about 8000, with reciprocations or oscillations of from about 3300 to about 5000 being even more preferred. Of course, the number of oscillations can be dependent upon the mass of the contents being agitated. Generally speaking, a larger mass requires fewer oscillations. Another means for producing shaking includes the action of gas emitted under high velocity or pressure.

It will also be understood that preferably, with a larger volume of aqueous solution, the total amount of force will be correspondingly increased. Vigorous shaking is defined as at least about 60 shaking motions per minute, and is preferred. Vortexing at about 60 to about 300 revolutions per minute is more preferred. Vortexing at about 300 to about 1800 revolutions per minute is even more preferred.

In addition to the simple shaking methods described above, more elaborate methods can also be employed. Such elaborate methods include, for example, liquid crystalline shaking gas instillation processes and vacuum drying gas instillation processes, such as those described in U.S. Pat. Nos. 5,469,854, 5,580,575, 5,585,112, and 5,542,935, and U.S. application Ser. No. 08/307,305, filed Sep. 16, 1994, the disclosures of each of which are incorporated herein by reference in their entirety. Emulsion processes may also be employed in the preparation of compositions in accordance with the present invention. Such emulsification processes are described, for example, in Quay, U.S. Pat. Nos. 5,558,094, 5,558,853, 5,558,854, and 5,573,751, the disclosures of each of which are hereby incorporated herein by reference in their entirety. Spray drying may be also employed to prepare the gaseous precursor filled vesicles. Utilizing this procedure, the lipids may be pre-mixed in an aqueous environment and then spray dried to produce gaseous-precursor filled vesicles. The vesicles may be stored under a headspace of a desired gas. Although any of a number of varying techniques can be used, the vesicle compositions employed in the present invention are preferably prepared using a shaking technique. Preferably, the shaking technique involves agitation with a mechanical shaking apparatus, such as an Espe Capmix (Seefeld, Oberay, Germany), using, for example, the techniques disclosed in U.S. application Ser. No. 160,232, filed Nov. 30, 1993, the disclosures of which are hereby incorporated herein by reference in its entirety. In addition, after extrusion and sterilization procedures, which are discussed in detail below, agitation or shaking may provide vesicle compositions which can contain substantially no or minimal residual anhydrous lipid phase in the remainder of the solution. (Bangham, et al, *J. Mol. Biol.* 13:238–252 (1965)). Other preparatory techniques include those described in Unger, U.S. Pat. No. 5,205,290, the disclosure of which is hereby incorporated herein by reference in its entirety.

Foams comprise an additional embodiment of the invention. Foams find biomedical application in implants for local delivery of drugs, tissue augmentation, wound healing, and prevention of peritoneal adhesions. Phospholipid foams can be created by increasing the concentration of the phospholipids as well as by mixing with materials such as cetyl alcohol, surfactants, simethicone or polymers, such as methylcellulose. Fluorinated phospholipids may also be used to create stable, long-lasting foams. The most stable foams are generally prepared from materials which are polymerized or cross-linked, such as polymerizable phospholipids. Since foaming is also a function of surface tension reduction, detergents are generally useful foaming agents.

Foams can also be produced by shaking gas filled vesicles, wherein the foam appears on the top of the aqueous solution, and is coupled with a decrease in the volume of the aqueous solution upon the formation of foam. Preferably, the final volume of the foam is at least about two times the initial volume of the aqueous stabilizing material solution; more preferably, the final volume of the foam is at least about three times the initial volume of the aqueous solution; even more preferably, the final volume of the foam is at least about four times the initial volume of the aqueous solution; and most preferably, all of the aqueous stabilizing material solution is converted to foam.

The required duration of shaking time may be determined by detection of the formation of foam. For example, 10 ml of lipid solution in a 50 ml centrifuge tube may be vortexed for approximately 15–20 minutes or until the viscosity of the gas filled liposomes becomes sufficiently thick so that it no longer clings to the side walls as it is swirled. At this time, the foam may cause the solution containing the gas filled liposomes to raise to a level of 30 to 35 ml.

The concentration of lipid required to form a preferred foam level will vary depending upon the type of lipid used, and may be readily determined by one skilled in the art, in view of the present disclosure. For example, in preferred embodiments, the concentration of 1,2-dipalmitoylphosphatidylcholine (DPPC) used to form gas filled liposomes according to the methods of the present invention is about 20 mg/ml to about 30 mg/ml saline solution. The concentration of distearoylphosphatidylcholine (DSPC) used in preferred embodiments is about 5 mg/ml to about 10 mg/ml saline solution.

Specifically, DPPC in a concentration of 20 mg/ml to 30 mg/ml, upon shaking, yields a total suspension and entrapped gas volume four times greater than the suspension volume alone. DSPC in a concentration of 10 mg/ml, upon shaking, yields a total volume completely devoid of any liquid suspension volume and contains entirely foam.

Microemulsification is a common method of preparing an emulsion of a foam precursor. Temperature increases and/or lowered pressures will cause foaming as gas bubbles form in the liquid. As discussed above, the foam may be stabilized by, for example, surfactants, detergents or polymers.

The size of gas filled vesicles can be adjusted, if desired, by a variety of procedures, including, for example, microemulsification, vortexing, extrusion, filtration, sonication, homogenization, repeated freezing and thawing cycles, extrusion under pressure through pores of defmed size, and similar methods. Gas filled vesicles prepared in accordance with the methods described herein can range in size from less than about 1 $\mu$m to greater than about 100 $\mu$m. In addition, after extrusion and sterilization procedures, which are discussed in detail below, agitation or shaking provides vesicle compositions which provide substantially no or minimal residual anhydrous lipid phase in the remainder of the solution. (Bangham, et al, *J. Mol. Biol.*, 13:238–252 (1965)). If desired, the vesicles of the present invention may be used as they are formed, without any attempt at further modification of the size thereof. For intravascular use, the vesicles preferably have diameters of less than about 30 $\mu$m, and more preferably, less than about 12 $\mu$m. For targeted intravascular use including, for example, binding to certain tissue, such as cancerous tissue, the vesicles can be significantly smaller, for example, less than about 100 nm in diameter. For enteric or gastrointestinal use, the vesicles can be significantly larger, for example, up to a millimeter in size. Preferably, the vesicles are sized to have diameters of from about 2 $\mu$m to about 100 $\mu$m.

The gas filled vesicles may be sized by a simple process of extrusion through filters wherein the filter pore sizes control the size distribution of the resulting gas filled vesicles. By using two or more cascaded or stacked set of filters, for example, a 10 $\mu$m filter followed by an 8 $\mu$m filter, the gas filled vesicles can be selected to have a very narrow size distribution around 7 to 9 $\mu$m. After filtration, these gas filled vesicles can remain stable for over 24 hours.

The sizing or filtration step may be accomplished by the use, for example, of a filter assembly when the composition is removed from a sterile vial prior to use, or more preferably, the filter assembly may be incorporated into a syringe during use. The method of sizing the vesicles will then comprise using a syringe comprising a barrel, at least one filter, and a needle; and will be carried out by an extraction step which comprises extruding the vesicles from the barrel through the filter fitted to the syringe between the barrel and the needle, thereby sizing the vesicles before they are administered to a patient. The extraction step may also comprise drawing the vesicles into the syringe, where the filter will function in the same way to size the vesicles upon entrance into the syringe. Another alternative is to fill such a syringe with vesicles which have already been sized by some other means, in which case the filter now functions to ensure that only vesicles within the desired size range, or of the desired maximum size, are subsequently administered by extrusion from the syringe. In certain preferred embodiments, the vesicle compositions may be heat sterilized or filter sterilized and extruded through a filter prior to shaking. Generally speaking, vesicle compositions comprising a gas may be heat sterilized, and vesicle compositions comprising gaseous precursors may be filter sterilized. Once gas filled vesicles are formed, they may be filtered for sizing as described above. Performing these steps prior to the formation of gas and/or gaseous precursor filled vesicles provide sterile gas and/or gaseous precursor filled vesicles ready for administration to a patient. For example, a mixing vessel such as a vial or syringe may be filled with a filtered lipid composition, and the composition may be sterilized within the mixing vessel, for example, by autoclaving. Gas may be instilled into the composition to form gas filled vesicles by shaking the sterile vessel. Preferably, the sterile vessel is equipped with a filter positioned such that the gas filled vesicles pass through the filter before contacting a patient.

The step of extruding the solution of lipid compound through a filter decreases the amount of unhydrated material by breaking up any dried materials and exposing a greater surface area for hydration. Preferably, the filter has a pore size of about 0.1 to about 5 $\mu$m, more preferably, about 0.1 to about 4 $\mu$m, even more preferably, about 0.1 to about 2 $\mu$m, and still more preferably, about 1 $\mu$m. Unhydrated compound, which is generally undesirable, appears as amorphous clumps of non-uniform size.

The sterilization step provides a composition that may be readily administered to a patient for diagnostic imaging including, for example, ultrasound or CT. In certain preferred embodiments, sterilization may be accomplished by heat sterilization, preferably, by autoclaving the solution at a temperature of at least about 100° C., and more preferably, by autoclaving at about 100° C. to about 130° C., even more preferably, about 110° C. to about 130° C., still more preferably, about 120° C. to about 130° C., and even more preferably, about 130° C. Preferably, heating occurs for at least about 1 minute, more preferably, about 1 to about 30 minutes, even more preferably, about 10 to about 20 minutes, and still more preferably, about 15 minutes.

If desired, the extrusion and heating steps, as outlined above, may be reversed, or only one of the two steps can be used. Other modes of sterilization may be used, including, for example, exposure to gamma radiation.

In addition to the aforementioned embodiments, gaseous precursors contained in vesicles can be formulated which, upon activation, for example, by exposure to elevated temperature, varying pH, light, or pressure, undergo a phase transition from, for example, a liquid, including a liquid entrapped in a vesicle, to a gas, expanding to create the gas filled vesicles described herein. This technique is described in detail in patent application Ser. No. 08/159,687, filed Nov. 30, 1993, and U.S. Pat. No. 5,542,935, the disclosures of which are hereby incorporated herein by reference in their entirety.

The preferred method of activating the gaseous precursor is by exposure to elevated temperature. Activation or transition temperature, and like terms, refer to the boiling point of the gaseous precursor and is the temperature at which the liquid to gaseous phase transition of the gaseous precursor takes place. Useful gaseous precursors are those materials which have boiling points in the range of about −100° C. to about 70° C. The activation temperature is particular to each gaseous precursor. An activation temperature of about 37° C., or about human body temperature, is preferred for gaseous precursors in the context of the present invention. Thus, in preferred form, a liquid gaseous precursor is activated to become a gas at about 37° C. or below. The gaseous precursor may be in liquid or gaseous phase for use in the methods of the present invention.

The methods of preparing the gaseous precursor filled vesicles may be carried out below the boiling point of the gaseous precursor such that a liquid is incorporated, for example, into a vesicle. In addition, the methods may be conducted at the boiling point of the gaseous precursor, such that a gas is incorporated, for example, into a vesicle. For gaseous precursors having low temperature boiling points, liquid precursors may be emulsified using a microfluidizer device chilled to a low temperature.

The boiling points may also be depressed using solvents in liquid media to utilize a precursor in liquid form. Further, the methods may be performed where the temperature is increased throughout the process, whereby the process starts with a gaseous precursor as a liquid and ends with a gas.

The gaseous precursor may be selected so as to form the gas in situ in the targeted tissue or fluid, in vivo upon entering the patient or animal, prior to use, during storage, or during manufacture. The methods of producing the temperature activated gaseous precursor filled vesicles may be carried out at a temperature below the boiling point of the gaseous precursor. In this embodiment, the gaseous precursor is entrapped within a vesicle such that the phase transition does not occur during manufacture. Instead, the gaseous precursor filled vesicles are manufactured in the liquid phase of the gaseous precursor. Activation of the phase transition may take place at any time as the temperature is allowed to exceed the boiling point of the precursor. Also, knowing the amount of liquid in a droplet of liquid gaseous precursor, the size of the vesicles upon attaining the gaseous state may be determined.

Alternatively, the gaseous precursors may be utilized to create stable gas filled vesicles which are pre-formed prior to use. In this embodiment, the gaseous precursor is added to a container housing a lipid composition at a temperature below the liquid-gaseous phase transition temperature of the respective gaseous precursor. As the temperature is increased, and an emulsion is formed between the gaseous precursor and liquid solution, the gaseous precursor undergoes transition from the liquid to the gaseous state. As a result of this heating and gas formation, the gas displaces the air in the head space above the liquid mixture so as to form gas filled vesicles which entrap the gas of the gaseous precursor, ambient gas (e.g. air), or coentrap gas state gaseous precursor and ambient air. This phase transition can be used for optimal mixing and formation of the contrast agent. For example, the gaseous precursor, perfluorobutane, can be entrapped in the lipid vesicles and as the temperature is raised beyond the boiling point of perfluorobutane (4° C.), perfluorobutane gas is entrapped in the vesicles. Accordingly, the gaseous precursors may be selected to form gas filled vesicles in vivo or may be designed to produce the gas filled vesicles in situ, during the manufacturing process, on storage, or at some time prior to use. A water bath, sonicator or hydrodynamic activation by pulling back the plunger of a syringe against a closed stopcock may be used to activate targeted gas filled vesicles from temperature-sensitive gaseous precursors prior to intravenous injection.

As a further embodiment of this invention, by preforming the gaseous precursor in the liquid state into an aqueous emulsion, the maximum size of the vesicle may be estimated by using the ideal gas law, once the transition to the gaseous state is effectuated. For the purpose of making gas filled vesicles from gaseous precursors, the gas phase is assumed to form instantaneously and substantially no gas in the newly formed vesicle has been depleted due to diffusion into the liquid, which is generally aqueous in nature. Hence, from a known liquid volume in the emulsion, one would be able to predict an upper limit to the size of the gas filled vesicle.

In embodiments of the present invention, a mixture of a lipid compound and a gaseous precursor, containing liquid droplets of defined size, may be formulated such that upon reaching a specific temperature, for example, the boiling point of the gaseous precursor, the droplets will expand into gas filled vesicles of defined size. The defined size represents an upper limit to the actual size because the ideal gas law cannot account for such factors as gas diffusion into solution, loss of gas to the atmosphere, and the effects of increased pressure.

The ideal gas law, which can be used for calculating the increase in the volume of the gas bubbles upon transitioning from liquid to gaseous states, is as follows:

$$PV=nRT$$

where: P is pressure in atmospheres (atm); V is volume in liters (L); n is moles of gas; T is temperature in degrees Kelvin (K); and R is the ideal gas constant (22.4 L-atm/K-mole).

With knowledge of volume, density, and temperature of the liquid in the mixture of liquids, the amount, for example, in moles, and volume of liquid precursor may be calculated which, when converted to a gas, will expand into a vesicle of known volume. The calculated volume will reflect an upper limit to the size of the gas filled vesicle, assuming instantaneous expansion into a gas filled vesicle and negligible diffusion of the gas over the time of the expansion.

Thus, for stabilization of the precursor in the liquid state in a mixture wherein the precursor droplet is spherical, the volume of the precursor droplet may be determined by the equation: Volume (spherical vesicle)=$\frac{4}{3}\pi r^3$, where r is the radius of the sphere.

Once the volume is predicted, and knowing the density of the liquid at the desired temperature, the amount of liquid gaseous precursor in the droplet may be determined. In more descriptive terms, the following can be applied:

$$V_{gas}=\tfrac{4}{3}\pi(r_{gas})^3$$

by the ideal gas law, $$PV=nRT$$

substituting reveals, $$V_{gas}=nRT/P_{gas}$$

or, $$n = \frac{4}{3}[\pi r_{gas}^3]P/RT \quad (A)$$

amount $n = \frac{4}{3}[\pi r_{gas}^3 P/RT] \cdot MW_n$

Converting back to a liquid volume $$V_{liq} = [\frac{4}{3}[\pi r_{gas}^3]P/RT] \cdot MW_n/D] \quad (B)$$

where D is the density of the precursor.

Solving for the diameter of the liquid droplet, $$\text{diameter}/2 = [\frac{3}{4}\pi[\frac{4}{3}\cdot[\pi r_{gas}^3]P/RT]MW_n/D]]^{1/3} \quad (C)$$

which reduces to $$\text{Diameter} = 2[[r_{gas}^3]P/RT\,[MW_n/D]]^{1/3}.$$

As a further means of preparing vesicles of the desired size for use in the methods of the present invention, and with a knowledge of the volume and especially the radius of the liquid droplets, one can use appropriately sized filters to size the gaseous precursor droplets to the appropriate diameter sphere.

A representative gaseous precursor may be used to form a vesicle of defined size, for example, 10 $\mu$m diameter. In this example, the vesicle is formed in the bloodstream of a human being, thus the typical temperature would be 37° C. or 310 K. At a pressure of 1 atmosphere and using the equation in (A), $7.54 \times 10^{-17}$ moles of gaseous precursor would be required to fill the volume of a 10 $\mu$m diameter vesicle.

Using the above calculated amount of gaseous precursor and 1-fluorobutane, which possesses a molecular weight of 76.11, a boiling point of 32.5° C. and a density of 0.7789 g/mL at 20° C., further calculations predict that $5.74 \times 10^{-15}$ grams of this precursor would be required for a 10 $\mu$m vesicle. Extrapolating further, and with the knowledge of the density, equation (B) further predicts that $8.47 \times 10^{-16}$ mL of liquid precursor is necessary to form a vesicle with an upper limit of 10 $\mu$m. Finally, using equation (C), a mixture, for example, an emulsion containing droplets with a radius of 0.0272 $\mu$m or a corresponding diameter of 0.0544 $\mu$m, is formed to make a gaseous precursor filled vesicle with an upper limit of a 10 $\mu$m vesicle.

An emulsion of this particular size could be easily achieved by the use of an appropriately sized filter. In addition, as seen by the size of the filter necessary to form gaseous precursor droplets of defined size, the size of the filter would also suffice to remove any possible bacterial contaminants and, hence, can be used as a sterile filtration as well.

This embodiment for preparing gas filled vesicles may be applied to all gaseous precursors activated by temperature. In fact, depression of the freezing point of the solvent system allows the use of gaseous precursors which would undergo liquid-to-gas phase transitions at temperatures below 0° C. The solvent system can be selected to provide a medium for suspension of the gaseous precursor. For example, 20% propylene glycol miscible in buffered saline exhibits a freezing point depression well below the freezing point of water alone. By increasing the amount of propylene glycol or adding materials such as sodium chloride, the freezing point can be depressed even further.

The selection of appropriate solvent systems may be determined by physical methods as well. When substances, solid or liquid, herein referred to as solutes, are dissolved in a solvent, such as water based buffers, the freezing point is lowered by an amount that is dependent upon the composition of the solution. Thus, as defined by Wall, one can express the freezing point depression of the solvent by the following equation:

$$\ln x_a = \ln(1-x_b) = \Delta H_{fus}/R(1/T_o - 1/T)$$

where $x_a$ is the mole fraction of the solvent; $x_b$ is the mole fraction of the solute; $\Delta H_{fus}$ is the heat of fusion of the solvent; and $T_o$ is the normal freezing point of the solvent.

The normal freezing point of the solvent can be obtained by solving the equation. If $x_b$ is small relative to $x_a$, then the above equation may be rewritten as:

$$x^b = \Delta H_{fus}/R[T-T_o/T_oT] \approx \Delta H_{fus}\Delta T/RT_o^2$$

The above equation assumes the change in temperature $\Delta T$ is small compared to $T_2$. This equation can be simplified further by expressing the concentration of the solute in terms of molality, m (moles of solute per thousand grams of solvent). Thus, the equation can be rewritten as follows.

$$X_b = m/[m + 1000/m_a] \approx mMa/1000$$

where Ma is the molecular weight of the solvent. Thus, substituting for the fraction $x_b$:

$$\Delta T = [M_a RT_o^2/1000\Delta H_{fus}]m$$

or $$\Delta T = K_f m, \text{ where } K_f = M_a RT_o^2/1000\Delta H_{fus}$$

$K_f$ is the molal freezing point and is equal to 1.86 degrees per unit of molal concentration for water at one atmosphere pressure. The above equation may be used to accurately determine the molal freezing point of solutions of gaseous-precursor filled vesicles. Accordingly, the above equation can be applied to estimate freezing point depressions and to determine the appropriate concentrations of liquid or solid solute necessary to depress the solvent freezing temperature to an appropriate value.

Methods of preparing the temperature activated gaseous precursor filled vesicles include:

(a) vortexing and/or shaking an aqueous mixture of gaseous precursor and additional materials as desired, including, for example, stabilizing materials, thickening agents and/or dispersing agents. Optional variations of this method include autoclaving before vortexing or shaking; heating an aqueous mixture of gaseous precursor; venting the vessel containing the mixture/suspension; shaking or permitting the gaseous precursor filled vesicle to form spontaneously and cooling down the suspension of gaseous precursor filled vesicles; and extruding an aqueous suspension of gaseous precursor through a filter of about 0.22 $\mu$m. Alternatively, filtering may be performed during in vivo administration of the vesicles such that a filter of about 0.22 $\mu$m is employed;

(b) microemulsification whereby an aqueous mixture of gaseous precursor is emulsified by agitation and heated to form, for example, vesicles prior to administration to a patient;

(c) heating a gaseous precursor in a mixture, with or without agitation, whereby the less dense gaseous precursor filled vesicles float to the top of the solution by expanding and displacing other vesicles in the vessel and venting the vessel to release air; and (d) utilizing in any of the above methods a sealed vessel to hold the aqueous suspension of gaseous precursor and maintaining the suspension at a temperature below the phase transition temperature of the gaseous precursor, followed by autoclaving to raise the temperature above the phase transition temperature, optionally with shaking, or permitting the gaseous precursor vesicle to form spontaneously, whereby the expanded gaseous precursor in the sealed vessel increases the pressure in the vessel, and cooling down the gas filled vesicle suspension, after which shaking may also take place.

Freeze drying is useful to remove water and organic materials prior to the shaking installation method. Drying installation methods may be used to remove water from vesicles. By pre-entrapping the gaseous precursor in the dried vesicles (i.e. prior to drying) after warming, the gaseous precursor may expand to fill the vesicle. Gaseous precursors can also be used to fill dried vesicles after they have been subjected to vacuum. As the dried vesicles are kept at a temperature below their gel state to liquid crystalline temperature, the drying chamber can be slowly filled with the gaseous precursor in its gaseous state. For example, perfluorobutane can be used to fill dried vesicles at temperatures above 4° C. (the boiling point of perfluorobutane).

Preferred methods for preparing the temperature activated gaseous precursor filled vesicles comprise shaking an aqueous solution having a lipid compound in the presence of a gaseous precursor at a temperature below the liquid state to gas state phase transition temperature of the gaseous precursor. This is preferably conducted at a temperature below the gel state to liquid crystalline state phase transition temperature of the lipid. The mixture is then heated to a temperature above the liquid state to gas state phase transition temperature of the gaseous precursor which causes the precursor to volatilize and expand. Heating is then discontinued, and the temperature of the mixture is then allowed to drop below the liquid state to gas state phase transition temperature of the gaseous precursor. Shaking of the mixture may take place during the heating step, or subsequently after the mixture is allowed to cool.

Other methods for preparing gaseous precursor filled vesicles can involve shaking an aqueous solution of, for example, a lipid and a gaseous precursor, and separating the resulting gaseous precursor filled vesicles.

Conventional, aqueous-filled liposomes of the prior art are routinely formed at a temperature above the phase transition temperature of the lipids used to make them, since they are more flexible and thus useful in biological systems in the liquid crystalline state. See, for example, Szoka and Papahadjopoulos, *Proc. Natl. Acad. Sci.* (1978) 75:4194–4198. In contrast, the vesicles made according to certain preferred embodiments described herein are gaseous precursor filled, which imparts greater flexibility, since gaseous precursors after gas formation are more compressible and compliant than an aqueous solution.

The methods contemplated by the present invention provide for shaking an aqueous solution comprising a lipid, in the presence of a temperature activatable gaseous precursor. Preferably, the shaking is of sufficient force such that a foam is formed within a short period of time, such as about 30 minutes, and preferably within about 20 minutes, and more preferably, within about 10 minutes. The shaking may involve microemulsifying, microfluidizing, swirling (such as by vortexing), side-to-side, or up and down motion. In the case of the addition of gaseous precursor in the liquid state, sonication may be used in addition to the shaking methods set forth above. Further, different types of motion may be combined. Also, the shaking may occur by shaking the container holding the aqueous lipid solution, or by shaking the aqueous solution within the container without shaking the container itself. Further, the shaking may occur manually or by machine. Mechanical shakers that may be used include, for example, the mechanical shakers described hereinbefore, with an Espe Capmix (Seefeld, Oberay Germany) being preferred. Another means for producing shaking includes the action of gaseous precursor emitted under high velocity or pressure.

According to the methods described herein, a gas, such as air, may also be provided by the local ambient atmosphere. The local ambient atmosphere can include the atmosphere within a sealed container, as well as the external environment. Alternatively, for example, a gas may be injected into or otherwise added to the container having the aqueous lipid solution or into the aqueous lipid solution itself to provide a gas other than air. Gases that are lighter than air are generally added to a sealed container, while gases heavier than air can be added to a sealed or an unsealed container. Accordingly, the present invention includes co-entrapment of air and/or other gases along with gaseous precursors.

Hence, the gaseous precursor filled vesicles can be used in substantially the same manner as the gas filled vesicles described herein, once activated by application to the tissues of a host, where such factors as temperature or pH may be used to cause generation of the gas. It is preferred that the gaseous precursors undergo phase transitions from liquid to gaseous states at or near the normal body temperature of the host, and are thereby activated, for example, by the in vivo temperature of the host so as to undergo transition to the gaseous phase therein. Alternatively, activation prior to intravenous injection may be used, for example, by thermal, mechanical or optical means. This activation can occur where, for example, the host tissue is human tissue having a normal temperature of about 37° C. and the gaseous precursors undergo phase transitions from liquid to gaseous states near 37° C.

In any of the techniques described above for the preparation of lipid-based vesicles, the steroid prodrugs and/or the targeting ligands may be incorporated with the lipids before, during or after formation of the vesicles, as would be apparent to one of ordinary skill in the art, in view of the present disclosure.

Conjugates of steroids and fluorinated surfactants or conjugates of targeting ligands and fluorinated surfactants can be synthesized by variations on a theme suggested by the reaction sequence set forth in the present disclosure and according to methods known to those skilled in the art, as disclosed, for example, by Quay, et al, European Patent Publication EP 0 727 225 A2, the disclosure of which is hereby incorporated herein by reference in its entirety. If the prodrug of choice contains a fluorinated surfactant, such as ZONYL® FSN-10o, the ZONYL® can be heated at reduced pressure to drive off volatile components, then the oily residue is reacted with a conjugation linker, the choice of which will ultimately depend on the chemistry of the functional groups on the steroid to be formulated into a prodrug. Alternatively, the steroid could be activated by methods well-known in the art. For example, targeting ligand and fluorinated surfactant conjugates can be prepared by the reaction schemes below, where "LIG" refers to a targeting ligand of the present invention and "$R_f$" refers to a fluorinated surfactant of the present invention.

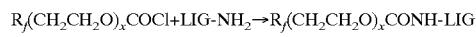

$R_f(CH_2CH_2O)_xCOCl+LIG-NH_2 \rightarrow R_f(CH_2CH_2O)_xCONH-LIG$

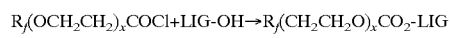

$R_f(OCH_2CH_2)_xCOCl+LIG-OH \rightarrow R_f(CH_2CH_2O)_xCO_2-LIG$

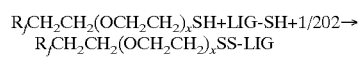

$R_fCH_2CH_2(OCH_2CH_2)_xSH+LIG-SH+1/2O_2 \rightarrow$
$R_fCH_2CH_2(OCH_2CH_2)_xSS-LIG$

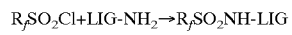

$R_fSO_2Cl+LIG-NH_2 \rightarrow R_fSO_2NH-LIG$

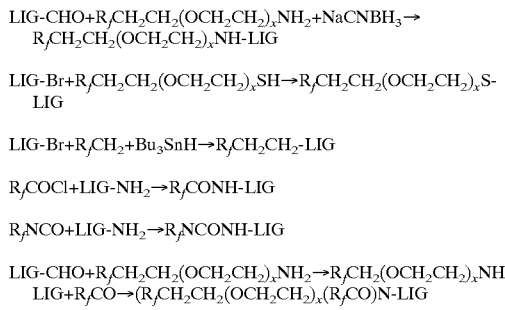

With respect to polyethylene glycol containing fragments, the following can be used, for example, PEG2-NHS ester, NHS-PEG-VS, NHS-PEG-MAL, methoxy-PEG-vinylsulfone, PEG-(VS)$_2$, methoxy-PEG-ald, PEG-(ald)$_2$, methoxy-PEG-epx, PEG-(epx)$_2$, methoxy-PEG-Tres, PEG-(Tres)$_2$, methoxy-PEG-NPC, PEG-(NPC)$_2$, methoxy-PEG-CDI, PEG-(CDI)$_2$, mPEG-Gly-OSu, mPEG-NLe-OSu, methoxy-SPA-PEG, (SPA)$_2$-PEG, methoxy-SS-PEG, (SS)$_2$-PEG all of which are available from Shearwater Polymers, Inc. (Huntsville, Ala.). Where these types of fragments are used, i.e., where the fragments may not themselves have surfactant properties adequate for a given ultrasound contrast formulation, or act only weakly as surfactants, the conjugate formed can be used in conjunction with other surfactants in the final formulation.

Vesicle compositions which comprise vesicles formulated from proteins, such as albumin vesicles, may be prepared by various processes, as will be readily apparent to those skilled in the art in view of the present disclosure. Suitable methods include those described, for example, in U.S. Pat. Nos. 4,572,203, 4,718,433, 4,774,958, and 4,957,656, the disclosures of each of which are hereby incorporated herein by reference in their entirety. Included among the methods are those which involve sonicating a solution of a protein. In preferred form, the starting material may be an aqueous solution of a heat-denaturable, water-soluble biocompatible protein. The encapsulating protein is preferably heat-sensitive so that it can be partially insolubilized by heating during sonication. Suitable heat-sensitive proteins include, for example, albumin, hemoglobin, and collagen, preferably, the protein is a human protein, with human serum albumin (HSA) being more preferred. HSA is available commercially as a sterile 5% aqueous solution, which is suitable for use in the preparation of protein-based vesicles. As would be apparent to one of ordinary skill in the art, other concentrations of albumin, as well as other proteins which are heat-denaturable, can be used to prepare the vesicles. Generally speaking, the concentration of HSA can vary and may range from about 0.1 to about 25% by weight, and all combinations and subcombinations of ranges therein. It may be preferable, in connection with certain methods for the preparation of protein-based vesicles, to utilize the protein in the form of a dilute aqueous solution. For albumin, it may be preferred to utilize an aqueous solution containing from about 0.5 to about 7.5% by weight albumin, with concentrations of less than about 5% by weight being preferred, for example, from about 0.5 to about 3% by weight.

Protein-based vesicles may be prepared using equipment which is commercially available. For example, in connection with a feed preparation operation as disclosed, for example, in U.S. Pat. No. 4,957,656, stainless steel tanks which are commercially available from Walker Stainless Equipment Co. (New Lisbon, Wis.), and process filters which are commercially available from Millipore (Bedford, Mass.), may be utilized.

The sonication operation may utilize both a heat exchanger and a flow through sonicating vessel, in series. Heat exchanger equipment of this type may be obtained from ITT Standard (Buffalo, N.Y.). The heat exchanger maintains operating temperature for the sonication process, with temperature controls ranging from about 65° C. to about 80° C., depending on the makeup of the media. The vibration frequency of the sonication equipment may vary over a wide range, for example, from about 5 to about 40 kilohertz (KHz), with a majority of the commercially available sonicators operating at about 10 or 20 KHz. Suitable sonicating equipment include, for example, a Sonics & Materials Vibra-Cell, equipped with a flat-tipped sonicator horn, commercially available from Sonics & Materials, Inc. (Danbury, Conn.). The power applied to the sonicator horn can be varied over power settings scaled from 1 to 10 by the manufacturer, as with Sonics & Materials Vibra-Cell Model VL1500. An intermediate power setting, for example, from 5 to 9, can be used. It is preferred that the vibrational frequency and the power supplied be sufficient to produce cavitation in the liquid being sonicated. Feed flow rates may range from about 50 mL/min to about 1000 mL/min, and all combinations and subcombinations of ranges therein. Residence times in the sonication vessel can range from about 1 second to about 4 minutes, and gaseous fluid addition rates may range from about 10 cubic centimeters (cc) per minute to about 100 cc/min, or 5% to 25% of the feed flow rate, and all combinations and subcombinations of ranges therein.

It may be preferable to carry out the sonication in such a manner to produce foaming, and especially intense foaming, of the solution. Generally speaking, intense foaming and aerosolating are important for obtaining a contrast agent having enhanced concentration and stability. To promote foaming, the power input to the sonicator horn may be increased, and the process may be operated under mild pressure, for example, about 1 to about 5 psi. Foaming may be easily detected by the cloudy appearance of the solution, and by the foam produced.

Suitable methods for the preparation of protein-based vesicles may also involve physically or chemically altering the protein or protein derivative in aqueous solution to denature or fix the material. For example, protein-based vesicles may be prepared from a 5% aqueous solution of HSA by heating after formation or during formation of the contrast agent via sonication. Chemical alteration may involve chemically denaturing or fixing by binding the protein with a difunctional aldehyde, such as gluteraldehyde. For example, the vesicles may be reacted with 0.25 grams of 50% aqueous gluteraldehyde per gram of protein at pH 4.5 for 6 hours. The unreacted gluteraldehyde may then be washed away from the protein.

In any of the techniques described above for the preparation of protein-based stabilizing materials and/or vesicles, the steroid prodrugs and/or targeting ligands may be incorporated with the proteins before, during or after formation of the vesicles, as would be apparent to one of ordinary skill in the art, based on the present disclosure. Vesicle compositions which comprise vesicles formulated from polymers may be prepared by various processes, as will be readily apparent to those skilled in the art in view of the present disclosure. Exemplary processes include, for example, interfacial polymerization, phase separation and coacervation, multiorifice centrifugal preparation, and solvent evaporation. Suitable procedures which may be employed or modified in accordance with the present disclosure to prepare vesicles from polymers include those procedures disclosed in U.S. Pat. Nos. 4,179,546, 3,945,956, 4,108,806, 3,293, 114, 3,401,475, 3,479,811, 3,488,714, 3,615,972, 4,549,892, 4,540,629, 4,421,562, 4,420,442, 4,898,734, 4,822,534, 3,732,172, 3,594,326, and 3,015,128; Japan Kokai Tokkyo Koho 62 286534, British Patent No. 1,044,680, Deasy, *Microencapsulation and Related Drug Processes*, Vol. 20, Chs. 9 and 10, pp. 195–240 (Marcel Dekker, Inc., N.Y., 1984), Chang et al., *Canadian J. of Physiology and Pharmacology*, 44:115–129 (1966), and Chang, *Science*, 146:524–525 (1964), the disclosures of each of which are hereby incorporated herein by reference in their entirety.

In accordance with a preferred synthesis protocol, the vesicles may be prepared using a heat expansion process, such as, for example, the process described in U.S. Pat. Nos. 4,179,546, 3,945,956, and 4,108,806, British Patent No. 1,044,680, and Japan Kokai Tokkyo Koho 62 286534. In general terms, the heat expansion process may be carried out by preparing vesicles of an expandable polymer or copolymer which may contain in their void (cavity) a volatile liquid (gaseous precursor). The vesicle is then heated, plasticising the vesicle and converting the volatile liquid into a gas, causing the vesicle to expand to up to about several times its original size. When the heat is removed, the thermoplastic polymer retains at least some of its expanded shape. Vesicles produced by this process tend to be of particularly low density, and are thus preferred. The foregoing described process is well known in the art, and may be referred to as the heat expansion process for preparing low density vesicles.

Polymers useful in the heat expansion process will be readily apparent to those skilled in the art and include thermoplastic polymers or copolymers, including polymers or copolymers of many of the monomers described above. Preferable of the polymers and copolymers described above include the following copolymers: polyvinylidene-polyacrylo-nitrile, polyvinylidene-polyacrylonitrile-polymethylmethacrylate, and polystyrene-polyacrylonitrile. A most preferred copolymer is polyvinylidene-polyacrylonitrile.

Volatile liquids useful in the heat expansion process will also be well known to those skilled in the art and include: aliphatic hydrocarbons such as ethane, ethylene, propane, propene, butane, isobutane, neopentane, acetylene, hexane, heptane; chlorofluorocarbons such as $CCl_3F$, $CCl_2F_3$, $CClF_3$, $CClF_2$-$CCl_2F_2$, chloroheptafluoro-cyclobutane, and 1,2-dichlorohexafluorocyclobutane; tetraalkyl silanes, such as tetramethyl silane, trimethylethyl silane, trimethylisopropyl silane, and trimethyl n-propyl silane; as well as perfluorocarbons, including the perfluorocarbons described above. In general, it is important that the volatile liquid not be a solvent for the polymer or copolymer being utilized. It is also preferred that the volatile liquid have a boiling point that is below the softening point of the involved polymer or copolymer. Boiling points of various volatile liquids and softening points of various polymers and copolymers will be readily ascertainable to one skilled in the art, and suitable combinations of polymers or copolymers and volatile liquids will be easily apparent to the skilled artisan. By way of guidance, and as one skilled in the art would recognize, generally as the length of the carbon chain of the volatile liquid increases, the boiling point of that liquid increases also. Also, mildly preheating the vesicles in water in the presence of hydrogen peroxide prior to definitive heating and expansion may pre-soften the vesicle to allow expansion to occur more readily.

For example, to produce vesicles from synthetic polymers, vinylidene and acrylonitrile may be copolymerized in a medium of isobutane liquid using one or more of the foregoing modified or unmodified literature procedures, such that isobutane becomes entrapped within the vesicles. When such vesicles are then heated to a temperature of from about 80° C. to about 120° C., the isobutane gas expands, which in turn expands the vesicles. After heat is removed, the expanded polyvinylidene and acrylonitrile copolymer vesicles remain substantially fixed in their expanded position. The resulting low density vesicles are extremely stable both dry and suspended in an aqueous media. Isobutane is utilized herein merely as an illustrative liquid, with the understanding that other liquids which undergo liquid/gas transitions at temperatures useful for the synthesis of these vesicles and formation of the very low density vesicles upon heating can be substituted for isobutane. Similarly, monomers other than vinylidene and acrylonitrile may be employed in preparing the vesicles.

In certain preferred embodiments, the vesicles which are formulated from synthetic polymers and which may be employed in the methods of the present invention are commercially available from Expancel, Nobel Industries (Sundsvall, Sweden), including EXPANCEL 551 DE™ microspheres. The EXPANCEL 551 DE™ microspheres are composed of a copolymer of vinylidene and acrylonitrile which have encapsulated therein isobutane liquid. Such microspheres are sold as a dry composition and are approximately 50 microns in size. The EXPANCEL 551 DE™ microspheres have a specific gravity of only 0.02 to 0.05, which is between one-fiftieth and one-twentieth the density of water.

In any of the techniques described above for the preparation of polymer-based stabilizing materials and/or vesicles, the steroid prodrugs and/or targeting ligands may be incorporated with the polymers before, during or after formation of the vesicles, as would be apparent to one of ordinary skill in the art, based on the present disclosure.

As with the preparation of stabilizing materials and/or vesicles, a wide variety of techniques are available for the preparation of stabilizing materials comprising bioactive agents (which includes steroid prodrugs and targeting ligands). For example, the stabilizing materials and/or vesicle compositions may be prepared from a mixture of lipid compounds, bioactive agents and gases and/or gaseous precursors. In this case, lipid compositions are prepared as described above in which the compositions also comprise bioactive agents. Thus, for example, micelles can be prepared in the presence of a bioactive agent. In connection with lipid compositions which comprise a gas, the preparation can involve, for example, bubbling a gas directly into a mixture of the lipid compounds and one or more additional materials. Alternatively, the lipid compositions may be preformed from lipid compounds and gas and/or gaseous precursor. In the latter case, the bioactive agent is then added to the lipid composition prior to use. For example, an aqueous mixture of liposomes and gas may be prepared to which the bioactive agent is added and which is agitated to provide the liposome composition. The liposome composition can be readily isolated since the gas and/or bioactive agent filled liposome vesicles generally float to the top of the aqueous solution. Excess bioactive agent can be recovered from the remaining aqueous solution.

As those skilled in the art will recognize, any of the stabilizing materials and/or vesicle compositions may be lyophilized for storage, and reconstituted or rehydrated, for example, with an aqueous medium (such as sterile water, phosphate buffered solution, or aqueous saline solution), with the aid of vigorous agitation. Lyophilized preparations generally have the advantage of greater shelf life. To prevent agglutination or fusion of the lipids and/or vesicles as a result of lyophilization, it may be useful to include additives which prevent such fusion or agglutination from occurring. Additives which may be useful include sorbitol, mannitol, sodium chloride, glucose, dextrose, trehalose, polyvinylpyrrolidone and poly(ethylene glycol) (PEG), for example, PEG 400. These and other additives are described in the literature, such as in the U.S. Pharmacopeia, USP XXII, NF XVII, The United States Pharmacopeia, The National Formulary, United States Pharmacopeial Convention Inc., 12601 Twinbrook Parkway, Rockville, Md. 20852, the disclosure of which is hereby incorporated herein by reference in its entirety.

The concentration of lipid required to form a desired stabilized vesicle level will vary depending upon the type of lipid used, and may be readily determined by routine experimentation. For example, in preferred embodiments, the concentration of 1,2-dipalmitoylphosphatidylcholine (DPPC) used to form stabilized vesicles according to the methods of the present invention is about 0.1 mg/ml to about 30 mg/ml of saline solution, more preferably from about 0.5 mg/ml to about 20 mg/ml of saline solution, and most preferably from about 1 mg/ml to about 10 mg/ml of saline solution. The concentration of distearoylphosphatidylcholine (DSPC) used in preferred embodiments is about 0.1 mg/ml to about 30 mg/ml of saline solution, more preferably from about 0.5 mg/ml to about 20 mg/ml of saline solution, and most preferably from about 1 mg/ml to about 10 mg/ml of saline solution. The anount of composition which is administered to a patient can vary.

Typically, the intravenous dose may be less than about 10 mL for a 70 Kg patient, with lower doses being preferred.

Another embodiment of preparing a targeted therapeutic steroid prodrug composition comprises combining at least one biocompatible lipid and a gaseous precursor; agitating until gas filled vesicles are formed; adding a steroid prodrug and/or targeting ligand to said gas filled vesicles such that the steroid prodrug and/or targeting ligand binds to said gas filled vesicle by a covalent bond or non-covalent bond; and agitating until a delivery vehicle comprising gas filled vesicles and a steroid prodrug and/or targeting ligand result. Rather than agitating until gas filled vesicles are formed before adding the steroid prodrug and/or targeting ligand, the gaseous precursor may remain a gaseous precursor until the time of use. That is, the gaseous precursor is used to prepare the delivery vehicle and the precursor is activated in vivo, by temperature for example.

Alternatively, a method of preparing targeted therapeutic steroid prodrug compositions may comprise combining at least one biocompatible lipid and a steroid prodrug and/or targeting ligand such that the steroid prodrug and/or targeting ligand binds to said lipid by a covalent bond or non-covalent bond, adding a gaseous precursor and agitating until a delivery vehicle comprising gas-filled vesicles and a steroid prodrug and/or targeting ligand result. In addition, the gaseous precursor may be added and remain a gaseous precursor until the time of use. That is, the gaseous precursor is used to prepare the delivery vehicle having gaseous precursor filled vesicles and a steroid prodrug and/or targeting ligand which result for use in vivo.

Alternatively, the gaseous precursors may be utilized to create stable gas filled vesicles with steroid prodrugs and/or targeting ligands which are pre-formed prior to use. In this embodiment, the gaseous precursor and steroid prodrug and/or targeting ligand are added to a container housing a suspending and/or stabilizing medium at a temperature below the liquid-gaseous phase transition temperature of the respective gaseous precursor. As the temperature is then exceeded, and an emulsion is formed between the gaseous precursor and liquid solution, the gaseous precursor undergoes transition from the liquid to the gaseous state. As a result of this heating and gas formation, the gas displaces the air in the head space above the liquid suspension so as to form gas filled lipid spheres which entrap the gas of the gaseous precursor, ambient gas for example, air, or coentrap gas state gaseous precursor and ambient air. This phase transition can be used for optimal mixing and stabilization of the delivery vehicle. For example, the gaseous precursor, perfluorobutane, can be entrapped in the biocompatible lipid or other stabilizing compound, and as the temperature is raised, beyond 4° C. (boiling point of perfluorobutane) stabilizing compound entrapped fluorobutane gas results. As an additional example, the gaseous precursor fluorobutane, can be suspended in an aqueous suspension containing emulsifying and stabilizing agents such as glycerol or propylene glycol and vortexed on a commercial vortexer. Vortexing is commenced at a temperature low enough that the gaseous precursor is liquid and is continued as the temperature of the sample is raised past the phase transition temperature from the liquid to gaseous state. In so doing, the precursor converts to the gaseous state during the microemulsification process. In the presence of the appropriate stabilizing agents, surprisingly stable gas filled vesicles and steroid prodrugs and/or targeting ligand result.

Accordingly, the gaseous precursors may be selected to form a gas filled vesicle in vivo or may be designed to produce the gas filled vesicle in situ, during the manufacturing process, on storage, or at some time prior to use.

According to the methods contemplated by the present invention, the presence of gas, such as and not limited to air, may also be provided by the local ambient atmosphere. The local ambient atmosphere may be the atmosphere within a sealed container, or in an unsealed container, may be the external environment. Alternatively, for example, a gas may be injected into or otherwise added to the container having the aqueous lipid solution or into the aqueous lipid solution itself in order to provide a gas other than air. Gases that are not heavier than air may be added to a sealed container while gases heavier than air may be added to a sealed or an unsealed container. Accordingly, the present invention includes co-entrapment of air and/or other gases along with gaseous precursors.

Hence, the stabilized vesicle precursors described above, can be used in the same manner as the other stabilized vesicles used in the present invention, once activated by application to the tissues of a host, where such factors as temperature or pH may be used to cause generation of the gas. It is preferred that this embodiment is one wherein the gaseous precursors undergo phase transitions from liquid to gaseous states at or near the normal body temperature of said host, and are thereby activated by the temperature of said host tissues so as to undergo transition to the gaseous phase therein. More preferably still, this method is one wherein the host tissue is human tissue having a normal temperature of about 37° C., and wherein the gaseous precursors undergo phase transitions from liquid to gaseous states near 37° C.

All of the above embodiments involving preparations of the stabilized gas filled vesicles used in the present invention, may be sterilized by autoclave or sterile filtration if these processes are performed before either the gas instillation step or prior to temperature mediated gas conversion of the temperature sensitive gaseous precursors within the suspension. Alternatively, one or more antibactericidal agents and/or preservatives may be included in the formulation of the compositions including, for example, sodium benzoate, all quaternary ammonium salts, sodium azide, methyl paraben, propyl paraben, sorbic acid, ascorbylpalmitate, butylated hydroxyanisole, butylated hydroxytoluene, chlorobutanol, dehydroacetic acid, ethylenediamine, monothioglycerol, potassium benzoate, potassium metabisulfite, potassium sorbate, sodium bisulfite, sulfur dioxide, and organic mercurial salts. Such sterilization, which may also be achieved by other conventional means, such as by irradiation, will be necessary where the stabilized microspheres are used for imaging under invasive circumstances, for example, intravascularly or intraperitoneally. The appropriate means of sterilization will be apparent to the artisan instructed by the present description of the stabilized gas filled vesicles and their use. The compositions are generally stored as an aqueous suspension but in the case of dried or lyophilized vesicles or dried or lyophilized lipidic spheres the con4. Positions may be stored as a dried or lyophilized powder ready to be reconstituted or rehydrated prior to use.

Applications

Novel targeted therapeutic delivery systems of the present invention are useful as contrast media in diagnostic imaging, and for use in all areas where diagnostic imaging is employed. Diagnostic imaging is a means to visualize internal body regions of a patient, and includes, for example, ultrasound (US), magnetic resonance imaging (MRI), nuclear magnetic resonance (NMR), computed tomography (CT), electron spin resonance (ESR); nuclear medicine when the contrast medium includes radioactive material; and optical imaging, particularly with a fluorescent contrast medium. Diagnostic imaging also includes promoting the rupture of vesicles via the methods of the present invention. For example, ultrasound may be used to visualize the vesicles and verify the localization of the vesicles in certain tissue. In addition, ultrasound nay. be used to promote rupture of the vesicles once the vesicles reach the intended target, including tissue and/or receptor destinations, thus releasing a bioactive agent, such as a steroid prodrug.

In accordance with the present invention, there are provided methods of imaging a patient generally, diagnosing the presence of diseased tissue in a patient and/or delivering a bioactive agent to a patient. The imaging process of the present invention may be carried out by administering a composition of the invention to a patient, and then scanning the patient using, for example, ultrasound, computed tomography, and/or magnetic resonance imaging, to obtain visible images of an internal region of a patient and/or of any diseased tissue in that region. The contrast medium may be particularly useful in providing images of tissue, such as eye, myocardial, endothelial, and/or epithelial tissue, as well as the gastrointestinal and cardiovascular regions, but can also be employed more broadly, such as in imaging the vasculature, or in other ways as will be readily apparent to those skilled in the art. Cardiovascular region denotes the region of the patient defined by the heart and the vasculature leading directly to and from the heart. The phrase vasculature denotes the blood vessels (arteries, veins, etc.) in the body or in an organ or part of the body. The patient can be any type of mammal, but most preferably is a human.

The present invention also provides a method of diagnosing the presence of diseased tissue. Diseased tissue includes, for example, cancerous tissue, and endothelial tissue which results from vasculature that supports diseased tissue. As a result, the localization and visualization of endothelial tissue to a region of a patient which under normal circumstances is not associated with endothelial tissue provides an indication of diseased tissue in the region. The present methods can also be used in connection with delivery of a bioactive agent, such as a steroid prodrug, to an internal region of a patient.

Treatment of prostate cancer and benign prostatic hypertrophy may be treated with a targeted therapeutic delivery system of the present invention. Therapeutics for the treatment of prostate cancer and benign prostatic hypertrophy include testosterone, methyltestosterone, fluoxymesterone, finasteride (proscar), and inhibitors of the steroid 5a reductase enzyme. Typically, the therapeutic is administered intravenously or transurethrally. Ultrasound may be focused on the prostate gland, either transperitoneally, transurethrally, transabdominally, or via a endorectal ultrasound probe.

Ultrasound may be applied to a body region such as the eye for treatment of ophthalmic disease or to the prostate for the treatment of prostatic disease after, before or during administration of the acoustically active carrier. Generally the compositions of the present invention are administered intravenously, although in some cases intraocular administration may also be performed. The preferred route of administration is by intravenous administration. Most preferably the targeted therapeutic delivery systems are administered during sonication and sonication is continued for some time, e.g. between a minute to several hours after administration of the acoustically active carriers. Most preferably ultrasound diagnostic imaging is performed in concert with therapeutic sonication to provide vesicle rupture and ultrasound treatment. Additionally laser or optical imaging may be performed to monitor vesicle rupture and retinal therapy. An optical sensor such as fluorescein dye may be coadministered or incorporated into the acoustically active carriers to monitor therapy and visualize retinal blood flow.

Ultrasound applied to the eye may vary in frequency between about 20 KHz and 100 MHz but is more preferably between 100 KHz and 25 MHz. Still more preferably the ultrasound frequency varies between about 500 KHz and about 20 MHz. The sonication therapy frequency and imaging frequencies may be the same or may be swept. PRICH (decreasing) or CHIRP (increasing frequencies) may be employed. Imaging and therapeutic frequencies and imaging and therapeutic energies may each be the same or different. Most preferably a 1x frequency pulse or series of pulses (train of continuous wave pulses) is applied to the eye and then a 2x, 3x or 5x (the 2x pulse is most preferred) is then applied to the eye after the first burst of 1x pulses. Superimposition of first and second frequencies results enhancing bubble rupture and local drug delivery. In general the energy used varies from between 1 millliwatts to 10 Watts for bubble rupture and for continuous wave between 5% by 100% duty cycle. Except for retinal or ocular tumor ablation the energy is usually kept below the thresh-hold for lethal cytotoxicity. When retinal neovascular ablation is desired (e.g. in treatment of retinal neovascularity associated with macular degeneration) the preferred means of effect is either via apoptosis or thrombosis of the vascular lesions. In general the therapeutic pulse of ultrasound energy is less than 5 Watts and usually under 1 Watt. Most preferably the level of energy is between about 20 milliwatts to about 1 Watt. As one skilled in the art would recognize, however, the level of peak energy which is selected will vary depending upon the specific application, the duty cycle, pulse repetition rate, frequency and other factors. In general the requisite amount of therapeutic ultrasound energy may vary approximately by the reciprocal of the square root of the frequency.

Usually the ultrasound probe is placed directly on the eye, usually on the anterior cornea. Preferably an acoustic couplant material is placed onto the surface of the eye before application of the ultrasonic probe. An anesthetic agent, e.g. viscous lidocaine (1%), may be placed on the eye first or the anesthetic agent may be incorporated into the acoustic couplant, e.g. silicone gel. The transducer is then applied to the surface of the eye. Ultrasound imaging is performed to visualize the retina and ocular structures. Generally therapy is performed after a prior light ophthalmoscopic examination and this information is used for planning therapy with ultrasound and acoustically active carriers. In some cases however, ultrasound alone may be sufficient for planning therapy.

To avoid damage to the lens, the ultrasound transducer can be positioned peripherally on the eye so that the ultrasound beam does not necessarily have to pass through the lens. In this fashion the ultrasound beam can still be focused or directed on posterior structures such as the retina. For treatment of glaucoma the ultrasound beam can be focused on the ciliary body.

As one skilled in the art would recognize, higher frequencies provide higher spatial resolution for imaging and also higher spatial localization for therapy. For example the wave length of 1 MHz ultrasound=0.155 cm and the wavelength of 10 MHz ultrasound=0.016 cm. By careful spatial positioning of the ultrasound transducer on the eye, immobilization of the patient by means of a head hold and mechanical or electronic sweeping of the ultrasound beam and focal spot the therapeutic sound may be focused to small regions on the eye and retina. The head may be immobilized in a device for localized application of ultrasound to the retina. In principal this invention affords treatment of lesions as small as the wavelength of the ultrasound involved, e.g. 1 mm at 1 MHz and 100 microns at 10 MHz. Note that the higher frequency will allow much higher accuracy for treating smaller lesions but may also require higher energy, e.g. about 3.3 times more than for at 1 MHz. Also, smaller bubbles, e.g. below 1 micron, will generally be more effective drug carriers for treatment at 10 MHz. Larger bubbles, e.g. 1 to 5 microns will be more effective at the lower frequencies such as 1 MHz.

In a preferred embodiment of this invention there is involved a superimposition of fundamental and harmonic frequencies to maximize the effectiveness of bubble rupture. For example, a burst of continuous wave 5 MHz ultrasound may be followed by a second burst of 10 MHz continuous wave ultrasound focused upon the tissue to be treated.

By selecting the targeted therapeutic delivery systems with sufficient plasma half-lives and continuing application of ultrasound to the desired treatment region in the retina or other target tissue, appreciable drug delivery can be attained within the target treatment volume.

The compositions of the invention, including the steroid prodrugs, may be administered to the patient by a variety of different means. The means of administration will vary depending upon the intended application. As one skilled in the art would recognize, administration of the steroid prodrug or the steroid prodrug in combination with the stabilizing materials and/or vesicles of the present invention can be carried out in various fashions, for example, topically, including ophthalmic, dermal, ocular and rectal, intrarectally, transdermally, orally, intraperitoneally, parenterally, intravenously, intralymphatically, intratumorly, intramuscularly, interstitially, intraarterially, subcutaneously, intraocularly, intrasynovially, transepithelially, pulmonarily via inhalation, ophthalmically, sublingually, buccally, or via nasal inhalation via insufflation, nebulization, such as by delivery of an aerosol. Preferably, the steroid prodrugs and/or stabilizing materials of the present invention are administered intravenously or topically/transdermally. In the case of inhalation, a gaseous precursor delivered with a composition of the present invention such that the gaseous precursor is in liquid, gas, or liquid and gas form.

Vesicles containing one or more of the bioactive materials set forth herein, may be activated by ultrasound for localized drug delivery. The therapeutic delivery systems of the invention, however, are also competent drug delivery vehicles without the administration of ultrasound. For example, therapeutic delivery systems comprising targeting ligands may fuse to cells.

Figure 7:
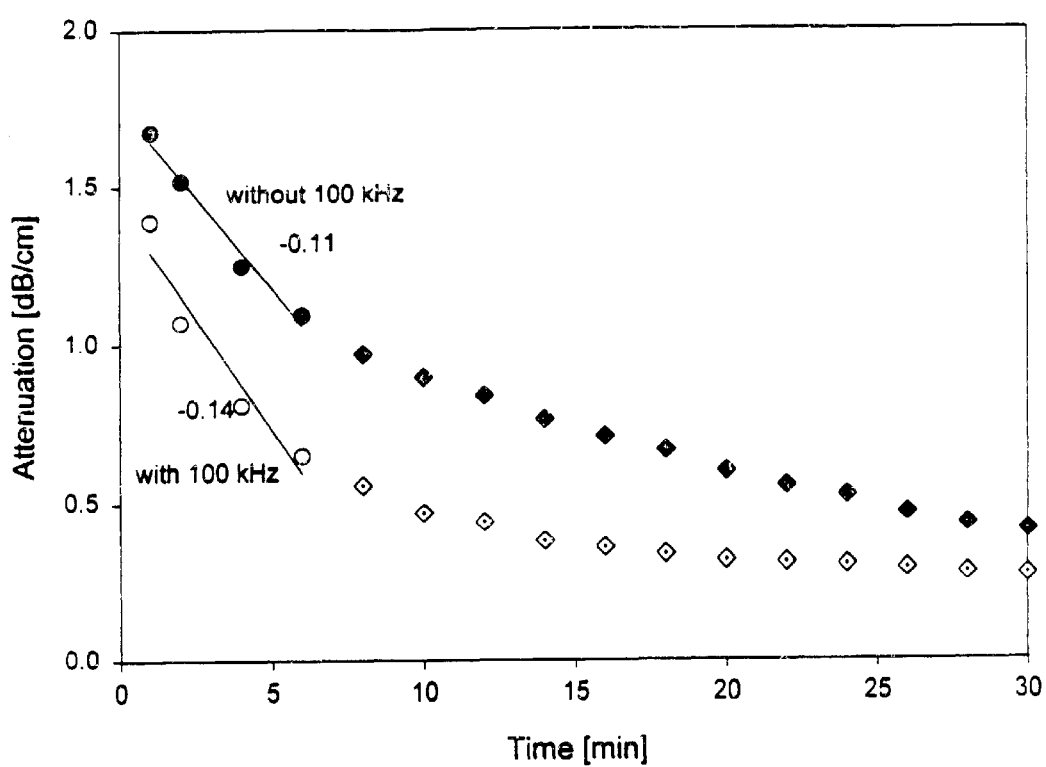
FIG. 7 shows the time course of attenuation of various formulations of a therapeutic delivery systems with an without the application of 100 kHz ultrasound for a soybean oil/1 mg/ml DPPC mixture.
Figure 8:
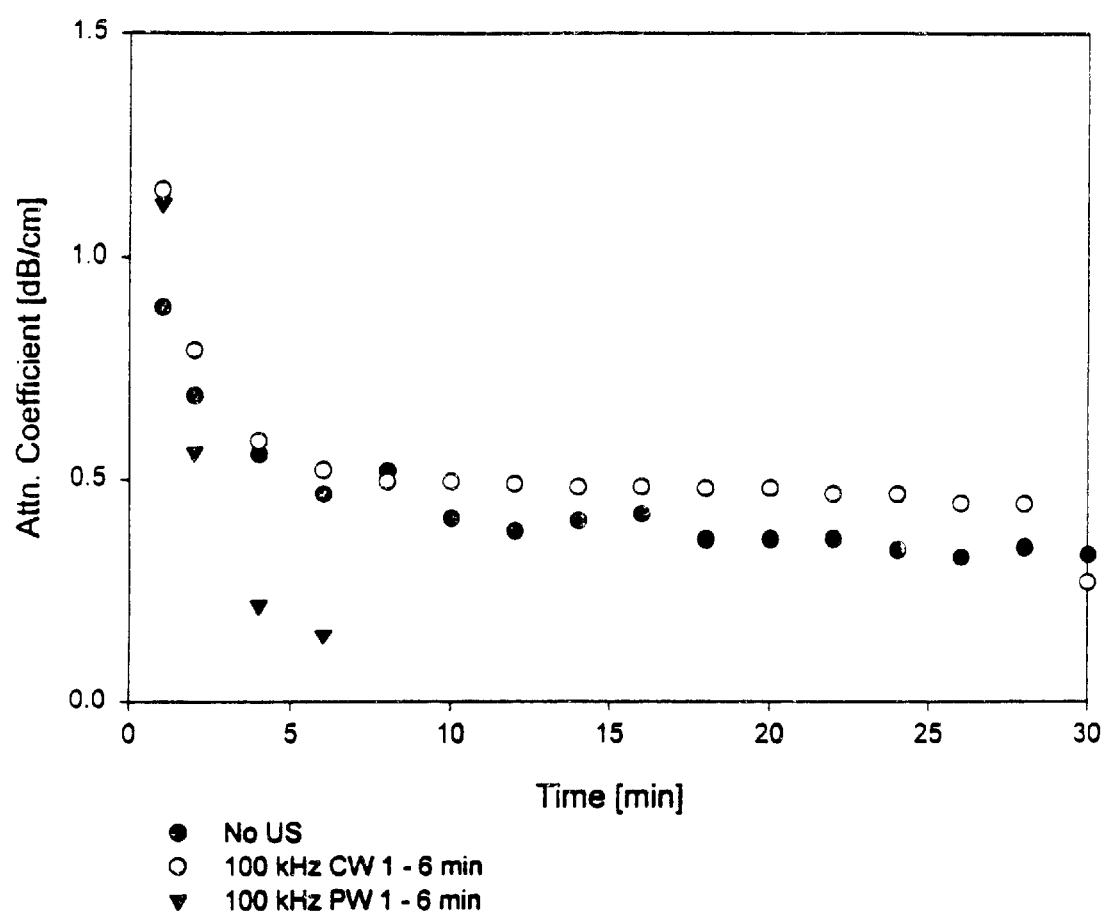
FIG. 8 shows the time course of attenuation of various formulations of a therapeutic delivery systems with an without the application of 100 kHz ultrasound for canola oil/1 mg/ml DSPC mixture.
Figure 9:
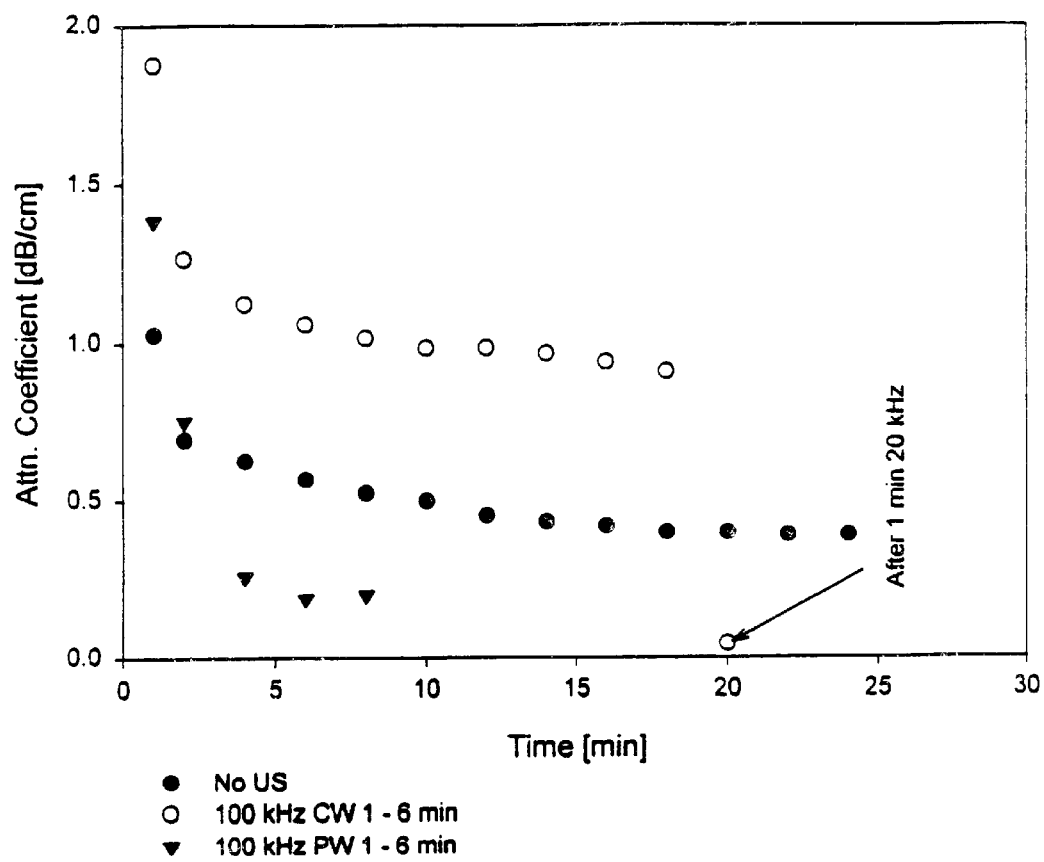
FIG. 9 shows the time course of attenuation of various formulations of a therapeutic delivery systems with an without the application of 100 kHz ultrasound for a canola oil/5 mg/ml DSPC mixture.

FIG. 7 shows the acoustic response of acoustically active liposheres. Application of higher energy ultrasound, preferably with a low frequency of around 100 kHz, as in Example 9, results in a loss of acoustiG activity and release of the entrapped drug. Ultrasound is believed to transfer thermal and mechanical energy in the form of acoustic vibrations and oscillations.

Ultrasound mediated targeting and drug release and activation using the steroid prodrugs of the present invention is advantageous for treating a variety of different diseases and medical conditions, such as autoimmune diseases, organ transplants, arthritis, and myasthenia gravis. Following the systemic administration of the steroid prodrug delivery vehicles to a patient, ultrasound may then be applied to the affected tissue. For arthritis, including synovial-based inflammation arthritis, such as rheumatoid arthritis, ultrasound may be applied to the joints affected by the disease. For myasthenia gravis, ultrasound may be applied to the thymus. For transplant rejection, ultrasound may be applied to the organ transplant, such as in a kidney transplant.

For topical applications, the steroid prodrugs may be used alone, may be mixed with one or more solubilizing agents or may be used with a delivery vehicle, and applied to the skin or mucosal membranes. Other penetrating and/or solubilizing agents useful for the topical application of the steroid prodrug include, for example, pyrrolidones such as 2-pyrrolidone, N-methyl-2-pyrrolidone, 1-methyl-2-pyrrolidone, 5-methyl-2-pyrrolidone, 1-ethyl-2-pyrrolidone, 2-pyrrolidone-5-carboxylic acid, N-hydroxyethylpyrrolidone, N-cyclohexylpyrrolidone, N-dimethylaminopropylpyrrolidone, N-cocalyklpyrrolidone, N-tallowalkylpyrrolidone, 1-lauryl-2-pyrrolidone, and 1-hyxyl-2-pyrrolidone; fatty acids such as oleic acid, linoleic acid, heptanoic acid, caproic acid, lauric acid, stearic acid, octadecenoic acid, palritoleic acid, myristic acid and palmitelaidic acid; sulfoxides such as dimethylsulfoxide, dimethylacetamide, dimethylformamide, N-methylformamide and decylmethylsulfoxide; amines and derivatives such as-N,N-diethyl-m-toluamide, dodecylamine, ethoxylated amine, N,N-bis(2-hydroxyethyl)oleylamine, dodecyl-N,N-dimethylamino acetate, sodium pryoglutaminate and N-hydroxylethalacetamide; terpenes and terpenoids such as a-pinenes, d-limonene, 3-carene, a-terpineol, terpinen-4-ol, careol, abisabolol, carvone, pulegone, piperitone, menthone, fenchone, cyclohexene oxide, limonene oxide, pinene oxide, cyclopentene oxide, ascaridol, 7-oxabicyclo(2.2.1)heptane, 1,8-cineole, safrole, 1-carvone, terpenoid cyclohexanone derivatives, acyclic terpenehydrocarbon chains, hydrocarbon terpenes, cyclic ether terpenes, cardamon seed extract, monoterpene terpineol and acetyl terpineol; essential oils of eucalyptus, chenopodium and yang ylang; surfactants such as anionic-sodiumlaurylsulfate, phenylsulfurate CA, calciumdodecylbenzene sulfonate, empicol ML26/F and magnesiumlaurylsulfate; cationic-cetyltrimethyl-ammonium bromide; nonionic-synperonic NP series and PE series and the polysorbates; zwiterionic-N-dodecyl-N,N-dimethylbetaine; alcohols such as ethanol, lauryl alcohol, linolenyl alcohol, 1-octanol, 1-propanol and 1-butanol; urea, cyclic unsaturated urea analogs, glycols, azone, n-alkanols, n-alkanes, orgelase, alphaderm cream and water. The penetrating/ solubilizing agents may or may not be in a base which can be composed of various substances known to those skilled in the art, including, for example, glycerol, propylene glycol; isopropyl myristate; urea in propylene glycol, ethanol and water; and polyethylene glycol (PEG).

The steroid prodrugs formulated with penetration enhancing agents, known to those skilled in the art and described above, may be administered transdermally in a patch or reservoir with a permeable membrane applied to the skin. The use of rupturing ultrasound may increase transdermal delivery of therapeutic compounds, including the steroid prodrugs of the present invention. Further, an imaging mechanism may be used to monitor and modulate delivery of the steroid prodrugs. For example, diagnostic ultrasound may be used to visually monitor the bursting of the gas filled vesicles and modulate drug delivery and/or a hydrophone may be used to detect the sound of the bursting of the gas filled vesicles and modulate drug delivery.

The delivery of bioactive agents in accordance with the present invention using ultrasound is best accomplished for tissues which have a good acoustic window for the transmission of ultrasonic energy. This is the case for most tissues in the body such as muscle, the heart, the liver and most other vital structures. In the brain, in order to direct the ultrasonic energy past the skull a surgical window may be necessary.

The gas filled vesicles of the invention are especially useful for bioactive agents that may be degraded in aqueous media or upon exposure to oxygen and/or atmospheric air. For example, the vesicles may be filled with an inert gas such as nitrogen or argon, for use with labile bioactive agents. Additionally, the gas filled vesicles may be filled with an inert gas and used to encapsulate a labile bioactive agents for use in a region of a patient that would normally cause the therapeutic to be exposed to atmospheric air, such as cutaneous and ophthalmic applications.

The invention is useful in delivering bioactive agents to a patient's lungs. For pulmonary applications of the steroid prodrugs, dried or lyophilized powdered liposomes may be administered via inhaler. Aqueous suspensions of liposomes or micelles, preferably gas/gaseous precursor filled, may be administered via nebulization. Gas filled liposomes of the present invention are lighter than, for example, conventional liquid filled liposomes which generally deposit in the central proximal airway rather than reaching the periphery of the lungs. It is therefore believed that the gas filled liposomes of the present invention may improve delivery of a bioactive agent to the periphery of the lungs, including the terminal airways and the alveoli. For application to the lungs, the gas filled liposomes may be applied through nebulization.

In applications such as the targeting of the lungs, which are lined with lipids, the bioactive agent may be released upon aggregation of the gas filled liposomes with the lipids lining the targeted tissue. Additionally, the gas filled liposomes may burst after administration without the use of ultrasound. Thus, ultrasound need not be applied to release the drug in the above type of administration. For vascular administration the steroid prodrugs are generally injected into the venous system as a formulation vehicle, e.g. preferably gas or gaseous precursor containing liposomes.

It is a further embodiment of this invention in which ultrasound activation affords site specific delivery of the steroid prodrugs. Generally, the gas and/or gaseous precursor containing vehicles are echogenic and visible on ultrasound. Ultrasound can be used to image the target tissue and to monitor the drug carrying vehicles as they pass through the treatment region. As increasing levels of ultrasound are applied to the treatment region, this breaks apart the delivery vehicles and/or releases the drug within the treatment region. "Release of the drug" or "release of the steroid" includes: (1) the release of the steroid prodrug from the delivery vehicle but not from the linking group and lipid moiety; (2) the release of the steroid from the covalently bonded lipid moiety and/or the linking group, but not from the delivery vehicle; and (3) the release of the steroid from both the delivery vehicle and from the covalently bonded lipid moiety and/or the linking group. Preferably, "release of the drug/steroid" is (1) the release of the steroid from the delivery vehicle but not from the linking group and lipid moiety or (3) the release of the steroid from both the delivery vehicle and from the covalently bonded lipid moiety and linking group.

Drug release and/or vesicle rupture can be monitored ultrasonically by several different mechanisms. Bubble or vesicle destruction results in the eventual dissolution of the ultrasound signal. However, prior to signal dissolution, the delivery vehicles/vesicles provide an initial burst of signal. In other words, as increasing levels of ultrasound energy are applied to the treatment zone containing the delivery vehicles/vesicles, there is a transient increase in signal. This transient increase in signal may be recorded at the fundamental frequency, the harmonic, odd harmonic or ultraharmonic frequency.

The useful dosage to be administered and the particular mode of administration will vary depending upon the age, weight and the particular mammal and region thereof to be scanned, and the particular contrast agent employed. Typically, dosage is initiated at lower levels and increased until the desired contrast enhancement is achieved. Various combinations of the lipid compositions may be used to alter properties as desired, including viscosity, osmolarity or palatability.

Generally, the steroid prodrugs, stabilizing materials and/or vesicles of the invention are administered in the form of an aqueous suspension such as in water or a saline solution (e.g., phosphate buffered saline). Preferably, the water is sterile. Also, preferably the saline solution is an isotonic saline solution, although, if desired, the saline solution may be hypotonic (e.g., about 0.3 to about 0.5% NaCl). The solution may be buffered, if desired, to provide a pH range of about 5 to about 7.4. Preferably, dextrose or glucose is included in the media. Other solutions that may be used for administration of gas filled liposomes include, for example, almond oil, corn oil, cottonseed oil, ethyl oleate, isopropyl myristate, isopropyl palmitate, mineral oil, myristyl alcohol, octyldodecanol, olive oil, peanut oil, persic oil, sesame oil, soybean oil, and squalene.

The size of the stabilizing materials and/or vesicles of the present invention will depend upon the intended use. With smaller liposomes, resonant frequency ultrasound will generally be higher than for the larger liposomes. Sizing also serves to modulate resultant liposomal biodistribution and clearance. In addition to filtration, the size of the liposomes can be adjusted, if desired, by procedures known to one skilled in the art, such as shaking, microemulsification, vortexing, filtration, repeated freezing and thawing cycles, extrusion, extrusion under pressure through pores of a defined size, sonication, homogenization, the use of a laminar stream of a core of liquid introduced into an immiscible sheath of liquid. See, for example, U.S. Pat. Nos. 4,728,578, 4,728,575, 4,737,323, 4,533,254, 4,162,282, 4,310,505 and 4,921,706; U.K. Patent Application GB 2193095 A; International Applications PCT/US85/01161 and PCT/US89/05040; Mayer et al., *Biochimica et Biophysica Acta*, 858:161–168 (1986); Hope et al., *Biochimica et Biophysica Acta*, 812:55–65 (1985); Mayhew et al., *Methods in Enzymology*, 149:64–77 (1987); Mayhew et al., *Biochimica et Biophysica Acta*, 755:169–74 (1984); Cheng et al, *Investigative Radiology*, 22:47–55 (1987); and *Liposomes Technology*, Gregoriadis, G., ed., Vol. 1, pp. 29–37, 51–67 and 79–108 (CRC Press Inc, Boca Raton, Fla., 1984). The disclosures of each of the foregoing patents, publications and patent applications are hereby incorporated by reference herein in their entirety. Extrusion under pressure through pores of defined size is a preferred method of adjusting the size of the liposomes.

Since vesicle size influences biodistribution, different size vesicles may be selected for various purposes. For example, for intravascular application, the preferred size range is a mean outside diameter between about 30 nm and about 10 $\mu$m, with the preferable mean outside diameter being about 5 $\mu$m. More specifically, for intravascular application, the size of the vesicles is preferably about 10 $\mu$m or less in mean outside diameter, and preferably less than about 7 $\mu$m, and more preferably less than about 5 $\mu$m in mean outside diameter. Preferably, the vesicles are no smaller than about 30 nm in mean outside diameter. To provide therapeutic delivery to organs such as the liver and to allow differentiation of tumor from normal tissue, smaller vesicles, between about 30 nm and about 100 nm in mean outside diameter, are preferred. For embolization of a tissue such as the kidney or the lung, the vesicles are preferably less than about 200 $\mu$min mean outside diameter. For intranasal, intrarectal or topical administration, the vesicles are preferably less than about 100 $\mu$m in mean outside diameter. Large vesicles, between 1 and about 10 $\mu$m in size, will generally be confined to the intravascular space until they are cleared by phagocytic elements lining the vessels, such as the macrophages and Kupffer cells lining capillary sinusoids. For passage to the cells beyond the sinusoids, smaller vesicles, for example, less than about 1 $\mu$m in mean outside diameter, e.g., less than about 300 nm in size, may be utilized. In preferred embodiments, the vesicles are administered individually, rather than embedded in a matrix, for example.

For in vitro use, such as cell culture applications, the gas filled vesicles may be added to the cells in cultures and then incubated. Subsequently sonic energy can be applied to the culture media containing the cells and liposomes.

In carrying out the imaging methods of the present invention, the stabilizing materials and vesicle compositions can be used alone, or in combination with diagnostic agents, bioactive agents or other agents. Such other agents include excipients such as flavoring or coloring materials.

In the case of diagnostic applications, such as ultrasound and CT, energy, such as ultrasonic energy, is applied to at least a portion of the patient to image the target tissue. A visible image of an internal region of the patient is then obtained, such that the presence or absence of diseased tissue can be ascertained. With respect to ultrasound, ultrasonic imaging techniques, including second harmonic imaging, and gated imaging, are well known in the art, and are described, for example, in Uhlendorf, *IEEE Transactions on Ultrasonics, Ferroelectrics, and Frequency Control*, 14(1):70–79 (1994) and Sutherland, et al., *Journal of the American Society of Echocardiography*, 7(5):441–458 (1994), the disclosures of each of which are hereby incorporated herein by reference in their entirety. CT imaging techniques which are employed are conventional and are described, for example, in *Computed Body Tomography*, Lee, Sagel, and Stanley, eds., 1983, Ravens Press, New York, N.Y., especially the first two chapters entitled "Physical Principles and Instrumentation", Ter-Pogossian, and "Techniques", Aronberg, the disclosures of each of which are hereby incorporated by reference herein in their entirety.

Ultrasound can be used for both diagnostic and therapeutic purposes. In diagnostic ultrasound, ultrasound waves or a train of pulses of ultrasound may be applied with a transducer. The ultrasound is generally pulsed rather than continuous, although it may be continuous, if desired. Thus, diagnostic ultrasound generally involves the application of a pulse of echoes, after which, during a listening period, the ultrasound transducer receives reflected signals. Harmonics, ultraharmonics or subharmonics may be used. The second harmonic mode may be beneficially employed, in which the 2x frequency is received, where x is the incidental frequency. This may serve to decrease the signal from the background material and enhance the signal from the transducer using the targeted contrast media of the present invention which may be targeted to the desired site, for example, blood clots. Other harmonic signals, such as odd harmonics signals, for example, 3x or 5x, would be similarly received using this method. Subharmonic signals, for example, x/2 and x/3, may also be received and processed so as to form an image.

In addition to the pulsed method, continuous wave ultrasound, for example, Power Doppler, may be applied. This may be particularly useful where rigid vesicles, for example, vesicles formulated from polymethyl methacrylate, are employed. In this case, the relatively higher energy of the Power Doppler may be made to resonate the vesicles and thereby promote their rupture. This can create acoustic emissions which may be in the subharmnonic or ultraharmonic range or, in some cases, in the same frequency as the applied ultrasound. It is contemplated that there will be a spectrum of acoustic signatures released in this process and the transducer so employed may receive the acoustic emissions to detect, for example, the presence of a clot. In addition, the process of vesicle rupture may be employed to transfer kinetic energy to the surface, for example of a clot to promote clot lysis. Thus, therapeutic thrombolysis may be achieved during a combination of diagnostic and therapeutic ultrasound. Spectral Doppler may also be employed. In general, the levels of energy from diagnostic ultrasound are insufficient to promote the rupture of vesicles and to facilitate release and cellular uptake of the bioactive agents. As noted above, diagnostic ultrasound may involve the application of one or more pulses of sound. Pauses between pulses permits the reflected sonic signals to be received and analyzed. The limited number of pulses used in diagnostic ultrasound limits the effective energy which is delivered to the tissue that is being studied.

Higher energy ultrasound, for example, ultrasound which is generated by therapeutic ultrasound equipment, is generally capable of causing rupture of the vesicle composition. In general, devices for therapeutic ultrasound employ from about 10 to about 100% duty cycles, depending on the area of tissue to be treated with the ultrasound. Areas of the body which are generally characterized by larger amounts of muscle mass, for example, backs and thighs, as well as highly vascularized tissues, such as heart tissue, may require a larger duty cycle, for example, up to about 100%.

In therapeutic ultrasound, continuous wave ultrasound is used to deliver higher energy levels. For the rupture of vesicles, continuous wave ultrasound is preferred, although the sound energy may also be pulsed. If pulsed sound energy is used, the sound will generally be pulsed in echo train lengths of from about 8 to about 20 or more pulses at a time. Preferably, the echo train lengths are about 20 pulses at a time. In addition, the frequency of the sound used may vary from about 0.025 to about 100 megahertz (MHz). In general, frequency for therapeutic ultrasound preferably ranges between about 0.75 and about 3 MHz, with from about 1 and about 2 MHz being more preferred. In addition, energy levels may vary from about 0.5 Watt (W) per square centimeter ($cm^2$) to about 5.0 $W/cm^2$, with energy levels of from about 0.5 to about 2.5 $W/cm^2$ being preferred. Energy levels for therapeutic ultrasound involving hyperthermia are generally from about 5 $W/cm^2$ to about 50 $W/cm^2$. For very small vesicles, for example, vesicles having a diameter of less than about 0.5 $\mu$m, higher frequencies of sound are generally preferred because smaller vesicles are capable of absorbing sonic energy more effectively at higher frequencies of sound. When very high frequencies are used, for example, greater than about 10 MHz, the sonic energy will generally penetrate fluids and tissues to a limited depth only. Thus, external application of the sonic energy may be suitable for skin and other superficial tissues. However, it is generally necessary for deep structures to focus the ultrasonic energy so that it is preferentially directed within a focal zone. Alternatively, the ultrasonic energy may be applied via interstitial probes, intravascular ultrasound catheters or endoluminal catheters. In addition to the therapeutic uses discussed above, the present compositions can be employed in connection with esophageal carcinoma or in the coronary arteries for the treatment of atherosclerosis, as well as the therapeutic uses described, for example, in U.S. Pat. No. 5,149,319, the disclosure of which is hereby incorporated by reference herein in its entirety.

A therapeutic ultrasound device may be used which employs two frequencies of ultrasound. The first frequency may be x, and the second frequency may be 2x. In preferred form, the device would be designed such that the focal zones of the first and second frequencies converge to a single focal zone. The focal zone of the device may then be directed to the targeted compositions, for example, targeted vesicle compositions, within the targeted tissue. This ultrasound device may provide second harmonic therapy with simultaneous application of the x and 2x frequencies of ultrasound energy. It is contemplated that, in the case of ultrasound involving vesicles, this second harmonic therapy may provide improved rupturing of vesicles as compared to ultrasound energy involving a single frequency. Also, it is contemplated that the preferred frequency range may reside within the fundamental harmonic frequencies of the vesicles. Lower energy may also be used with this device. An ultrasound device which may be employed in connection with the aforementioned second harmonic therapy is described, for example, in Kawabata, et al., *Ultrasonics Sonochemistry*, 3:1–5 (1996), the disclosure of which is hereby incorporated by reference herein in its entirety.

For use in ultrasonic imaging, preferably, the vesicles of the invention possess a reflectivity of greater than 2 dB, more preferably between about 4 dB and about 20 dB. Within these ranges, the highest reflectivity for the vesicles of the invention is exhibited by the larger vesicles, by higher concentrations of vesicles, and/or when higher ultrasound frequencies are employed.

For therapeutic drug delivery, the rupturing of the bioactive agent containing the targeted therapeutic delivery systems of the invention is surprisingly easily carried out by applying ultrasound of a certain frequency to the region of the patient where therapy is desired, after the liposomes have been administered to or have otherwise reached that region, e.g., via delivery with targeting ligands. Specifically, it has been unexpectedly found that when ultrasound is applied at a frequency corresponding to the peak resonant frequency of the bioactive agent containing gas filled vesicles, the vesicles will rupture and release their contents. The peak resonant frequency can be determined either in vivo or in vitro, but preferably in vivo, by exposing the stabilizing materials or vesicles, including liposomes, to ultrasound, receiving the reflected resonant frequency signals and analyzing the spectrum of signals received to determine the peak, using conventional means. The peak, as so determined, corresponds to the peak resonant frequency, or second harmonic, as it is sometimes termed.

Preferably, the compositions of the invention have a peak resonant frequency of between about 0.5 and about 10 MHz. Of course, the peak resonant frequency of the gas filled vesicles of the invention will vary depending on the outside diameter and, to some extent, the elasticity or flexibility of the liposomes, with the larger and more elastic or flexible liposomes having a lower resonant frequency than the smaller and less elastic or flexible vesicles.

The bioactive agent containing gas filled vesicles will also rupture when exposed to non-peak resonant frequency ultrasound in combination with a higher intensity (wattage) and duration (time). This higher energy, however, results in greatly increased heating, which may not be desirable. By adjusting the frequency of the energy to match the peak resonant frequency, the efficiency of rupture and release is improved, appreciable tissue heating does not generally occur (frequently no increase in temperature above about 2° C.), and less overall energy is required. Thus, application of ultrasound at the peak resonant frequency, while not required, is most preferred.

For diagnostic or therapeutic ultrasound, any of the various types of diagnostic ultrasound imaging devices may be employed in the practice of the invention, the particular type or model of the device not being critical to the method of the invention. Also suitable are devices designed for administering ultrasonic hyperthermia, such devices being described in U.S. Pat. Nos. 4,620,546, 4,658,828, and 4,586,512, the disclosures of each of which are hereby incorporated herein by reference in their entirety. Preferably, the device employs a resonant frequency (RF) spectral analyzer. The transducer probes may be applied externally or may be implanted. Ultrasound is generally initiated at lower intensity and duration, and then intensity, time, and/or resonant frequency increased until the vesicle is visualized on ultrasound (for diagnostic ultrasound applications) or ruptures (for therapeutic ultrasound applications).

Although application of the various principles will be readily apparent to one skilled in the art, in view of the present disclosure, by way of general guidance, for gas filled vesicles of about 1.5 to about 10 $\mu$m in mean outside diameter, the resonant frequency will generally be in the range of about 1 to about 10 MHz. By adjusting the focal zone to the center of the target tissue (e.g., the tumor) the gas filled vesicles can be visualized under real time ultrasound as they accumulate within the target tissue. Using the 7.5 MHz curved array transducer as an example, adjusting the power delivered to the transducer to maximum and adjusting the focal zone within the target tissue, the spatial peak temporal average (SPTA) power will then be a maximum of approximately 5.31 $mW/cm^2$ in water. This power will cause some release of bioactive agents from the gas filled vesicles, but much greater release can be accomplished by using a higher power.

By switching the transducer to the doppler mode, higher power outputs are available, up to 2.5 W/cm$^2$ from the same transducer. With the machine operating in doppler mode, the power can be delivered to a selected focal zone within the target tissue and the gas filled vesicles can be made to release their contents, including bioactive agents. Selecting the transducer to match the resonant frequency of the gas filled vesicles will make this process of release even more efficient.

For larger diameter gas filled vesicles, e.g., greater than 3 μm in mean outside diameter, a lower frequency transducer may be more effective in accomplishing therapeutic release. For example, a lower frequency transducer of 3.5 MHz (20 mm curved array model) may be selected to correspond to the resonant frequency of the gas filled vesicles. Using this transducer, 101.6 mW/cm$^2$-may be delivered to the focal spot, and switching to doppler mode will increase the power output (SPTA) to 1.02 W/cm$^2$.

To use the phenomenon of cavitation to release and/or activate the prodrugs within the gas filled stabilizing materials and/or vesicles, lower frequency energies may be used, as cavitation occurs more effectively at lower frequencies. Using a 0.757 MHz transducer driven with higher voltages (as high as 300 volts) cavitation of solutions of gas-filled liposomes will occur at thresholds of about 5.2 atmospheres.

The table below shows the ranges of energies transmitted to tissues from diagnostic ultrasound on commonly used instruments such as the Piconics Inc. (Tyngsboro, Mass.) Portascan general purpose scanner with receiver pulser 1966 Model 661; the Picker (Cleveland, Ohio) Echoview 8L Scanner including 80C System or the Medisonics (Mountain View, Calif.) Model D-9 Versatone Bidirectional Doppler. In general, these ranges of energies employed in pulse repetition are useful for diagnosis and monitoring gas-filled liposomes but are insufficient to rupture the gas-filled liposomes of the present invention.

TABLE 6

Power and Intensities Produced by Diagnostic Equipment*

| Pulse repetition rate (Hz) | Total ultrasonic power output P (mW) | Average Intensity at transducer face $I_{TD}$ (W/m$^2$) |
| --- | --- | --- |
| 520 | 4.2 | 32 |
| 676 | 9.4 | 71 |
| 806 | 6.8 | 24 |
| 1000 | 14.4 | 51 |
| 1538 | 2.4 | 8.5 |

*Values obtained from Carson et al., Ultrasound in Med. & Biol., 3:341–350 (1978), the disclosure of which is hereby incorporated herein by reference in its entirety.

Either fixed frequency or modulated frequency ultrasound may be used. Fixed frequency is defined wherein the frequency of the sound wave is constant over time. A modulated frequency is one in which the wave frequency changes over time, for example, from high to low (PRICH) or from low to high (CHIRP). For example, a PRICH pulse with an initial frequency of 10 MHz of sonic energy is swept to 1 MHz with increasing power from 1 to 5 watts. Focused, frequency modulated, high energy ultrasound may increase the rate of local gaseous expansion within the liposomes and rupturing to provide local delivery of therapeutics.

Where the gas filled targeted therapeutic delivery systems are used for drug delivery (including steroid prodrugs and/or targeting ligands), the bioactive agent to be delivered may be embedded within the wall of the vesicle, encapsulated in the vesicle and/or attached to the surface of the vesicle. The phrase "attached to" or variations thereof, as used herein in connection with the location of the bioactive agent, means that the bioactive agent is linked in some manner to the inside and/or the outside wall of the microsphere, such as through a covalent or ionic bond or other means of chemical or electrochemical linkage or interaction. The phrase "encapsulated in variations thereof" as used in connection with the location of the bioactive agent denotes that the bioactive agent is located in the internal microsphere void. The phrase "embedded within" or variations thereof as used in connection with the location of the bioactive agent, signifies the positioning of the bioactive agent within the vesicle wall(s) or layer(s). The phrase "comprising a bioactive agent" denotes all of the varying types of positioning in connection with the vesicle. Thus, the bioactive agent can be positioned variably, such as, for example, entrapped within the internal void of the gas filled vesicle, situated between the gas and the internal wall of the gas filled vesicle, incorporated onto the external surface of the gas filled vesicle, enmeshed within the vesicle structure itself and/or any combination thereof. The delivery vehicles may also be designed so that there is a symmetric or an asymmetric distribution of the drug both inside and outside of the stabilizing material and/or vesicle.

Any of a variety of bioactive agents may be encapsulated in the vesicles. If desired, more than one bioactive agent may be applied using the vesicles. For example, a single vesicle may contain more than one bioactive agent or vesicles containing different bioactive agents may be co-administered. By way of example, a monoclonal antibody capable of binding to melanoma antigen and an oligonucleotide encoding at least a portion of IL-2 may be administered at the same time. The phrase "at least a portion of" means that the entire gene need not be represented by the oligonucleotide, so long as the portion of the gene represented provides an effective block to gene expression. Preferably, at least one of the bioactive agents is a steroid prodrug. More preferably, one of the bioactive agents is a steroid prodrug and another bioactive agent is a targeting ligand.

A gas filled vesicle filled with oxygen gas should create extensive free radicals with cavitation. Also, metal ions from the transition series, especially manganese, iron and copper can increase the rate of formation of reactive oxygen intermediates from oxygen. By encapsulating metal ions within the vesicles, the formation of free radicals in vivo can be increased. These metal ions may be incorporated into the liposomes as free salts, as complexes, e.g., with EDTA, DTPA, DOTA or desferrioxamine, or as oxides of the metal ions. Additionally, derivatized complexes of the metal ions may be bound to lipid head groups, or lipophilic complexes of the ions may be incorporated into a lipid bilayer, for example. When exposed to thermal stimulation, e.g., cavitation, these metal ions then will increase the rate of formation of reactive oxygen intermediates. Further, radiosensitizers such as metronidazole and misonidazole may be incorporated into the gas filled vesicles to create free radicals on thermal stimulation.

Although not intending to be bound by any particular theory of operation, an example of the use of the steroid prodrugs of the present invention includes attaching an acylated chemical group to the steroid via an ester linkage which would readily cleave in vivo by enzymatic action in serum. The acylated steroid prodrug may then be incorporated into the gas filled vesicle or stabilizing material. Thereafter, the steroid prodrug may be delivered to the appropriate tissue or receptor via a targeting ligand. Upon reaching the desired tissue or receptor, the gas filled vesicle may be ruptured or popped by the sonic pulse from the ultrasound, and the steroid prodrug encapsulated by the vesicle may then be exposed to the serum. The ester linkage may then be cleaved by esterases in the serum, thereby generating the steroid. However, it is not necessary for the steroid to be cleaved from the acylated chemical group and ester linkage in order for the steroid to be therapeutically effective. In other words, the steroid prodrug may retain the bioactivity of the steroid.

Similarly, ultrasound may be utilized not only to rupture the gas filled vesicle, but also to cause thermal effects which may increase the rate of the chemical cleavage and the release of the active drug from the prodrug (e.g., release of the steroid from the linking group and lipid moiety). The particular chemical structure of the bioactive agents may be selected or modified to achieve desired solubility such that the bioactive agent may either be encapsulated within the internal gas filled space of the vesicle, attached to the surface of the vesicle, embedded within the vesicle and/or any combination thereof. The surface-bound bioactive agent may bear one or more acyl chains such that, when the vesicle is ruptured or heated or ruptured via cavitation, the acylated bioactive agent may then leave the surface and/or the bioactive agent may be cleaved from the acyl chain chemical group. Similarly, other bioactive agents may be formulated with a hydrophobic group which is aromatic or sterol in structure to incorporate into the surface of the vesicle.

Elevated temperature, such as in inflamed joints caused by rheumatoid arthritis, can be used as a complimentary mechanism for delivering entrapped steroid prodrugs from the walls of a vesicle containing a temperature sensitive precursor matrix. While not intending to be bound by any particular theory of operation, this method relies, in part, on the phenomenon of elevated local temperature typically associated with disease, inflammation, infection, etc. Such conditions, which may also be referred to as physiological stress states, may elevate the temperature in a region of the patient, by a fraction of a degree or as much as 1, 2, 3, 4, 5, 6, 7, 8, 9, 10, or more degrees. For example, although normal human body temperature is about 37° C., tissue affected by disease, inflammation, infection, etc. can have temperatures greater than about 37° C., such as, for example, about 40° C. By incorporating materials which are liquid at normal physiological temperatures (i.e. the temperature of a particular mammal under normal circumstances) and which undergo a phase transition to form a gas at the elevated temperature, the methods of the present invention allow steroid prodrugs to be effectively delivered to the affected tissue and advantageously released at that site. When the gaseous precursor, for example, undergoes a phase transition from a liquid or solid to a gas, steroid prodrugs carried within the gaseous precursor may be released into the region of the tissue thereby effecting delivery of the steroid prodrug to the region of need. Thus, in accordance with the present method, other regions of the patient not affected by the regionalized condition of increased temperature are bypassed, and the steroid prodrug is selectively delivered to the region in need.

The delivery of the steroid prodrug to a desired tissue or region of the body is activated when the local temperature is at or above the phase transition temperature of the gaseous precursor. As the vesicle or non-vesicular composition or vesicles containing the gaseous precursor circulates through the patient's body, it will pass through tissues via the vasculature. As the gaseous precursor passes through a tissue or region which is at the phase transition temperature of the gaseous precursor, it will undergo transition to a gaseous state. While not intending to be bound by any particular theory of operation, it is believed that the expansion of the gaseous precursor during the phase transition forces the steroid prodrug from the vesicle or non-vesicular composition allowing it to settle in the desired region of the patient. In a preferred embodiment of the invention, the delivery of a steroid prodrug is accomplished simply due to the increase in temperature in a tissue or region associated with disease, infection, inflammation, etc within the tissue or region.

Preferably, the gaseous precursor forms a gas at the desired tissue or region of the body, which may be at an elevated temperature as compared to the normal body temperature, due to disease, infection, inflammation, etc. However, external heat (i.e., heat from a source other than the elevated physiological temperatures of the region) also may be applied to increase the temperature within a region or tissue of a patient, if desired. External heat may be applied by any means known in the art, such as, for example, microwave, radiofrequency, ultrasound, and other local application of heat. Local application of heat may be accomplished; for example, by a water bath or blankets. A temperature increase in a desired tissue or region of the body may be achieved by implantation of interstitial probes or insertion of a catheter, in combination with the application of an oscillating magnetic field or ultrasound energy. If ultrasound energy is used, the ultrasound energy may also interact with the gaseous precursor and/or stabilizing material, and may facilitate conversion of the gaseous precursor to a gas and/or release of a bioactive agent. As will be apparent to those skilled in the art, applied ultrasound energy may be pulsed, swept, or varied to facilitate interaction with the gaseous precursor and stabilizing material. Diagnostic ultrasound may be used in order to visualize the gaseous precursors as the gas is formed, and to visualize the tissue or region of interest.

EXAMPLES

The invention is further demonstrated in the following examples. Examples 2, 16, 20, and 21 are actual examples and Examples 1, 3–15, 17–19, and 22 are prophetic examples. The examples are for purposes of illustration and are not intended to limit the scope of the present invention.

Example 1

AALs were made by mixing 1.5 mls of MRX115 precursor with 320 ul of soybean oil. Dipalmitoyl Phosphoethanolamine labeled with 7-nitro, 2,1-benzoxadiazol-4yl (NBD) was added to the soybean oil at a concentration of 0.5 mg/ml. The mixture was placed into a 2 ml Wheaton vial and the headspace removed and replaced with perfluorobutane. The vials were then shaken for 60 seconds on an Espe CAPMIX. A sucrose gradient was created in a 50 ml oakridge tube by mixing equal parts of a 10% and a 90% sucrose solution. The centrifuge tube was placed into the Beckman TJ-6 tabletop centrifuge in a TH-4 swinging bucket rotor for 30 minutes to form the gradient. Three samples were combined and added to each gradient tube. Foam height was measured with a Toyo digital micrometer. The mixtures were then spun for 30 minutes to separate bubble held material from free. The foam height was again measured by micrometer to determine total foam conversion. Samples were then taken from the vial (pre) and from the gradient tube. These were aliquotted into 96 well plates and assayed with a Molecular Devices fMax flourometer.

The following data was obtained showing increased payload of entrapped NBD for AALs of comparable size and phospholipid composition as MRX-115 especially at the 5 and 10 mg/ml phospholipid concentrations.

TABLE 7

| Total P-lipid conc. | particle size | particle conc. | Mean foam ht. | Dye retention % |
|---|---|---|---|---|
| 1 mg/ml | 3.49 μM | $4.44 \times 10^8$ | 21.05 mm | 23.21 |
| 5 mg/ml | 2.22 μM | $2.21 \times 10^9$ | 41.31 mm | 70.11 |
| 10 mg/ml | 1.67 μM | $3.93 \times 10^9$ | 38.77 mm | 49.65 |
| MRX-115 | | | | |
| 1 mg/ml | 2.81 μM | $4.12 \times 10^8$ | 55.46 mm | 23.94 |
| 5 mg/ml | 1.75 μM | $7.30 \times 10^9$ | 55.21 mm | 24.36 |
| 10 mg/ml | 2.66 μM | $8.15 \times 10^8$ | 60.05 mm | 10.87 |

Example 2

The procedure used in Example 1 was followed, adding 0.5 units/ml of urokinase (Sigma Chemical Co., St. Louis, Mo.) to the labeled DPPE in the experimental sample. Data presented below show effectiveness of entrappment in soybean AALs. The numbers represent a fluorescence measurement (proporational to the amount of labelled DPPE that releases into solution indicating liposome rupture.)

| | |
|---|---|
| Control - No urokinase, no soybean oil | 881.3 |
| Urokinase in lipid (no oil) | 704.2 |
| Urokinase in lipid + soybean oil | 707.6 |

The data shows that soybean oil and urokinase somewhat stabilize the lipid vesicle from rupture and provide a good indication that urokinase incorporates into the AAL as well as into a conventional liposome.

Example 3

Preparation of lipospheres without PFC. Soybean oil (volume=160 microliters), (Procter & Gamble, Cincinnati, Ohio) was suspended in 1 ml of a mixture containing an 8:1:1 weight by weight of normal saline to propylene glycol to glycerol. The liquid also contained lipids comprising 1 mg per ml of 82 mole percent dipalmitoylphosphatidylcholine (DPPC), 10 mole percent dipalmitoylphosphatidic acid (DPPA) and 8 mole percent dipalmitoylphosphatidylethanolarine-polyethyleneglycol (DPPE-PEG5,000). All of the lipids were purchased from Avanti Polar Lipids, Alabaster, Ala. The liquid was sealed in an 2 ml vial and shaken on an Espe Capmix$^R$ dental amalgamator for 45 seconds at 4,500 RPM. The resulting lipospheres were studied on an Nihon Diaphot 200 microscope at 500× magnification. The mean particle size was about 5 microns with appreciable particles over 50 microns in size. The particles appeared as concentric spheres with a peripheral layer of lipid and a central homogenous compartment of oil.

Example 4

Preparation of lipospheres without PFC, addition of Sudan Black Dye. The above Example #1 was susbstantially completed except that 150 micrograms of the lipophilic dye Sudan Black (Sigma Chem. Co., St. Louis, Mo.) was dissolved into 160 microliters of the soybean oil prior to the oil being added to the liquid suspension of lipids. After the lipospheres were prepared via agitation as above, these were again studied on the microscope. A homogeneous greyish interior was seen seen in the interior of the lipospheres. The Sudan Black was seen to be entrapped within the lipospheres and no appreciable Sudan Black was present on the outside of the lipospheres. As the amount of Sudan Black was increased to 320 microliters the lipospheres appeared darker but Sudan Black was not present ouside of the lipospheres. The size of the lipospheres as shown by microscopy was similar for lipospheres with and without Sudan Black.

Example 5

Preparation of lipospheres with PFC- Formation of Acoustically Active Lipospheres (AAL's). Demonstration of smaller size and increased particle count. The above of Example #1 was repeated except that 20 microliters of perfluorohexane was added to the vial.

As shown in table 2 below the AALs shaken with the PFC present within the lipid/oil suspension had higher particle count and lower mean particle size.

TABLE 8

Sizes and Concentrations of Various AAL Formulations

| Lipid | Conc. | Oil | Gas | Mean Size (μm) | Particles/ml |
|---|---|---|---|---|---|
| 1.DPPC | 1 mg/ml | Soybean | $C_4F_{10}$ | 3.55 | $2.08 \times 10^9$ |
| 2.DPPC | 1 mg/ml | Canola | $C_4F_{10}$ | 4.02 | $2.30 \times 10^9$ |
| 3.DPPC | 1 mg/ml | Canola | $C_6F_{14}$ | 4.46 | $2.17 \times 10^9$ |
| 4.DPPC | 5 mg/ml | Canola | $C_4F_{10}$ | 3.39 | $3.63 \times 10^9$ |
| 5.DPPC | 1 mg/ml | Canola | air | 3.61 | $2.41 \times 10^9$ |
| 6.DPPC | 5 mg/ml | Canola | air | 3.53 | $3.36 \times 10^9$ |
| 7.DSPC | 1 mg/ml | Canola | $C_4F_{10}$ | 4.57 | $1.09 \times 10^9$ |
| 8.DSPC | 5 mg/ml | Canola | $C_4F_{10}$ | 3.04 | $4.63 \times 10^9$ |

DPPC - dipalmitoylphospatidylcholine, DSPC - disteroylphospatidylcholine

Example 6

The procedure in Example 3 was repeated except that 320 microliters of Sudan Black was added to the lipids/oil/PFC mixture prior to shaking. As in Example 2, the black dye was contained within the microspheres and not seen free within the surrounding medium. The size and count of particles was similar to Example 3 (See Table 2). On microscopic study the perfluorohexane microspheres were shown to contain a peripheral rim of grey or dark material (Sudan Black dye) and a central clear spherical region.

Example 7

The procedure of Example 1 was repeated except that the head space of the vial was evacuated and replaced with perfluorobutane gas. The vial with headspace of perfluorobutane gas was shaken on the amalgamator. Particle sizing was performed see Table 1. Microscopy showed that the particles has a translucent periphery (presumably oil) and a clear central region (presumably gas).

Example 8

The procedure of Example 2 was repeated except that the head space was replaced with perfluorobutane as in Example 5. The dark dye was seen in the periphery of the particles (dye and oil) and the center (gas) appeared clear. The size of the particles (see Table 2 below) was similar to the particles of Example 5.

Example 9

The attenuation of the AAL specified in line 1 of the table in Example 5 above was tested using a 2.25 Mhz transducer (KB-Aerotech, Lewistown, Pa.) in pulse-echo mode. The transducer was driven by a Panametric 5052PR pulser/receiver (Waltham Mass.). One tenth ml of the agent was injected into a 450 ml cylindrical chamber filled with ddI water at room temperature. Reflected echoes from the backwall were received by the same transducer and displayed on an oscilloscope. Peak to peak amplitude was measured immediately prior to and throughout the duration of the test and recorded at 1 min. intervals for 30 minutes post injection of contrast agent. A 10b kHz transducer (Matec, Northborough, Mass.) was turned on for 5 minutes following the injection of contrast agent to activate the AALs. Two different acoustic fields were used for this purpose. First the transducer was operated in continuous mode at its center frequency. The maximum amplitude of peak to peak acoustic pressure was 2.6 kilopascals. Next the transducer was operated in pulsed mode with a pulse repitition frequency of 1 kHZ and a burst number of 7. The maximum amplitude of peak to peak acoustic pressure at this setting was 5.5 kilopascals. To examine the efficacy of acoustic activation, the experiment was repeated without the 100 kHz transducer.

Attenuation Coefficients are calculated as follows: A.C. in [dB/cm]=20($\log_{10}${[P-$P_{APC}$]/[P-$P_{AOPC}$]})divided by 2× chamber diameter where APC is amplitude pre-contrast and AOPC is amplitude post-contrast.

As shown in FIG. 7, the 100 kHz transducer ruptures essentially all the microbubbles in the pulsed mode. The pulsed mode is more effective than the continuous wave mode in rupturing the vesicles. This is because the pulsed mode generates a larger peak pressure than the continuous mode. Preferably the peak pressure of the ultrasound is between one kilopascal to 10 Megapascals and most preferably between 10 kilopascals and 5 megapascals. Frequency ranges vary between about 20 kHz to 50 Mhz.

Example 10
Use of AALs with an Optional Targeting Moiety

The linear peptide CRGDC was synthesized by standard solid phase methodology using alpha amino-FMOC protection. This procedure will involve the use of the fluorenylmethoxycarbonyl (FMOC) protecting group on the α-amino moiety of the protected amino acids. In this case, the protected Valine (FMOC-Val) will be bound to the resin, using diisopropylethylamine (DIEA) and ethyl acetate with subsequent refluxing. Briefly, 3-Nitro4-bromometyl-benzoylamide polystyrene resin will be prepared as described in Rich, D. H. and Gurwara, S. K., *J. Am. Chem. Soc.*, 97:6, 1575–1579, Mar. 19, 1975, the disclosures of which are hereby incorporated herein by reference, in their entirety. To this resin will be added Boc-Valine (Bachem, Torrance, Calif.) (0.6 mmole, 1 equiv.) with diisopropylethylamine (Mallinckrodt, St. Louis, Mo.) (0.6 mmole, 1 eq.) in ethyl acetate (Mallinckrodt, St. Louis, Mo.) and refluxing. The remaining protected amino acids will then be coupled using standard coupling methodology. Deprotection of the Boc group will be achieved by exposing the resin to 45% trifluoroacetic acid (TFA) in anhydrous methylene chloride (v:v) for 2 minutes followed by removal of the acid. A second rinse with 45% TFA/$CH_2Cl_2$ for 20 minutes will then be performed. The resin will be washed twice with $CH_2Cl_2$ and neutralized with 2×2 minute additions of 10% diisopropylethylamine (DIEA) (Mallinckrodt, St. Louis, Mo.) in $CH_2Cl_2$ followed by 2×2 minute rinses with $CH_2Cl_2$. Amino acids will be coupled to the amino terminus of the deprotected Valine residue via the addition of the appropriate Boc-amino acid (1.2 mmoles, 2 equiv.) and diisopropylcarbodiimide (DIC) (Aldrich Chemical, Milwaukee, Wis.) (1.2 mmole, 2 equiv.), hydroxybenzotriazole (HOBT) (Aldrich, Milwaukee, Wis.) (1.2 equiv.) and N-methylpyrrolidone (Mallinckrodt, St. Louis, Mo.). Coupling will be monitored for completion using the method of Kaiser et al., *Anal. Biochem.*, 34, 595, 1970, the disclosures of which are incorporated herein by reference, in their entirety. Incomplete couplings will require a repeat coupling. After coupling, the resin will be washed with 2×2 minute washes of $CH_2Cl_2$. The remaining protected amino acids will be coupled in the same manner to provide the CRGDC-resin complex. Following binding of the FMOC-Val to the resin, further couplings will be initiated as set forth below.

Deprotection followed using 20% pyridine/N-methyl pyrollidone. The FMOC-Val resin complex will be washed 5×1 min with dimethylformide (DMF) or N-methylpyrrolidone (NMP). The FMOC groups will be removed with 20% piperidine/NMP×20 min. This will be repeated, followed by a wash 5×1 min with DMF or NMP.

An appropriate FMOC protected amino acid (2 equiv.) will be added with 2 equiv of DIC or dicyclohexylcarbodiimide (DCC), hydroxybenzotriazole (2 equiv.) and DMF or NMP. Completeness of the coupling reactions will be monitored using the ninhydrin detection method of Kaiser.

The steps set forth above will be repeated for coupling of additional FMOC- protected amino acids.

The peptide CRGDC requires only the sidechain protection of the lysines. A number of protecting group schemes are compatible with the synthetic scheme. For example, Boc-Lys with a fluorenylmethoxycarbonyl (FMOC) sidechain protecting group may be used to prevent the reaction of other amino acids, PEG, or the DPGS with the side chain group. In addition, a Boc-Asp with a β-carboxyfluorenylmethyl (OFm) ester bond may be used to protect the sidechain carboxyl. Prior to removal of the DPGS-PEG-CRGDC from the resin, mild conditions as 20% piperidine and N-methylpyrrolidone can be initiated to remove both the FMOC group from the lysine.

In addition, a number of sidechain protecting groups may be used compatible with FMOC methodology yet require only mild conditions for removal. For example, FMOC-Asp-(O-Dmab)—OH and FMOC Lys-(Dde)—OH, where Dmab is 4-(N)-[1-(4,4-dimethyl-2,6-dioxocyclohexylidene)-3-methylbutyl]amino)benzyl ester and Dde is 1-(4,4 dimethyl-2,6-dioxocyclohex-1-ylidene) ethyl, can be used in part B of the synthesis with subsequent cleavage of the sidechain groups using 2% hydrazine in NMP, DMF, or $CH_2Cl_2$ for one hour. After removal of the sidechains, the DPGS-PEG-CRGDC will be washed with 2×2 min. NMP.

The resin of choice is a photolabile resin as used by Rich and Gurwara, (1975) J. Am. Chem. Soc. 97:1575–1579. The sidechain guanidinium of arginine was protected by a Cbz (carbobenzyloxy) group (Bachem, Torrance, Calif.). DPPA was then coupled to the peptide by the standard diisopropylcarbodiimide/hydroxybenzotriazole coupling. The Cbz protecting group was removed by hydrogenation ($H_2$+Pd or Pt). The composited compound is cleaved from the resin using irradiation from a 450W Hanovia arc lamp. The product is ten partially purified using size exclusion chromatography. Cyclization of the cystiene thiol groups is achieved by dissolving the peptide in water with pH adjusted with glacial acetic acid to 4.0. Potassium ferricyanate is added with stirring past a formal concentration of 0.1M added slowly until the yellow color persists. pH is then adjusted to 7.0 with triethylamine and the solution is frozen and lyophilized to yield a crude product. This material can be purified by reverse phase HPLC. The purified peptide conjugate is then incubated with any of the AAL compositions of the invention.

Example 11

Dexamethasone is chosen because it is a highly potent hydrophobic antiinflammatory drug. Dexamethasone is soluble at 100 mg/L in water. A mixture is created by adding 80 mg of a PEG Telomer B (DuPont, Wilmington, Del.) to 20 mg of dexamethasone. The mixture is dissolved in methanol and rotary evaporated under vacuum until it is a dry film. The film is subjected to hard vacuum (12 millitorr) overnight. The film is reconstituted in deionized water at 10 mg/ml and sonicated for 15 minutes at 90 watts. The resulting suspension is homogeneous. One milliliter of this mixture is administered to a Sephacryl S-200-HR column (½ inch by 7 inches) running in deionized water at 1 ml/minute, collecting 3 ml fractions. The fractions are frozen in liquid nitrogen and lyophilized. The lyophilized fractions are dissolved or reconstituted in 5 mls of methanol and scanned at 235 nm in the UV spectrophotometer. The absorbance maximum for dexamethasone in methanol is 235–238 nm as determined by dissolving dexamethasone in methanol and scanning from 320 nm through 220 nm. Pure methanol is scanned between 320 nm and 190 nm and found to have no absorbance below 210 nm. All samples are zeroed on pure methanol before scanning to prevent any carryover between samples. A standard curve is constructed from dexamethasone in methanol at 237 nm peak absorbance. The standard curve is between 2.5 and 25 µg/ml. The fractions that contained PEG Telomer B were suspensions and may not be scanned accurately. The remaining fractions are scanned and presumably contained the free, unentrapped dexamethasone. The majority of the dexamethasone absorbance is in fractions 11 through 15. The entire recovered free dexamethasone is only 7.3 µg. 200 microliters of a 10 mg/ml reconstituted solution, dissolved in methanol and measured at UV 235 nm, demonstrates that 20% of the PEG-Telomer B aggregate complex is dexamethasone. The experiment showed the high payload efficiency of the fluorosurfactant aggregation technique.

The lyophilized material comprising dexamethasone plus fluorosurfactant (20 mgs of PEG Telomer B) from Example 1 is suspended in 1.5 mls of soybean oil in a Teflon coated stoppered vial. To the headspace above the suspension 0.1 ml of perfluorobutane is added, initially at 0° C. The suspension is then warmed to room temperature and shaken on an ESPE Capmix. A sample of the suspension is then subjected to ultrasound from a horn sonicator and dB reflectivity was measured. The dexamethasone is detected by UV-visible spectrophotometry in lipid fractions prior to Horn-sonication and in non-lipid fractions following Horn sonication, indicating successful release of the drug.

Example 12
Preparation of Acoustically Active Lipospheres

One gram of α-tocopherol, 1.0 gram of retinoic acid and 3 grams of soybean oil are agitated in a vortex mixer. To this mixture is added 1.0 g. of a lipid blend consisting of 82 mol percent DPPC, 10 mol percent DPPA and 8 mol percent DPPE-PEG5000 (all phospholipids from Avanti Polar Lipids, Alabaster, Ala.). The mixture is stirred 10 minutes at 50° C. then transferred into a container with 200 mls normal saline plus 1% w/v Pluronic F-65 and emulsified with a Microfluidizer (10×) at 16,000 psi while the temperature is maintained at 50° C. The material is then subdivided into 1.0 ml aliquots in 1.5 ml vials. The vials are vacuum-evacuated, and the headspace is filled with perfluorobutane. The resulting product is a suspension of drug in oil filled liposomes or lipospheres containing about 0.45% by weight a-tocopherol and 0.45% by weight retinoic acid. The vials are sealed and placed on a Wig-L-Bug (Crescent Dental, Lyons Ill.) and agitated at 2800 rpm for 2 minutes. The final product consists of acoustically active liposheres instilled with perfluorobutane gas, with a mean diameter under 10 µm. The product can be injected in this form or filtered to eliminate particles over 2 µm just prior to injection.

Example 13
Use of Acoustically Active Drug Carriers for Treating Eye Disease

The product described in Example 12 is injected into the antecubital vein of a patient with macular degeneration. Ultrasound energy is applied to the eye using a 3 MHz transducer and Power Doppler. Imaging is performed simultaneously. Power is increased such that a robust second harmonic signal is obtained from the eye as the microbubbles flow through the retinal circulation. High concentrations of antioxidants are delivered to the retina. The patient's disease progression is slowed by virtue of the high concentration of antioxidants.

Example 14
Use of Acoustically Active Drug Carriers for Treating Eye Disease

A horn sonicator (Heat Systems Probe, Farmingdale N.Y.) is placed into the cornea of the eye of a rabbit and ultrasound energy is applied at 25 KHz, power level 2, for 5 minutes following intravenous injection of the acoustically active liposheres described in Example 12.

Example 15
Preparation of Acoustically Active Liposheres Containing Taxol

Example 12 is repeated substituting an equivalent quantity of taxol for the α-tocopherol, and retinoic acid. The preparation is used to treat neoplasms of the eye in patients with retinoblastoma or ocular melanoma by applying ultrasound to the eye.

Example 16
Preparation of Acoustically Active Liposheres Containing Amphotericin Amphotericin B (Bristol-Myers Squibb, Princeton, N.J.) was dissolved in soybean oil at 2 mg/ml. 1.5 mls of the lipid mixture from Example 15 was mixed with 80 µl of the Amphotericin-B solution and 7.5 µl of Pluronic F-68 (Spectrum Chemicals, Gardena, Calif.) was added. The headspace of the vial was evacuated by vacuum and replaced with perfluorobutane. The mixture was shaken for one minute on an ESPE-Capmix (Seefeld, Germany). The bubbles visibly incorporated Amphotericin as demonstrated by their yellow color. They were acoustically active and had a weighted mean size of 1.5 µm. The amphotericin was detected by UV-visible spectrophotometry in lipid fractions prior to Horn-sonication and in non-lipid fractions following Horn sonication, indicating successful release of the drug.

Example 17
Use of Acoustically Amphotericin-laden Microspheres to Treat Fungal Ophthalmitis In a patient with severe fungal ophthalmitis, the acoustically active liposheres of Example 16 are injected intravenously and ultrasound is applied to the eye using a 1 MHz continuous wave device at 0.5 watts/cm$^2$ and a 10% duty cycle. The ultrasound energy is applied to the eye for 10 minutes following the injection of the liposheres, eradicating fungal disease from the eye.

Example 18
Acoustically Active Oil Emulsion of Bendazac for Retinitis Pigmentosa Although bendazac salts, especially the lysine derivative are water soluble, free bendazac is lipid soluble and thus amenable to the embodiments of the invention for oil-solubilized liposheres. Acoustically active dispersions of bendazac for the treatment of retinitis pigmentosa are prepared as for amphotericin B in Example 16 and may be applied to the eye as in Example 17.

Example 19
Acoustically Active Emulsion of Doxazosin for the Treatment of Benign Prostatic Hyperplasia An optically active form of doxazosin, designated prazosin, U.S. Pat. No. 4,188,390, the (+) isomer of 4-amino-2-[4-(1,4-benzodioxan-2-carbonyl)piperazin-1-yl]-6,7-dimethoxyquinazoline also known as 1-(4-amino-6,7-dimethoxy-2-quinazolinyl)4-[(2,3-dihydro-1,4-benzodioxan-2-yl)carbonyl]piperazine was dissolved in soybean oil at a concentration of 3 mg/ml. 1.5 mls of the lipid mixture from Example 13 was mixed with 100 µl of the prazosin solution and 7.5 µl of Pluronic F-68 (Spectrum Chemicals, Gardena Calif.) was added. The headspace of the vial was evacuated by vacuum and replaced with perfluorobutane. The mixture was shaken for one minute on an ESPE-Capmix. The liposheres were acoustically active and had a weighted mean size of 1.2 µm.

Isolated human urethra contracted by noradrenaline is relaxed completely by prazosin. Furthermore, prazosin exerts an α-adrenoceptor blocking effect on both human prostatic adenoma tissue and prostatic capsule tissue in vitro. For this therapy the prazosin liposheres are applied to the prostate intrarectally and are exposed to ultrasound as described in Example 17.

Example 20
Ultrasound Enhancement of Delivery of Lipid Soluble Material in vivo

Acoustically Active Liposheres (AALs) were made by adding Sudan Black dye at a concentration of 10 mg/ml to soybean oil. Sudan Black was selected as the marker from an initial experiment that showed that Sudan Black would extract into chloroform and had an absorbance peak from 570 to 620 nm that was not masked by the absorbance of compounds extracted from tissue. 320 µl of this solution was added to 1.5 ml of dipalmitoylphosphatidylcholine dipalmitoylphosphatidylethanolamine coupled to polyethylene glycol 5000, and dipalmitoylphosphatidic acid, in a ratio of about 82%:8%:10% (mole %) and the gas perfluoropropane in a 2 ml Wheaton vial. The headspace was replaced with perfluoropropane and the vial was shaken for 60 seconds on an ESPE capmix. 12 male Balb/C mice were used in the study. A Richmar therapeutic ultrasound machine was used to administer the ultrasound. The animals were divided into 4 groups, no treatment control, Sudan Black AALs with no ultrasound, Sudan Black AALs with 1 W/cm$^2$ ultrasound, Sudan Black AALs with 2 W/cm$^2$ ultrasound. The mouse was immobilized using the Sweitzer immobilization technique. An infusion of 500 µl of AALs was administered over a period of 1 minute via a butterly (25 gauge infusion set) in the tail vein. In those animals that received ultrasound the ultrasound was administered to the left leg throughout the course of the infusion and for one additional minute. Animals were euthanized by $CO_2$ asphyxiation. The left leg was then removed from each animal and the tissue collected. Tissue was then frozen with liquid nitrogen and ground in a mortar and pestle. The tissue was then transferred to a scintillation vial and 2 ml of chloroform added. The tissue was extracted for 2 hours and then filtered through a solvent safe Gelman filter to remove tissue. The sample was placed in a quartz cuvette and scanned from 480 to 700 nm in a Perkin-Elmer Lambda 3 spectrophotometer. Data was transferred to a Macintosh computer and analyzed using the JMP 3.1.5 statistical package.

TABLE 9

| Averages for 3 mice each treatment | | |
|---|---|---|
| Treatment | Sudan Black detected† | St. Dev. |
| 1. 1.0 watt ultrasound | 0.412 | .00623 |
| 2. 2.0 watt ultrasound | 0.798 | .00762 |
| 3. control | 0.0046 | .00623 |
| 4. no ultrasound | 0.0253 | .00623 |

†absorbance in OD units

Example 21
Ultrasound imaging with AALs

In vivo ultrasound imaging was performed with AALs in a dog. The dog was administered general anesthesia, intubated and respired mechanically. The dog was instrumented with pulmonary arterial pressure and arterial pressure monitors as well as pulse oximetry and EKG. Ultrasound imaging was performed with a model 5200S Acoustic Imaging clinical ultrasound scanner (Acoustic Imaging, Tempe, Ariz.) at 7.5 MHz with a curvilinear transducer. Imaging was performed pre contrast and post contrast after IV injection of a bolus of different formulations of AALs. A comparison injection with imaging was also performed with DPPC:DPPE-PEG:DPPA (82%:8%:10% (mole %)) perfluorobutane gas filled contrast agent. Formulations of AALs which were tested included vesicles with two different concentrations of either dexamethasone, amphotericin or Sudan Black. The AALs were previously prepared by dissolving 10 micrograms per ml of either dexamethasone, amnphotericin or Sudan Black into soya bean oil. Phospholipids including 82:10:8 mole percent DPPC, DPPA and DPPE-PEG5,000 were previously suspended at a lipid concentration of 1 mg in 8:1:1 by weight saline:propylene glycol:glycerol. To 1.5 mls of the phospholipid solution in sterile vials either 80 microliters or 320 microliters of the different stock oil preparations was added. The head space of the vials was evacuated and filled with perfluorobutane. Nitrogen gas was also used to fill some of the samples head spaces. The resulting phospholipid/oil suspensions were then agitated for 60 seconds each on a Wig-L-Bug for 60 seconds producing AALs with low and high oil concentrations. Each different AAL preparation was then injected IV in the dog at a dose of 20 µl/kg and ultrasound imaging was performed. Separate injections were performed for each AAL preparation to image heart and kidney. Images were recorded on videotape. The AALs gave less robust contrast than an equivalent dose of DPPC:DPPE-PEG:DPPA (82%:8%:10% (mole %)) perfluorobutane gas filed contrast agent but the duration of contrast was almost the same. Contrast could be visualized for each perfluorobutane containing AAL preparation in the kidney as well as the heart. Spectral Doppler was performed on the aorta and inferior vena cava which showed increased signal in both these vascular structures indicating that the AALs were stable enough to recirculate. By comparison the AALs containing nitrogen showed less signal in the left ventricle of the heart or the kidney. During bolus injection of the AALs there was no appreciable hemodynamic change in the dog.

The above experiment shows how AALs can be used as a contrast agent and with high energy ultrasound for drug delivery.

Example 22
Preparation of Microsphere Consisting of a Lipid-Based Material Encapsulating an Insoluble Gas A phosphatidylcholine is fluorinated as follows: An omega-bromo carboxylic acid ester ($Br(CH_2)[n]COOCH_2CH_3$) and perfluorisobutylene ($(CF_3)_2CF=CF_2$) are reacted in the presence of CsF and monoglyme at room temperature to form a fluorinated ester ($(CF_3)_3C(CH_2)[n]COOCH_2CH_3$). This ester is hydrolyzed to form a free acid ($(CF_3)_3C(CH_2)[n]COOH$) which is converted to the acyl-chloride ($(CF_3)_3C(CH_2)[n]COCl$) by reacting it with thionyl chloride. The acylchloride is reacted in the presence of base with glycerophosphocholine to form the fluorinated glycerophosphocholine.

The length of the carbon chain of the bromo carboxylic acid ester used can be varied, for example between C5 and C20.

Microspheres are formed by first emulsifying the following ingredients to form an oil-in-water emulsion: fluorinated glycerophosphocholine (either alone or in combination with other lecithins), an insoluble gas and water. Optionally, the emulsion contains triolein, cholesterol and/or a-tocopherol. Homogenization of the emulsion is carried out under pressure and at a temperature above the transition temperature of the fluorinated glycerophosphocholine, followed by cooling to room temperature.

The disclosures of each patent, patent application and publication cited or described in this document are hereby incorporated herein by reference, in their entirety.

Various modifications of the invention, in addition to those described herein, will be apparent to those skilled in the art from the foregoing description. Such modifications are also intended to fall within the scope of the appended claims.

What is claimed is:

1. A method for the controlled delivery of a therapeutic compound to a region of a patient comprising: (i) administering to a patient a targeted therapeutic delivery system comprising, in combination with a therapeutic compound, stabilized lipid microspheres encapsulating a gas or gaseous precursor and an oil, wherein said microspheres comprises at least one phosphatidylcholine, at least one phosphatidylethanolamine, and at least one phosphatidic acid, wherein said phosphatidylcholine is selected from the group consisting of dioleoylphosphatidylcholine dimyistoylphosphatidylcholine, dipalmitoylphosphatidylcholine, and distearoyl-phosphatidylcholine; said phosphatidylethanolamine is selected from the group consisting of dipalmitoylphosphatidylethanolamine, dipalmitoylphosphatidylethanolamine-PEG 5,000, dioleoyl-phosphatidylethanolamine, and N-succinyl-dioleoyl-phosphatidylethanolamine; and said phosphatidic acid is dipalmatoylphosphatidic acid; (ii) monitoring the targeted therapeutic delivery system using diagnostic ultrasound to determine the presence of the microspheres in said region; and (iii) applying therapeutic ultrasound to said region to induce rupturing of said microspheres, thereby releasing the therapeutic compound in said region, wherein said therapeutic compound is encapsulated or embedded in said microspheres, and said therapeutic ultrasound is applied at a level below the threshold level for lethal cytotoxicity.

2. A method of claim 1 for use in treating macular degeneration wherein said therapeutic compound comprises a-tocopherol and retinoic acid, said oil is soybean oil, said microspheres comprise 82 mol percent dipalmitoylphosphatidyl choline, 10 mol percent dipalmitoylphosphatidic acid, and 8 mol percent dipalmitoylphosphatidyl ethanolamine-polyethylene glycol 5000, and said gaseous precursor is perfluorobutane.

3. A method of claim 1 for use in treating retinoblastoma wherein said therapeutic compound comprises taxol and retinoic acid, said oil is soybean oil, said microspheres comprise 82 mol percent dipalmitoylphosphatidyl choline, 10 mol percent dipalmitoylphosphatidic acid, and 8 mol percent dipalmitoylphosphatidyl ethanolamine-polyethylene glycol 5000, and said gaseous precursor is perfluorobutane.

4. A method of claim 1 wherein said therapeutic compound is amphotericin-B, said oil is soybean oil, said microspheres comprise 82 mol percent dipalmitoylphosphatidyl choline, 10 mol percent dipalmitoylphosphatidic acid, 8 mol percent dipalmitoylphosphatidylethanolamine-polyethylene glycol 5000 and apoloxamer, and said gaseous precursor is perfluorobutane.

5. A method of claim 4 used to treat fungal ophthalmitis.

6. A method of claim 1 for treating retinitis pigmentosa wherein said therapeutic compound is bendazac, said oil is soybean oil, said microspheres comprise 82 mol percent dipalmitoylphosphatidyl choline, 10 mol percent dipalmitoylphosphatidic acid, 8 mol percent dipalmitoylphosphatidylethanolamine-polyethylene glycol 5000 and a poloxamer, and said gaseous precursor is perfluorobutane.

7. A method of claim 1 for eating benign prostatic hyperplasia wherein said therapeutic compound is doxazosin, said oil is soybean oil, said micropheres comprises 82 mol percent dipalmitoylphosphatidyl choline, 10 mol percent dipalmitoylphosphatidic acid, 8 mol percent dipalmitoylphosphatidyl ethanolamine-polyethylene glycol 5000 and a poloxamner, and said gaseous precursor is perfluorobutane.

8. A method of claim 1 wherein said therapeutic compound is α-tocopherol, said microspheres comprises $CF_3(CF_2)_8(CH_2)_6COOH$, said oil is canola oil, and said gaseous precursor is perfluorobutane.

9. A method of claim 1 wherein said therapeutic compound is a dye, said oil is soybean oil, said micropheres comprises 82 mol percent dipalmitoylphosphatidylcholine, 8 mol percent dipalmitoylphosphatidylethanolamine-polyethylene glycol 5000, and 10 mol percent dipalmitoylphosphatidic acid, and said gaseous precursor is perfluoropropane.

10. A method of claim 1 wherein said therapeutic compound is dexamethasone, said micropheres comprises 82 mol percent dipalmitoylphosphatidylcholine, 8 mol percent dipalmitoylphosphatidylethanolamine-polyethylene glycol 5000, and 10 mol percent dipalmitoylphosphatidic acid, and said gas is perfluorobutane and nitrogen.

11. A method of claim 1 wherein said therapeutic compound is amphotericin, said micropheres comprises 82 mol percent dipalmitoylphosphatidylcholine, 8 mol percent dipalmitoylphosphatidylethanolamine-polyethylene glycol 5000, and 10 mol percent dipalmitoylphosphatidic acid, and said gas is selected from the group consisting of perfluorobutane and nitrogen.

12. A method of claim 1 for treating prostate cancer or benign prostate hypertrophy wherein said therapeutic compound is selected from the group consisting of testosterone, methyltestosterone, fluoxymesterone, finasteride, and 5α reductase enzyme inhibitors.

13. A method according to any preceding claim wherein said diagnostic ultrasound has a frequency equal to 1×, and wherein said therapeutic ultrasound has a frequency equal to 2×, 3×, or 5×.

14. A method according to claim 13 wherein said therapeutic ultrasound is superimposed upon said diagnostic ultrasound.

15. A method according to claim 14 wherein said therapeutic ultrasound is administered as a train of continuous wave pulses.

* * * * *